United States Patent [19]

Huguet et al.

[11] Patent Number: 4,888,358
[45] Date of Patent: Dec. 19, 1989

[54] 13,14-DIHYDROPROSTAGLANDIN C-TYPE DERIVATIVES

[75] Inventors: Joan Huguet, Ciudad Satelite, Mexico; Joseph M. Muchowski, Sunnyvale, Calif.; Maria T. Lara, Toluca, Mexico

[73] Assignee: Syntex (U.S.A.) Inc., Palo Alto, Calif.

[21] Appl. No.: 236,697

[22] Filed: Aug. 25, 1988

[51] Int. Cl.$^4$ ............... C07C 177/00; A61K 31/557
[52] U.S. Cl. ........................... 514/530; 514/568;
    514/573; 560/51; 560/53; 560/118; 560/121;
    562/459; 562/463; 562/500; 562/503
[58] Field of Search ............ 560/121, 51, 53, 118;
    562/503, 454, 463, 500; 514/530, 568, 573

[56] References Cited

U.S. PATENT DOCUMENTS

| | | | |
|---|---|---|---|
| 3,872,149 | 3/1975 | Crabbe | 560/121 |
| 3,993,686 | 11/1986 | Kelly | 560/121 |
| 4,051,160 | 9/1977 | Bundy et al. | 560/121 |
| 4,082,782 | 4/1978 | Morton, Jr. | 560/121 |
| 4,082,789 | 4/1978 | Jones | 560/121 |

FOREIGN PATENT DOCUMENTS 148337 of 0000 Fed. Rep. of Germany ...... 560/121

Primary Examiner—Robert Gerstl
Attorney, Agent, or Firm—Brian Lewis; Tom Moran

[57] ABSTRACT

Novel 13,14-dihydroprostaglandin derivatives of the formula

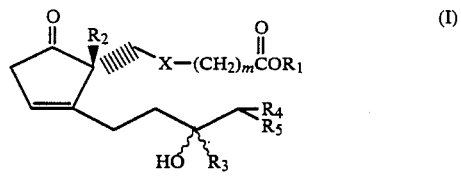

wherein:
m is 1 or 3;
$R_1$ is hydrogen or alkyl;
$R_2$ is hydrogen or lower alkyl;
$R_3$ and $R_4$ are independently hydrogen or methyl;
$R_5$ is alkyl, $CF_3(CH_2)_n$— in which n is an integer of 3–5, cycloalkyl, or optionally substituted phenyl, benzyl or phenoxy; or
$R_4$ and $R_5$ taken together with the carbon to which they are attached is cycloalkyl of 4–8 carbon atoms;
X is cis —CH=CH— or —CH$_2$CH$_2$— when m is 3, or
X is —CH$_2$CH=C=CH— when m is 1;
and the wavy lines represent the $\alpha$ or $\beta$ configuration with the proviso that when one wavy line is $\alpha$ the other is $\beta$;
or a pharmaceutically acceptable salt thereof,
have been prepared. They are useful in particular for their antihypertensive and anti-ulcerogenic properties.

28 Claims, No Drawings

13,14-DIHYDROPROSTAGLANDIN C-TYPE DERIVATIVES

BACKGROUND OF THE INVENTION

1. Field of the Invention

This invention relates to various novel 13,14-dihydroprostaglandin C-type derivatives which posses the wide spectrum of pharmacological activities normally associated with prostaglandin derivatives. They are particularly useful as antihypertensive and anti-ulcerogenic agents.

2. Related Disclosures

The preparation of prostaglandin derivatives has assumed great importance due to the high potency in mammals of such compounds for a wide range of activities, for example gastric acid secretion inhibition, platelet aggregation inhibition, bronchodilation, as hypotensive agents, abortificants, etc. Although prostaglandin C-type (PGC) derivatives exhibit the above spectrum of activities they are less widely known, and little effort has been made to synthesize and test them for medicinal purposes because of the ease of isomerization of the PGC derivatives to prostaglandin B-type (PGB) compounds, which are in general much less active for the above indications. The compounds of our invention, the 13,14-dihydro PGC compounds, are more resistant to such isomerization and thus retain the high level of pharmacological activities associated with PGC derivatives.

PGC derivatives which are known in the art include, for example, U.S. Pat. No. 4,082,789 to Jones, U.S. Pat. No. 3,993,686 to Kelly and U.S. Pat. No. 3,872,149 to Crabbe.

SUMMARY OF THE INVENTION

One aspect of the invention concerns novel compounds represented by the formula:

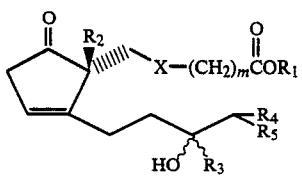

wherein:
m is 1 or 3;
$R_1$ is hydrogen or alkyl of 1-6 carbon atoms;
$R_2$ is hydrogen or lower alkyl of 1-4 carbon atoms;
$R_3$ and $R_4$ are independently hydrogen or methyl;
$R_5$ is alkyl of 4-10 carbon atoms, $CF_3(CH_2)_n$—in which n is an integer of 3-5, cycloalkyl of 4-8 carbon atoms, or phenyl, benzyl or phenoxy in which any phenyl group may be optionally substituted with one or two substituents chosen from lower alkyl of 1-4 carbon atoms, lower alkoxy of 1-4 carbon atoms, lower thioalkyl of 1-4 carbon atoms, halogen, trifluoromethyl and trifluoromethoxy; or
$R_4$ and $R_5$ taken together with the carbon to which they are attached is cycloalkyl of 4-8 carbon atoms;
X is cis —CH=CH— or —CH$_2$CH$_2$— when m is 3, or
X is —CH$_2$CH=C=CH— when m is 1;

and the wavy lines represent the α or β configuration with the proviso that when one wavy line is α the other is β;
or a pharmaceutically acceptable, non-toxic salt thereof.

Other aspects of the invention relate to the methods of preparation of compounds of formulas (I) thereof, to the novel intermediates produced in such methods of preparation, to pharmaceutical compositions containing such compounds in admixture with one or more pharmaceutically acceptable, non-toxic carriers, and to methods pertaining to their use.

DETAILED DESCRIPTION OF THE INVENTION

Definitions

As used herein:

"Protecting group" means any suitable chemical group that is commonly used in the practice of organic chemistry to modify one or more of the major functional groups in a molecule for the purpose of selectively performing a chemical reaction at another reactive site in a multifunctional molecule. A protecting group is typically formed in a selective manner and is stable to subsequent reactions on the molecule and is selectively removed by reagents that do not attack the regenerated functional group. Suitable protecting groups for the hydroxyl group are: ethers including methyl ethers, substituted methyl ethers, substituted ethyl ethers, tetrahydropyranyl ethers, silyl ethers including trimethylsilyl, triethylsilyl, isopropyldimethylsislyl, t-butyldimethylsilyl, (triphenylmethyl)dimethylsilyl, t-butyldiphenylsilyl, and the like; esters including formate esters, acetate esters and their derivatives such as chloroacetate, trichloroacetate, trifluoroacetate, and the like, adamantoate, crotonate, benzoate and substituted benzoate derivatives, and the like; carbonates including methyl, ethyl, 2,2,2-trichloroethyl, isobutyl, vinyl, allyl, benzyl and derivatives such as p-methoxybenzyl, o-nitrobenzyl, and the like, carbamates including N-phenylcarbamate, N-imidazolylcarbamate, and the like, borate, N,N,N',N'-tetramethylphosphorodiamidate, 2,4-dinitrophenylsulfenate, and the like as well as protection for 1,2-and 1.3- diols including cyclic acetals and ketals, cyclic ortho esters and the like.

The 15-hydroxy group is preferably protected with a silyl group, shown herein as $R_6$. Particularly preferred are t-butyldimethylsilyl, triisopropylsilyl, triphenylsiyl, t-butyldiphenylsilyl and 2,4,6-tri-t-butylphenoxydimethylsilyl groups. When a silylating agent is employed, standard conditions normally used for such a reagent may be used. For example, the reaction is generally carried out in a polar aprotic solvent with an excess of the silylating reagent, 2.2 to 4 equivalents, and a greater excess relative to the silylating reagent of a mild base such as imidazole.

Preferably, the imidazole and about 3 equivalents of t-butyldimethylsilyl chloride will be added to a dry dimethylformamide solution of the hydroxy acid salt and stirred overnight at about room temperature, completion of the reaction being confirmed by TLC.

$R_7$ is defined herein as an "acid-labile, base-stable protecting group". Such a group, useful for the protection of hydroxy, may be any ether-forming group which will not be hydrolyzed when treated with a strong aqueous base such as sodium or potassium hydroxide, yet will be hydrolyzed back to the original hydroxy group by acid under mild conditions which will not result in degradation of the desired product. Examples of groups which are acid-labile yet base-stable are tetrahydrofuranyl, tetrahydropyranyl, 2-ethoxyethyl and the like. Generally excluded from this definition are alkyl ethers, benzyl ethers and alkylaryl ethers, and the like, because the conditions normally required to effect acid hydrolysis of these latter ethers would be expected to cause product degradation during the hydrolysis process, if in fact their hydrolysis would be effected by acid at all.

To avoid any possibility of ambiguity, it should be understood that the particular definition of compounds of formula (I) where m is 1 and X is —CH$_2$CH═C═CH— is intended to encompass only compounds of the formula:

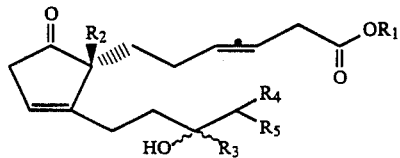

Compounds having an allene group are represented herein as having substituents on one end of the allene group which are oriented at 90° to those on the other end. When both sides of the allene are dissymmetric the allene moiety is rendered asymmetric.

The terms "α and β" indicate the specific stereochemical configuration of a substituent at an asymmetric carbon atom in a chemical structure as drawn. Thus "α", denoted by a broken line, indicates that the group at the position in question is below the general plane of the molecule as drawn, and "β", denoted by a bold line, indicates that the group at the position in question is above the general plane of the molecule as drawn.

The compounds of this invention possess asymmetric centers and thus can be produced as mixtures of stereoisomers or as individual R or S stereoisomers. The individual enantiomers may be obtained by resolving a racemic or non-racemic mixture of an intermediate at some appropriate stage of the synthesis. It is understood that the individual R or S stereoisomers as well as mixtures of stereoisomers are encompassed within the scope of the present invention.

The term "(±)" is used to designate a racemic mixture of individual (+) and (−) isomers. The (±) racemate as well as the individual (+) and (−) enantiomers and non-racemic mixtures thereof are included within the scope of this invention.

For the sake of simplicity only one stereoisomer will be depicted by way of illustration in the Reaction Schemes. However, it is to be understood that all individual stereoisomers and mixtures thereof are also encompassed thereby, they being obtained by starting with the corresponding mixtures of stereoisomers or individual stereoisomer.

The use of the symbol "R" or "S" preceding a substituent designates the absolute stereochemistry of that substituent according to the Cahn-Ingold-Prelog rules [see Cahn et al., Angew. Chem. Inter. Edit., Vol. 5, p. 385 (1966), errata p. 511; Cahn et al., Angew. Chem., Vol. 78, p. 413 (1966); Cahn and Ingold, J. Chem. Soc., (London), 1951, p. 612; Cahn et al., Experientia, Vol. 12, p. 81 (1956); Cahn J. Chem. Educ., Vol. 41, p. 116 (1964)]. Because of the interrelation of the designated substituent with the other substituents in a compound having α or β prefixes, the designation of the absolute configuration of one substituent fixes the absolute configuration of all substituents in the compound and thus the absolute configuration of the compound as a whole.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other.

"Diastereoisomers" are stereoisomers which are not mirror-images of each other.

"Epimers" are diastereoisomers which differ only in the configuration of one asymmetric center.

"Racemic mixture" means a mixture containing equal parts of individual enantiomers. "Non-racemic mixture" is a mixture containing unequal parts of individual enantiomers.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

"Alkyl" means a branched or unbranched saturated hydrocarbon chain containing 1 to 10 carbon atoms, such as methyl, ethyl, propyl, tert-butyl, n-hexyl, 2-methylheptyl, n-decyl and the like;

"Lower alkyl" means a branched or unbranched saturated hydrocarbon chain containing 1 to 6 carbon atoms, such as methyl, ethyl, propyl, isopropyl, tert-butyl, butyl, n-hexyl and the like, unless otherwise indicated.

"Cycloalkyl" as used herein means a saturated monovalent monocyclic hydrocarbon radical containing 3–8 carbon atoms, such as cyclopropyl, cyclobutyl, cyclopentyl, cyclohexyl, cycloheptyl and cyclooctyl.

"Lower alkoxy" means the group —OR wherein R is lower alkyl as herein defined.

The term, "lower thioalkyl" refers to a branched or unbranched saturated monovalent hydrocarbon chain of 1–4 carbons attached to a sulfur atom, such as, for example, thiomethyl, thioethyl, thio-n-propyl, thio-i-butyl and the like.

"Halo" as used herein denotes fluoro, chloro, bromo, or iodo.

"Phenyl" as used herein encompasses all possible isomeric phenyl radicals optionally monosubstituted or disubstituted with a substituent selected from the group consisting of lower alkyl, lower alkoxy, hydroxy, trifluoromethyl and halo.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and substituted phenyl; "optionally followed by converting the free base to the acid addition salt" means that said conversion may or may not be carried out in order for the process described to fall within the invention, and the invention includes those processes wherein the free base is converted to the acid addition salt and those processes in which it is not.

The term "ylide or stabilized anion normally associated with an olefination reaction" refers to compounds of the type (R')$_3$P=CR''R'' (ylides), or (R'O)$_2$P(O)CR''R'' or (R')$_2$P(O)CR''R'' (stabilized anions), where R' is alkyl or phenyl and R'' is independently hydrogen or alkyl optionally substituted with, for example, —(CH$_2$)$_n$CO$_2$R'', —(CH$_2$)$_n$CN and the like. Such compounds react with an aldehyde or ketone to give an olefin where the position of the double bond is predictable. Ylides and stabilized anions where phosphorus is replaced by sulfur, silicon or nitrogen are also known and are included in this definition.

The term "pharmaceutically acceptable, non-toxic salt" refers to those base-addition salts of any compound herein having a carboxylic acid function. These salts are derived from pharmaceutically acceptable, non-toxic inorganic or organic bases.

Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic, non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, N-methylglucamine, theobromine, purines, piperazine, piperidine, N-ethylpiperidine, polyamine resins and the like. Particularly preferred organic non-toxic bases are isopropylamine, diethylamine, ethanolamine, tromethamine, dicyclohexylamine, choline and caffeine.

The base-addition salts of these compounds, where appropriate to make, are prepared by treating the corresponding free acids of the compounds with at least one molar equivalent of a pharmaceutically acceptable base. Representative bases are sodium hydroxide, sodium bicarbonate, potassium carbonate, ammonium hydroxide, calcium hydroxide, trimethylamine, lysine, caffeine, and the like. The reaction is conducted in water, alone or in combination with an inert, water-miscible organic solvent, at a temperature of from about 0° C. to about 40° C., preferably at room temperature. Typical inert, water-miscible organic solvents include methanol, ethanol, or dioxane. The molar ratio of compounds of formula (I) to base used are chosen to provide the ratio desired for any particular salt.

Formula (I) as represented herein includes any of the single structures shown below (Ia, Ib, Ic and Id), all permutations of two or three components in any proportions, and mixtures of all four components in any proportions.

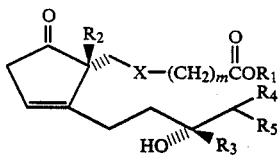
(Ia)

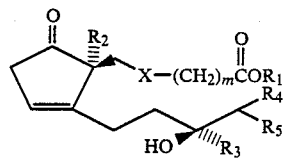
(Ib)

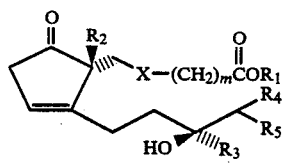
(Ic)

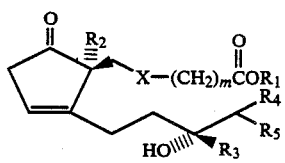
(Id)

In addition, in the compounds where X is —CH$_2$CH=C=CH— and m is 1 a further chiral center is introduced. All racemic and non-racemic mixtures resulting as a consequence of this allenic chiral center are encompassed by the definition of the compound of formula (I), as well as the individual allenic isomers.

The numbering of the compounds of formula (I), unless otherwise indicated, follows that in use for the naturally occuring prostaglandins, which may be considered as derivatives of prostanoic acid, illustrated by the following example of a prostanoic acid:

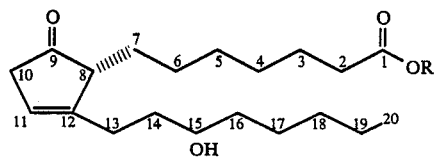

Prostaglandins have been divided into families designated as A, B, C, D, E, F, G and H, which differ from one another in the functionality of the five-membered ring. Thus prostaglandins of the C family have a double bond at the 11 position, as shown above. Prostaglandins of the B family have a double bond between the 8 and 12 position, the A family a double bond at the 10 position, etc. The numbering system is shown in more detail in *J. Med. Chem.*, Vol. 17, 911 (1974), which is hereby incorporated by reference.

Following are examples of how representative compounds of formula (I) are named:

A racemic compound of formula (I) wherein X is —CH=CH— and m is 3, R$_1$ is methyl, R$_2$ and R$_3$ are hydrogen, and R$_4$ and R$_5$ taken together is cyclohexyl is named (±)-9-oxo-15-hydroxy-15-cyclohexyl-16,17,18,-19,20-pentanorprosta-5(Z),11-dienoic acid, methyl ester.

One optical isomer of a compound of formula (I) wherein X is —CH$_2$CH$_2$— and m is 3, R$_1$ and R$_2$ are methyl, R$_3$ and R$_4$ are hydrogen and R$_5$ is phenoxy is named (8R,15S)-8-methyl-9-oxo-15-hydroxy-16-phenoxy-17,18,19,20-tetranorprosta-11-enoic acid, methyl ester.

A racemic compound of formula (I) wherein X is —CH$_2$CH=C=CH— and m is 1, R$_1$ is methyl, R$_2$, R$_3$ and R$_4$ are hydrogen and R$_5$ is n-butyl is named (±)-9- oxo-15-hydroxyprosta-3,4,11-trienoic acid, methyl ester.

For the purposes of consistency, in this disclosure (unless otherwise indicated) a carbon of a particular intermediate is identified by the number it will have in the final product, i.e. formula (I). However, in the exemplary Preparations, the intermediates 1–6, 9–12, 15 and 21–24 are named as cyclopentane derivatives and numbered accordingly.

PREFERRED EMBODIMENTS

Among the family of compounds of the present invention, a first preferred group includes compounds where X is —CH=CH— and m is 3. Within this group a preferred subgroup includes the compounds in which $R_2$ is hydrogen or methyl and $R_3$ is hydrogen, especially where $R_1$ is methyl. One preferred class within this subgroup includes compounds in which $R_4$ is hydrogen and $R_5$ is phenoxy or n-butyl, and compounds in which $R_4$ and $R_5$ taken together with the carbon to which they are attached is cyclohexyl.

A second preferred group includes compounds where X is —CH$_2$CH$_2$— and m is 3. Within this group a preferred subgroup includes the compounds in which $R_2$ is hydrogen or methyl and $R_3$ is hydrogen, especially where $R_1$ is methyl. One preferred class within this subgroup includes compounds in which $R_4$ is hydrogen and $R_5$ is phenoxy or n-butyl, and compounds in which $R_4$ and $R_5$ taken together with the carbon to which they are attached is cyclohexyl.

A third preferred group includes compounds where X is —CH$_2$CH=C=CH— and m is 1. Within this group a preferred subgroup includes the compounds in which $R_2$ is hydrogen or methyl and $R_3$ is hydrogen, especially where $R_1$ is methyl. One preferred class within this subgroup includes compounds in which $R_4$ is hydrogen and $R_5$ is phenoxy or n-butyl, and compounds in which $R_4$ and $R_5$ taken together with the carbon to which they are attached is cyclohexyl.

At present, the preferred compounds are:
(8R,15S)-9-oxo-15-hydroxy-16-phenoxy-17,18,19,20-tetranorprosta-5(Z),11-dienoic acid, methyl ester;
(8R,15R)-9-oxo-15-hydroxy-16-phenoxy-17,18,19,20-tetranorprosta-5(Z),11-dienoic acid, methyl ester;
(8R,15RS)-8-methyl-9-oxo-15-hydroxy-16-phenoxy-17,18,19,20-tetranorprosta-5(Z),11-dienoic acid, methyl ester;
(±)-9-oxo-15-hydroxy-15-cyclohexyl-16,17,18,19,20-pentanorprosta-5(Z),11-dienoic acid, methyl ester;
(±)-9-oxo-15-hydroxyprosta-5(Z),11-dienoic acid, methyl ester;
(8R,15S)-9-oxo-15-hydroxy-16-phenoxy-17,18,19,20-tetranorprosta-11-enoic acid, methyl ester; and
(8R,15S)-9-oxo-15-hydroxy-16-phenoxy-17,18,19,20-tetranorprosta-3,4,11-trienoic acid, methyl ester.

METHODS OF PREPARATION (A) Where X is cis —CH=CH— and m is 3

The synthesis of the compounds of formula (I) where X is cis —CH=CH— and m is 3 starts from the compound of formula (6), which may prepared by two different routes as shown in Reaction Schemes I and II below.

For the sake of simplicity only one stereoisomer will be depicted in the illustration of the Reaction Schemes. However, it is to be understood that mixtures of all possible stereoisomers and the individual stereoisomers are also encompassed thereby. For example, the depiction of the compound of formula (5) is intended to represent not only the 15α-epimer as drawn but also the 15β-epimer, mixtures of the two and racemic mixtures thereof.

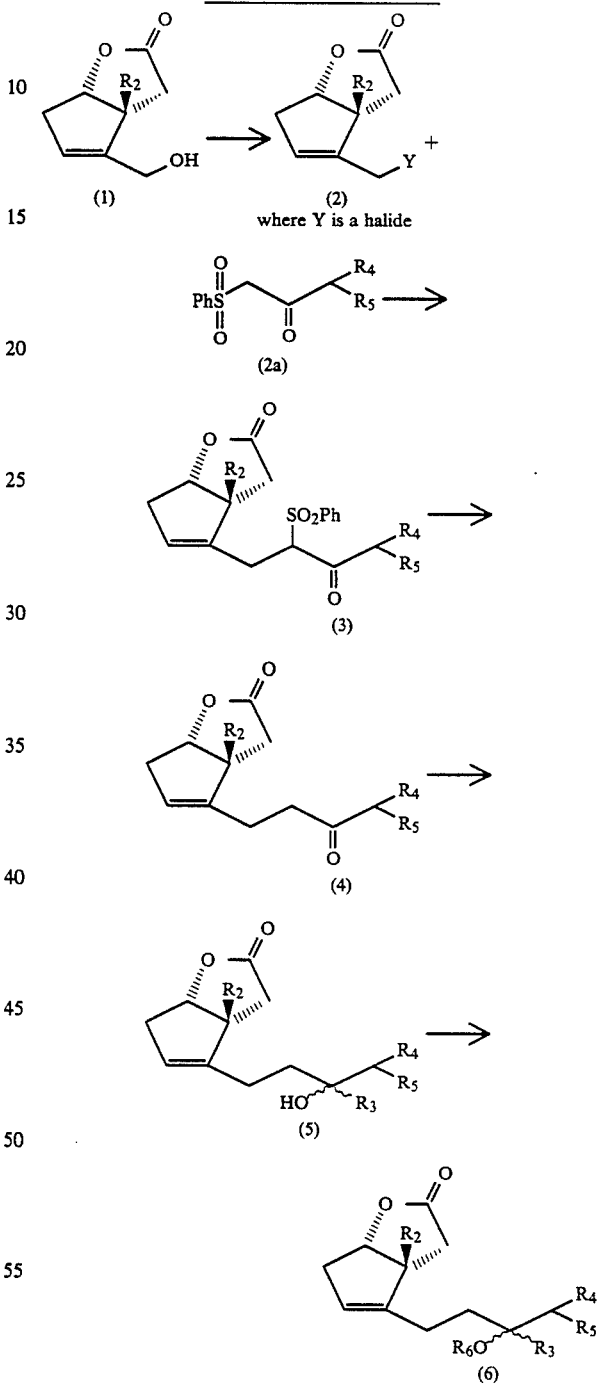

where $R_2$, $R_3$, $R_4$ and $R_5$ are as defined above, and $R_6$ is a protecting group.

One method for the preparation of the compound of formula (6) is shown in Reaction Scheme I, starting from the known compound of formula (1). The hydroxyl group is first converted to a halide by (a) converting it to bromo, chloro or iodo by reacting with conventional reagents such as a thionyl halide, or triphenylphosphine and a carbon tetrahalide, or preferably (b) by reacting it with an alkylsulfonyl halide, for example methanesulfonyl chloride, or most preferably an arylsulfonyl halide, for example p-toluenesulfonyl chloride. Typically, the alcohol of formula (1) is dissolved in an inert solvent such as benzene, toluene, acetonitrile, diethyl ether, chloroform, tetrahydrofuran or preferably methylene chloride and reacted with from 1 to 3 molar equivalents, preferably about 1.2 molar equivalents, of the chosen sulfonate, preferably p-toluenesulfonyl chloride in the presence of about 0.1 to 1 molar equivalents, preferably about 0.8 molar equivalents, of 4-dimethylaminopyridine and from 1–5 molar equivalents, preferably about 1.2 molar equivalents, of an inorganic base such as sodium carbonate, potassium bicarbonate or the like, or preferably a tertiary organic base, such as pyridine, N-methylpiperidine and the like, or preferably triethylamine. The reaction is carried out at a temperature of about 0°–40° C., preferably about 25°, for about 1–10 hours, preferably about 2 hours. When the reaction is substantially complete, the product of formula (2) is isolated and purified by conventional means, preferably chromatography.

In the next step, the compound of formula (2) is reacted with the compound of formula (2a), which is prepared from the reaction of the anion of phenylmethyl sulfone and the appropriate compound of formula $R_4R_5CHCO_2R$, where R is alkyl, preferably ethyl, and $R_4$ and $R_5$ are as defined above. For example, phenylmethyl sulfone is dissolved in an inert ethereal solvent such as dioxane, dimethoxyethane, diethylether or preferably tetrahydrofuran and cooled to a temperature of about $-100°$ C. to $-20°$ C., preferably about $-70°$ C., and about 1 molar equivalent of an alkyllithium, preferably n-butyllithium, added. The mixture is then allowed to warm to a temperature of about $-20°$ C. for about 5 minutes to 2 hours, preferably about 25 minutes, and then recooled to the original temperature, preferably about $-70°$ C., and about 0.3 to 1 molar equivalents, preferably about 0.6 molar equivalents, of the compound of formula $R_4R_5CHCO_2R$ added slowly. The mixture is reacted for about 5–30 hours, preferably about 14 hours, at a temperature of about 0°–40° C., preferably about 25°. When the reaction is substantially complete, the product of formula (2a) is isolated and purified by conventional means, preferably chromatography.

The compound of formula (2) is then reacted with the compound of formula (2a). Typically, the compound of formula (2) is reacted with about 1.0 to 2 molar equivalents, preferably about 1.2 molar equivalents, of the compound of formula (2a) in a polar aprotic solvent such as dimethylsulfoxide, sulfolane or preferably N,N-dimethylformamide in the presence of a mild base, preferably potassium carbonate. The mixture is reacted for about 1–10 hours, preferably about 4 hours, at a temperature of about 25°–50° C., preferably about 40°, followed by reaction for about a further 1 hour at a temperature of about 50° C. When the reaction is substantially complete, the product of formula (3) is isolated and purified by conventional means, preferably chromatography.

The compound of formula (3) is then reduced to the compound of formula (4), using for example aluminum/mercury amalgam in tetrahydrofuran/water as a solvent, calcium metal in ammonia, sodium/mercury amalgam in methanol or preferably zinc in acetic acid. Typically, the compound of formula (3) is dissolved in an aliphatic carboxylic acid, preferably acetic acid, and about 10 to 100 molar equivalents, preferably about 20 molar equivalents, of zinc powder is added. The mixture is refluxed for about 1–40 minutes, preferably about 10 minutes. When the reaction is substantially complete, the product of formula (4) is isolated and purified by conventional means, preferably chromatography.

To prepare the compound of formula (5) where $R_3$ is hydrogen, the compound of formula (4) is then reduced with a reducing agent such as aluminum hydride, diborane or preferably sodium borohydride. Typically, the ketone of formula (4) is reacted with about 1 to 2 molar equivalents, preferably about 1 molar equivalent, of sodium borohydride in a protic solvent such as water, ethanol or preferably methanol at a temperature of about $-10°$ C. to 25° C., preferably about 0° C., for about 5 minutes, giving the compound of formula (5). When the reaction is substantially complete, the product of formula (5) where $R_3$ is hydrogen is isolated and purified by conventional means, preferably chromatography.

Reduction of the compound of formula (4) with a chiral reducing agent leads to either a 15α-hydroxy or a 15β-hydroxy epimer of the compound of formula (5). An example of such a chiral reducing agent is a complex aluminum hydride modified by chiral 2,2'-dihydroxy-1,1'-binaphthyl (preferably (S)-BINAL-H). See, for example, Tet. Lett., (1981), 247 and J.O.C., Vol. 52, 5406 (1987).

To prepare the compound of formula (5) where $R_3$ is methyl, the compound of formula (4) is reacted with an organometallic compound such as methyllithium or preferably a methylmagnesium halide. Typically, the compound of formula (4) is dissolved in an ethereal solvent such as dioxane, tetrahydrofuran or preferably diethyl ether and reacted with about 1 to 5 molar equivalents, preferably about 2 molar equivalents, of an organometallic compound such as methyllithium or preferably a methylmagnesium halide, most preferably methylmagnesiun bromide. The reaction is carried out at a temperature of about 0°–50° C., preferably about 5° C., for about 2–48 hours, preferably about 18 hours. When the reaction is substantially complete, the product of formula (5) where $R_3$ is methyl is isolated as above.

The hydroxy group of the compound of formula (5) is then protected by forming an ether stable to acid conditions, preferably a silyl ether, for example triethylsilyl ether or most preferably t-butyldimethylsilyl ether. When a silylating agent is employed, standard conditions normally used for such a reagent are used. For example, the reaction is generally carried out in a polar aprotic solvent, preferably N,N-dimethylformamide, with an excess of the silylating reagent, 2.2 to 4 equivalents, and a greater excess relative to the silylating reagent of a mild base such as imidazole.

Preferably, the imidazole and about 3 equivalents of t-butyldimethylsilyl chloride is added to a dry dimethylformamide solution of the hydroxy compound and stirred overnight at about room temperature, completion of the reaction being confirmed by tlc. When the reaction is substantially complete, the product of formula (6) is isolated and purified by conventional means, preferably chromatography.

Reaction Scheme II shows a second route for the preparation of the compound (6) where $R_2$ is hydrogen. This is the preferred route for the preparation of the individual epimeric 15-α and 15-β isomers (conventional prostaglandin numbering) of the compound of formula (6) where $R_2$ is hydrogen, which subsequently yield the separate 15α- and 15β-epimers of the compound of formula (I) where $R_2$ is hydrogen.

REACTION SCHEME II

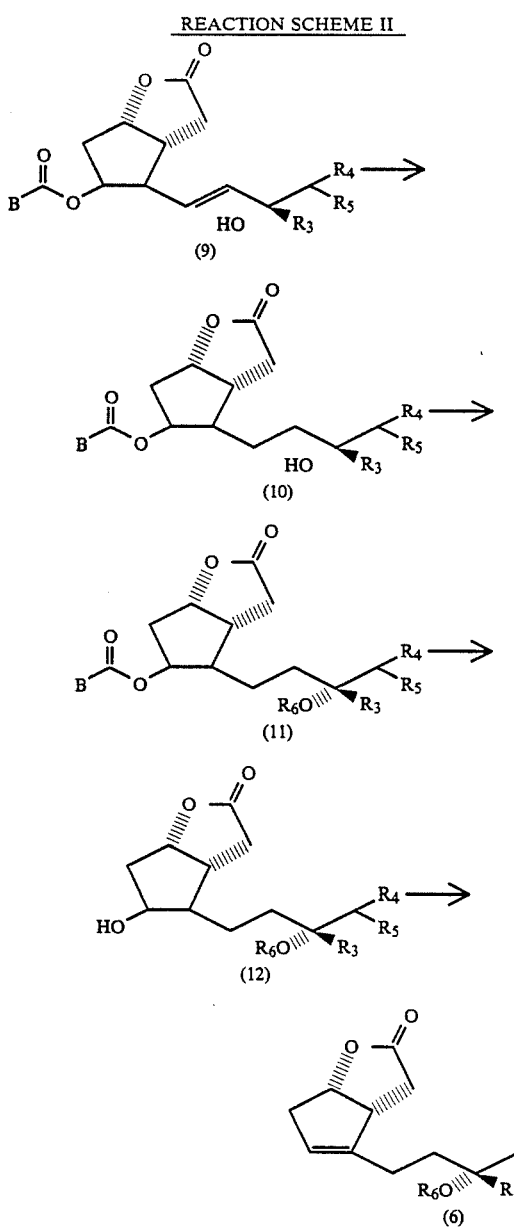

where $R_3$, $R_4$ $R_5$ and $R_6$ are as defined above and B is 4-biphenyl.

The second method for the preparation of the compound of formula (6) where $R_2$ is hydrogen is shown in Reaction Scheme II, starting from the known compound of formula (9). The first step is the catalytic reduction of the 13,14 double bond of (9). Typically, the compound of formula (9), preferably as a pure 15α- or 15β- epimer, is dissolved in a solvent suitable for catalytic hydrogenation, such as methanol, ethanol, tetrahydrofuran or preferably ethyl acetate. This solution is added to a prehydrogenated suspension of a catalyst such as palladium, platinum or preferably Raney-Nickel in a protic solvent, preferably methanol, and hydrogenated at a pressure of about 1–5 atmospheres, preferably about 1 atmosphere, of hydrogen until about 1 molar equivalent of hydrogen is absorbed. The reaction is carried out at a temperature of about 0°–50° C., preferably about 25° C., for about 5–48 hours, preferably about 18 hours. When the reaction is substantially complete, the product of formula (10) is isolated and purified by conventional means, preferably chromatography.

The next step involves the protection of the 15-hydroxy group of the compound of formula (10), preferably as a pure 15α- or 15β- epimer, to give the compound of formula (11). It is protected in the same manner as set forth in Reaction Scheme I above by forming an ether stable to acid conditions, preferably a silyl ether, for example triethylsilyl ether or most preferably t-butyldimethylsilyl ether. When the reaction is substantially complete, the product of formula (11) is isolated by conventional means.

The compound of formula (11), preferably as a pure 15α- or 15β- epimer, is then reacted with a mild base that selectively hydrolyses the biphenyl ester without hydrolysing the lactone group, for example sodium carbonate, calcium carbonate or preferably potassium carbonate. Typically the compound of formula (11) is dissolved in a polar solvent such as dimethylformamide, ethanol or preferably methanol and reacted with about 0.1 to 0.5 molar equivalents, preferably about 0.35 molar equivalents, of the base, preferably anhydrous potassium carbonate. The reaction is carried out at a temperature of about 0°–50° C., preferably about 25° C., for about 5–48 hours, preferably about 24 hours. When the reaction is substantially complete, the product of formula (12) is isolated and purified by conventional means, preferably chromatography.

The compound of formula (12), preferably as a pure 15α- or 15β-epimer, is then dehydrated to give the cyclopentene of formula (6). Typically, the compound of formula (12) is first dissolved in an inert solvent, such as benzene, toluene, acetonitrile, diethyl ether, chloroform, tetrahydrofuran or preferably methylene chloride in the presence of about 1.5 to 10 molar equivalents, preferably about 3 molar equivalent, of a tertiary base, such as pyridine, N-methylpiperidine, triethylamine or preferably 2,4,6-collidine. The mixture is cooled to a temperature of about 0° to −50° C., preferably about −20° C., and about 1 to 3 molar equivalents, preferably about 1.5 molar equivalents, of a dehydrating agent such as trifluoroacetic anhydride, methanesulfonyl chloride, p-toluenesulfonyl chloride or preferably trifluoromethanesulfonic anhydride is added slowly. After about 10 minutes the temperature is allowed to rise to about 0° to 40° C., preferably about 20° C., over a period of about 1–5 hours, preferably about 3 hours. When the reaction is substantially complete, the product of formula (6), preferably as a pure 15α- or 15β- epimer, is isolated and purified by conventional means, preferably chromatography.

Preparation of the Compounds of Formula (I) where X is cis —CH═CH— and m is 3

The preparation of the compounds of formula (I) where X is cis —CH═CH— and m is 3 is illustrated in Reaction Scheme III.

REACTION SCHEME III

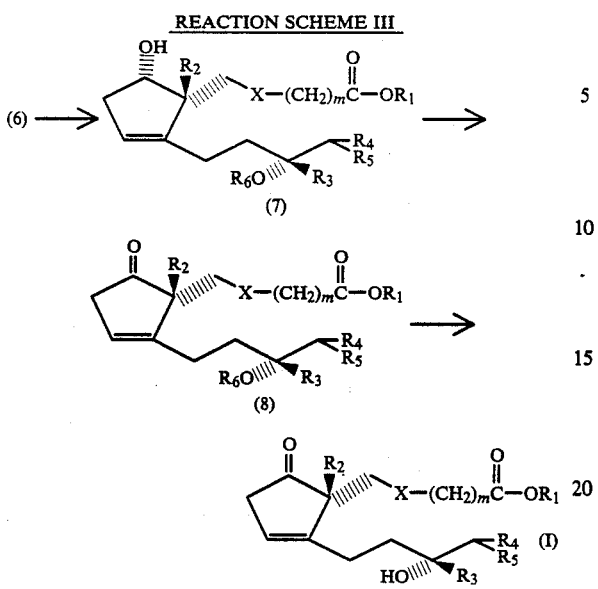

where $R_2$, $R_3$, $R_4$ $R_5$ and $R_6$ are as defined above and $R_1$ is alkyl of 1–6 carbon atoms.

In the first step the compound of formula (6), for example prepared as shown in Reaction Schemes I and II, is dissolved in an inert solvent, for example diethylether, benzene, hexane, tetrahydrofuran or preferably toluene. The solution is cooled to a temperature of about −50° C. to −100° C., preferably about −80° C., and about 1 to 3 molar equivalents, preferably about 1.5 molar equivalents, of a reducing agent such as lithium aluminum hydride, sodium/mercury amalgam at a pH of 3.5, preferably diisobutylaluminum hydride. After about 10 minutes to 2 hours, preferably about 30 minutes, any excess reducing agent remaining is reacted with a protic solvent such as ethanol or preferably methanol and allowed to warm to about room temperature. The mixture is diluted and filtered through Celite, and the solvent removed from the filtrate under reduced pressure.

The residue is then dissolved in an aprotic solvent such as diethyl ether, tetrahydrofuran or preferably dimethyl sulfoxide and reacted with about 1 molar equivalent of an ylide or stabilized anion normally associated with an olefination reaction to give a compound of formula (7). For example, a phosphorus ylide of formula $(R')_3P=CH(CH_2)_3COONa$, where R' is optionally substituted phenyl, prepared from the corresponding phosphonium salt, may be utilized, or a stabilized anion prepared from a compound of the formula $(R'O)_2P(O)CH_2(CH_2)_3CO_2H$ where R' is alkyl or optionally substituted phenyl, or $(R')_2P(O)CH_2(CH_2)_3CO_2H$ where R' is optionally substituted phenyl.

Preferably, triphenylphosphine is reacted with 5-halopentanoic acid, preferably 5-bromopentanoic acid, as described in *J. Org. Chem.*, 27, 3404 (1962). The resulting phosphonium salt is slurried in an aprotic solvent such as diethyl ether, tetrahydrofuran or preferably dimethyl sulfoxide, at a temperature of about 0°–40° C., preferably about 25° C., and about 2.2 molar equivalents of a strong base added, such as butyl lithium, sodium amide, potassium hydride, sodium alkoxide or preferably dimsyl sodium in dimethyl sulfoxide. The solution of the compound of formula (6) is then added and the reaction allowed to proceed for about 30 minutes to 5 hours, preferably about 2 hours. When the reaction is substantially complete, the product is isolated conventionally and then dissolved in an ethereal solution containing an excess of a diazoalkane, preferably diazomethane. After about 5 minutes the product is isolated and purified conventionally, preferably by chromatogrphy, to give the compound of formula (7), as a pure 15α- or 15β- isomer or a mixture of the two, depending on the stereochemistry of the starting compound of formula (6).

The alcohol of formula (7), prepared as shown above or as in Reaction Schemes IV and V below, is then converted to the ketone of formula (8), using an oxidizing agent such as an aqueous solution of chromic acid and sulfuric acid (Jones reagent), sodium dichromate or an organic chromium reagent, such as pyridinium chlorochromate or preferably pyridinium dichromate. Typically, the alcohol is reacted with about 2 to 10 molar equivalents, preferably about 5 molar equivalents, of pyridinium dichromate in an inert solvent such as chloroform, methylene chloride or preferably dimethylformamide. The reaction is carried out at a temperature of about −20° to 25° C., preferably about 0° C., for about 2 to 12 hours, preferably about 6 hours. When the reaction is substantially complete, the product of formula (8), is isolated and purified by conventional means, preferably chromatography.

The next step is concerned with the removal of the protecting group from the compound of formula (8) by standard conditions well known in the art. For example, when the protecting group is a silyl ether, acidic conditions are used. Removal of the preferred protecting group is accomplished by treatment with fluoride ions. Typically, the compound of formula (8) is dissolved in a solvent such as tetrahydrofuran, chloroform or preferably acetonitrile and treated with a large excess of fluoride ions, for example as tetra-n-butylammonium fluoride or preferably aqueous hydrofluoric acid. The reaction is carried out at a temperature of about 0° to 50° C., preferably about 25° C., for about 5 minutes to 2 hours, preferably about 30 minutes. When the reaction is substantially complete, the product of formula (I), is isolated and purified by conventional means, preferably chromatography.

(B) Where X is $-CH_2CH_2-$ and m is 3

The preparation of the compounds of formula (I) where X is $-CH_2CH_2-$ and m is 3 is illustrated in Reaction Scheme IV.

REACTION SCHEME IV

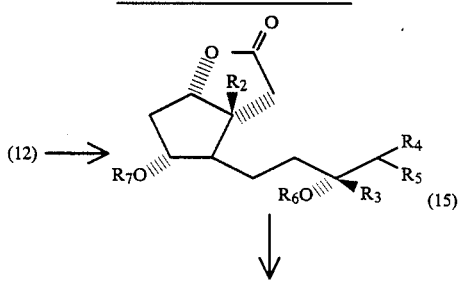

-continued
REACTION SCHEME IV

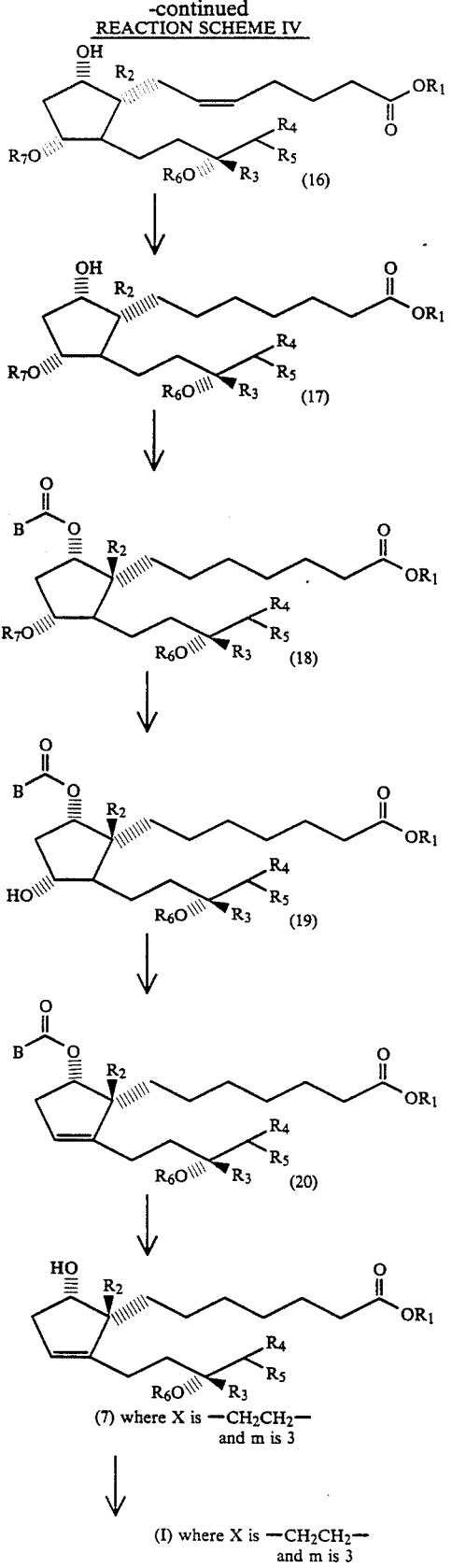

(7) where X is —CH$_2$CH$_2$—
and m is 3

(I) where X is —CH$_2$CH$_2$—
and m is 3

The preparation of the compounds of formula (I) where X is —CH$_2$CH$_2$— and m is 3 starts from the compound of formula (12), which may be prepared, for example, as shown in Reaction Scheme II. The compound of formula (12) is first protected with an acid-labile/base-stable protecting group (R$_7$), for example tetrahydropyranyl, tetrahydrofuranyl or 2-ethoxyethyl. Ether formation with any of these groups is generally carried out in an aprotic solvent such as a halogenated hydrocarbon with an acid catalyst using amounts and conditions well known in the art. Most preferably, the ether-forming reagent will be dihydropyran, using at least about 2.1 equivalents, the reaction being carried out in methylene chloride in the presence of p-toluenesulfonic acid. The reaction is generally carried out at between 20°-50° C., preferably at ambient temperature over a period of 15 minutes to two hours, preferably about 30 minutes. When the reaction is substantially complete, the product of formula (15) is isolated and purified by conventional means, preferably chromatography.

The compound of formula (15) is then converted to the compound of formula (16) by the same method shown in Reaction Scheme III for the conversion of the compound of formula (6) to (7), that is reaction of (15) first with a hindered reducing agent, preferably diisobutylaluminum hydride, followed by reaction of the aldehyde thus formed with a phosphorus ylide or similar reagent. When the reaction is substantially complete, the product of formula (16) is isolated and purified by conventional means, preferably chromatography.

The compound of formula (16) is then hydrogenated to the compound of formula (17) in a solvent inert to catalytic hydrogenation, such as methanol, ethyl acetate, tetrahydrofuran or preferably ethanol. This solution is added to a prehydrogenated suspension of a catalyst such as Raney-Nickel, platinum or preferably palladium in a protic solvent, preferably ethanol, and hydrogenated at a pressure of about 1-5 atmospheres, preferably about 1 atmosphere, of hydrogen until about 1 molar equivalent of hydrogen is absorbed. The reaction is carried out at a temperature of about 0°-50° C., preferably about 25° C., for about 5-48 hours, preferably about 20 hours. When the reaction is substantially complete, the product of formula (17) is isolated and purified by conventional means, preferably chromatography.

The 9-hydroxy group is then protected as the 4-biphenylcarboxylic acid ester derivative to give the compound of formula (18). Typically, the compound of formula (17) is dissolved in an inert solvent such as benzene, toluene, acetonitrile, diethyl ether, chloroform, tetrahydrofuran or preferably methylene chloride and reacted with from 1 to 6 molar equivalents, preferably about 2.5 molar equivalents, of 4-biphenylcarbonyl chloride in the presence of about 1 to 5 molar equivalents, preferably about 3 molar equivalents, of 4-dimethylaminopyridine. The reaction is carried out at a temperature of about 0°-40° C., preferably about 25°, for about 1-6 hours, preferably about 1 hour. When the reaction is substantially complete, the product of formula (18) is isolated and purified by conventional means, preferably chromatography.

The tetrahydropyranyl protecting group is then removed by methods well known in the art, i.e. mild acid treatment. Preferably, the compound of formula (18) is dissolved in ethereal solvent, preferably diethylether, and about 1 to 6 molar equivalents, preferably about 3 molar equivalents, of magnesium bromide etherate added. The reaction is carried out at a temperature of about 0°–40° C., preferably about 25°, for about 1–6 hours, preferably about 2 hours. When the reaction is substantially complete, the product of formula (19) is isolated and purified by conventional means, preferably chromatography.

The compound of formula (19) is then dehydrated to give the cyclopentene of formula (20), by the method described above in Reaction Scheme II for the conversion of the compound of formula (12) to (6), using a dehydrating agent, preferably trifluoromethanesulfonic anhydride in the presence of a base, preferably 2,4,6-collidine. When the reaction is substantially complete, the product of formula (20) is isolated and purified by conventional means, preferably chromatography.

The remaining steps then follow those previously described, i.e. hydrolysis of the biphenyl ester of formula (20), as described in Reaction Scheme II above, with a mild base, preferably potassium carbonate, to give a compound of formula (7) (illustrated in Reaction Scheme III) where X is —CH$_2$CH$_2$— and m is 3. The compound of formula (7) is then converted to the compound of formula (I) where X is —CH$_2$CH$_2$— and m is 3 using the same procedures as disclosed in Reaction Scheme III. That is, oxidation of the 9-hydroxy group to the 9-ketone followed by deprotection of the 15-hydroxy group to give the compound of formula (I).

(c) Where X is —CH$_2$CH=C=CH— and m is 1

The preparation of the compounds of formula (I) where X is —CH$_2$CH=C=CH— and m is 1 is illustrated in Reaction Scheme V.

REACTION SCHEME V

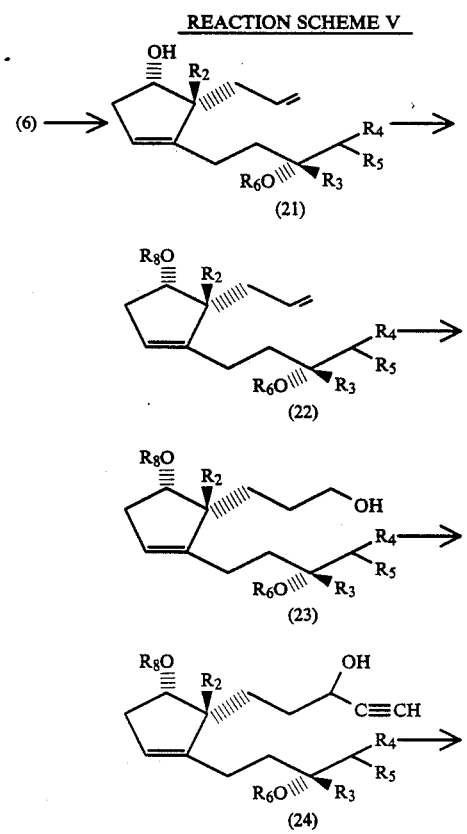

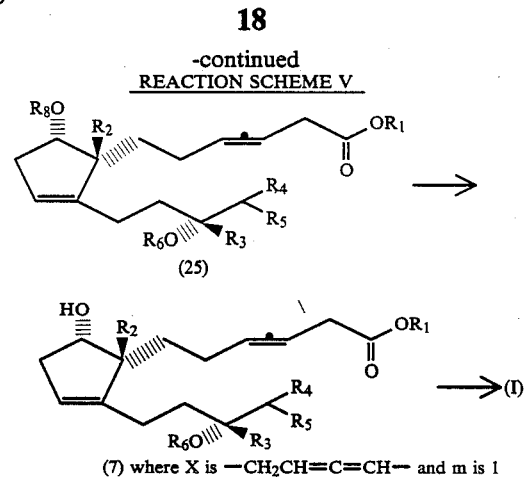

(7) where X is —CH$_2$CH=C=CH— and m is 1

The preparation of the compounds of formula (I) where X is —CH$_2$CH=C=CH— and m is 1 starts from the compound of formula (6), which may be prepared, for example, as shown in Reaction Scheme I or II. The compound of formula (6) is first dissolved in an inert solvent, for example diethylether, benzene, hexane, tetrahydrofuran or preferably toluene. The solution is cooled to a temperature of about −50° C. to −100° C., preferably about −80° C., and about 1 to 3 molar equivalents, preferably about 1.5 molar equivalents, of a hindered reducing agent, preferably diisobutylaluminum hydride. After about 10 minutes to 2 hours, preferably about 30 minutes, any excess reducing agent remaining is reacted with a protic solvent such as ethanol or preferably methanol and allowed to warm to about room temperature. The mixture is diluted and filtered through Celite, and the solvent removed from the filtrate under reduced pressure.

The residue is then dissolved in an aprotic solvent such as diethyl ether, dimethyl sulfoxide or preferably tetrahydrofuran and reacted with about 1 to 2 molar equivalents, preferably about 1.1 molar equivalents, of methylidenetriphenylphosphorane. The reaction is carried out at a temperature of about 0°–40° C., preferably about 25°, for about 10 minutes to 4 hours, preferably about 30 minutes. When the reaction is substantially complete, the product of formula (21) is isolated and purified by conventional means, preferably chromatography.

The 9-hydroxy group of the compound of formula (21) is then protected with a protecting group (R$_8$) that is stable to base, but that may subsequently be removed while leaving the protecting group (R$_6$) on the 15-hydroxy group intact, for example tetrahydropyranyl or preferably a silyl ether, for example trimethylsilyl ether or most preferably triethylsilyl ether. When a silylating agent is employed, standard conditions normally used for such a reagent are used. For example, the reaction is generally carried out in a polar aprotic solvent, preferably N,N-dimethylformamide, with an excess of the silylating reagent, 2.2 to 4 equivalents, and a greater excess relative to the silylating reagent of a mild base such as imidazole.

Preferably, the imidazole and about 3 equivalents of triethylsilyl chloride is added to a dry dimethylformamide solution of the hydroxy compound and stirred overnight at about room temperature, completion of the reaction being confirmed by tlc. When the reaction is substantially complete, the product of formula (22) is isolated and purified by conventional means, preferably chromatography.

The compound of formula (22) is then hydroxylated to the compound of formula (23). Typically, a solution of about 1 to 4 molar equivalents, preferably about 2 molar equivalents, of 9-borabicyclo[3.3.1]nonane in an ethereal solvent such as diethylether, dimethoxymethane or preferably tetrahydrofuran is added to a solution of the compound of formula (22) in the same solvent. The reaction is carried out at a temperature of about 0°–40° C., preferably about 25°, for about 10 minutes to 4 hours, preferably about 40 minutes. An aqueous solution of about 2 to 20 molar equivalents, preferably about 9 molar equivalents, of a strong base, preferably sodium hydroxide, is then added, followed by about 10 to 50 molar equivalents, preferably about 25 molar equivalents, of 30% hydrogen peroxide, keeping the temperature at about 0°–30° C., preferably about 25°, for about 10 minutes to 1 hour, preferably about 30 minutes. When the reaction is substantially complete, the product of formula (23) is isolated and purified by conventional means, preferably chromatography.

The alcohol of formula (23) is then oxidized conventionally to an aldehyde, which is in turn reacted (with no purification) with ethynyl anion to give the compound of formula (24). The oxidizing agent is, for example, pyridiniun chlorochromate, or preferably oxalyl chloride/dimethyl sulfoxide. Typically, about 3 to 10 molar equivalents, preferably about 5 molar equivalents, of dimethyl sulfoxide is added slowly to about 2 to 10 molar equivalents, preferably about 4 molar equivalents, of oxalyl chloride in an inert solvent as defined above, preferably dichloromethane, keeping the temperature at about $-75°$ C., over a period of about 10 minutes to 1 hour, preferably about 30 minutes. A solution of the compound of formula (23) in the same solvent is then added, keeping the solution at about $-60°$ to $-100°$ C., preferably about $-75°$ C., and reacted for about 10 minutes to 1 hour, preferably about 30 minutes. About 4 to 20 molar equivalents, preferably about 8 molar equivalents, of a tertiary organic base, preferably triethylamine, is then added and the reaction continued, keeping the solution at about $-60°$ to $-100°$ C., preferably about $-75°$ C. for about 10 minutes to 3 hours, preferably about 1 hour. The aldehyde thus formed is isolated conventionally and dissolved in an ethereal solvent, preferably tetrahydrofuran. To this solution is added about 1 to 10 molar equivalents, preferably about 3 molar equivalents, of a solution of ethynyl anion such as ethynyllithium, ethynylsodium or preferably ethynylmagnesium chloride, in an ethereal solvent, preferably tetrahydrofuran. The reaction is carried out at a temperature of about $-10°$ to 20° C., preferably about 5°, for about 10 minutes. When the reaction is substantially complete, the epimeric mixture of alkynols of formula (24) may be separated into the individual enantiomers by conventional means, for example chromatography, or preferably the next reaction is carried out with no further purification.

The compound of formula (24) is then converted to the allene of formula (25) by methods well known in the art, preferably a Claisen type rearrangement. For example, the alkynols of formula (24) are dissolved in an inert solvent as defined above, or toluene or preferably xylene and about 4 to 40 molar equivalents, preferably about 15 molar equivalents, of a trialkyl orthoacetate, preferably trimethylorthoacetate, containing a catalytic amount of about 5% of a low molecular weight alkanoic acid, preferably propionic acid, is added. The reaction is carried out at a temperature of about 70° to 150° C., preferably about 110°, for about 1–18 hours, preferably about 5 hours. When the reaction is substantially complete, the compound of formula (25) is isolated and purified by conventional means, preferably chromatography.

The $R_8$ protecting group, preferably triethylsilyl, is then removed in a manner that leaves the $R_6$ protecting group intact. Typically, the compound of formula (25) is dissolved in an aqueous solvent containing a weak acid, for example tetrahydrofuran/acetic/water acid (8:8:1), and reacted for about 6 to 48 hours, preferably about 18 hours. When the reaction is substantially complete, the compound of formula (7) where X is $-CH_2CH=C=CH-$ and m is 1 is isolated and purified by conventional means, preferably chromatography.

The remaining steps then follow those previously described in Reaction Scheme III for the conversion of the compound of formula (7) to the compound of formula (I). That is, oxidation of the 9-hydroxy group to the 9-ketone followed by deprotection of the 15-hydroxy group to give the compound of formula (I) where X is $-CH_2CH=C=CH-$ and m is 1.

PREPARATION OF THE COMPOUNDS OF FORMULA (I) WHERE $R_1$ IS HYDROGEN

The compounds of formula (I) where $R_1$ is hydrogen may be prepared from the compounds of formula (I) where $R_1$ is lower alkyl, preferably where $R_1$ is methyl, by hydrolysis.

The compounds of formula (I) where $R_1$ is hydrogen and $R_2$ is lower alkyl may be prepared by conventional hydrolysis procedures, for example using sodium hydroxide, sodium bicarbonate or preferably potassium carbonate as a base. The reaction is preferably conducted in an aqueous solvent, for example aqueous dimethylformamide, acetone or preferably a lower alcohol, most preferably methanol, at a temperature from about 0°–40° C., preferably about 25° C.

However, the compounds of formula (I) where $R_1$ and $R_2$ are both hydrogen are sensitive to the above hydrolysis conditions, as they have a tendency to convert to PGBs under basic conditions. Thus a mild hydrolysis procedure is necessary, for example the enzymatic hydrolysis procedure set forth in *J. Am. Chem. Soc.*, Vol 101, 4319 (1979). The details of such a hydrolysis are given in detail in Example 2 of the preparations.

STARTING MATERIALS

The compound of formula (1) where $R_2$ is hydrogen, used as a starting material in Reaction Scheme I, is well known in the synthetic art, for example see *Tetrahedron Lett.*, 3275 (1976) The preparation of the compound of formula (1) where $R_2$ is methyl is described in, for example, *Tetrahedron*, Vol. 38, pp 1261–1268 (1982). The compound of formula (9) used as a starting material in Reaction Scheme II is also well known. The synthesis of such lactones is reported for example in *Prostaglandins*, Vol. 6, 87 (1974), *J.A.C.S.*, Vol. 88, 5654 (1966), *J.A.C.S.*, Vol. 91, 5675 (1969), *J.A.C.S.*, Vol. 92, 397 (1970), U.S. Pat. Nos. 3,880,712, 3,985,791 and 4,304,907, the relevant portions of which are hereby incorporated by reference. The compounds of formula (9) are prepared from the compounds of formula (14), the preparation of which is illustrated in Reaction Scheme VI below.

REACTION SCHEME VI

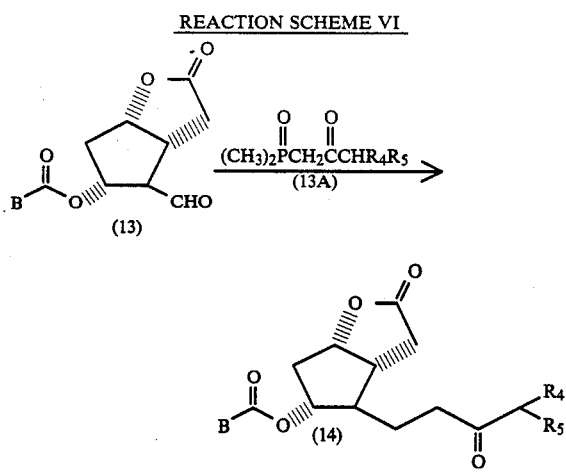

where $R_4$, $R_5$ and B are as defined above.

For example, to prepare the compound of formula (9) where $R_4$ is hydrogen and $R_5$ is phenoxy, the compound of formula (13) is first reacted with the anion of dimethyl 2-oxo-3-phenoxypropylphosphonate (13A). The substituted dimethylphosphonate of formula (13A) is prepared from the reaction of an ester (e.g. ethyl phenoxyacetate) or an acid halide (e.g. phenoxyacetyl chloride) with the anion of dimethyl methylphosphonate. Any compound of formula (13A) may be made using the above procedure by reacting the appropriate ester or acid halide (incorporating the desired definition of $R_4$ and $R_5$) with the anion of dimethyl methylphosphonate. Consequently any compound of formula (14) may be prepared from the compound of formula (13).

To prepare the compound of formula (9) where $R_3$ is hydrogen the compound of formula (14) is then reduced with, for example, sodium borohydride, zinc borohydride or aluminum isopropoxide. To prepare the compound of formula (9) where $R_3$ is lower alkyl the compound of formula (14) is reacted with an organometallic compound of formula $R_3M$, where M is an alkali metal, or preferably a Grignard reagent of formula $R_3MgY$, where Y is a halide, as detailed in Reaction Scheme I above. The mixture of 15α- and 15β-epimers of the compound of formula (9) can then be separated from each other at this stage by conventional means, for example thin layer chromatography or high-pressure liquid chromatography.

UTILITY AND ADMINISTRATION

The compounds of the present invention exhibit prostaglandin-like biological activities, and are thus used in the treatment of mammals where the use of prostaglandins is indicated. The compounds of formula (I) are particularly useful as hypotensive agents to reduce blood pressure in mammals, including man. The compounds are preferably administered parenterally.

The novel PGC compounds of formula (I) are also useful in mammals, including man, for reducing and controlling excessive gastric acid secretion, thereby reducing or avoiding gastrointestinal and duodenal ulcer formation, and accelerating the healing of such ulcers already present in the gastrointestinal and duodenal tracts. The compounds are preferably administered parenterally.

Other physiological activities of the novel PGC compounds of formula (I) include, for example, inhibition of platelet aggregation, controlling cases of renal disfunction, bronchodilation, inducing labor in pregnant mammals, controlling the reproductive cycle in ovulating mammals, and prevention and cure of diseases involving abnormal lipid mobilization and high free fatty acid levels, e.g., diabetes mellitus, vascular diseases, and hyperthyroidism.

In applying the compounds of this invention to treatment of the above conditions, any pharmaceutically acceptable mode of administration can be used, either alone or in combination with other pharmaceutically acceptable excipients, including solid, semi-solid liquid or aerosol dosage forms, such as, for example, tablets, pills, capsules, powders, liquids, suspensions, aerosols or the like, preferably in unit dosage forms suitable for single administration of precise dosages, or in sustained or controlled release dosage forms for the prolonged administration of the compound at a predetermined rate. The compositions will typically include a conventional pharmaceutical carrier or excipient and an active compound of formula (I) or the pharmaceutically acceptable salts thereof and, in addition, may include other medicinal agents, pharmaceutical agents, carriers, adjuvants, etc.

The amount of active compound administered will, of course, be dependent on the subject and disease state being treated, the severity of the affliction, the manner of administration and the judgment of the prescribing physician. However, an effective dosage is in the range of 0.001 µg to about 100 µg/kg of body weight, preferably about 1.0 µg to 50 µg/kg.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. Liquid pharmaceutically administerably compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s) in an amount effective to alleviate the symptoms of the subject being treated.

Dosage forms or compositions containing active ingredient (compounds of formula (I) or its salts) in the range of 0.1 to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 0.01%–95% active ingredient, preferably 0.1–50%.

Particularly preferred oral formulations of the compounds of formula (I) are formulations in which the compound is dissolved in a propylene glycol diester of a short-chain fatty acid or in a cyclic carbonate diester, such as propylene carbonate. For a solid dosage form, the solution, e.g. in propylene carbonate, is preferably encapsulated in a soft-shelled gelatine capsule. Such diester solutions, and the preparation and encapsulation thereof, are disclosed in U.S. Pat. Nos. 4,328,245; 4,409,239; and 4,410,545. For a liquid dosage form, the solution, e.g. in propylene carbonate, may be diluted with a sufficient quantity of a pharmaceutically-acceptable liquid carrier, e.g. water, to be easily measured for administration.

Other useful formulations include those set forth in U.S. Pat. Nos. Re. 28,819 and 4,358,603.

The formulation can be administered in a single unit dosage form for continuous treatment or in a single unit dosage form ad libitum when relief of symptoms is specifically required.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parental compositions is highly dependent on the specific nature thereof, as well as the activity of the compound and the needs of the subject. However, percentages of active ingredient of 0.01% to 10% in solution are employable, and will be higher if the composition is a solid which will be subsequently diluted to the above percentages. Preferably the composition will comprise 0.2–2% of the active agent in solution.

For all of the above purposes, the novel formula I compounds are used in free acid form, as esters, or in pharmaceutically acceptable salt form.

PREPARATION 1

Preparation of [3-chloromethyl-1-hydroxy cyclopentene-3-en-2-yl]acetic acid, Y-lactone, the compound of formula (2)

A. To a solution of [3-hydroxymethyl-1-hydroxycyclopent-3-en-2-yl]acetic acid, Y-lactone, the compound of formula (1), (188 mg, 1.22 mmol) in 10 ml of methylene chloride was added 4-dimethylaminopyridine (119 mg, 0.97 mmol), followed by p-toluenesulfonyl chloride (280 mg, 1.46 mmol) and triethylamine (123 mg, 1.22 mmol). After stirring for 2 hours at room temperature, the mixture was diluted with diethyl ether (80 ml), filtered and the filtrate washed successively with aqueous 10% copper sulfate (50 ml), 10% aqueous sodium bicarbonate (50 ml) and saturated brine (50 ml). The organic layer was dried over anhydrous magnesium sulfate and the solvent removed under reduced pressure. The residue was purified by column chromatography (silica gel, hexane/ethyl acetate, 70/30) to give 165 mg of [3-chloromethyl-1-hydroxycyclopent-3-en-2-yl]acetic acid, Y-lactone, m.p. 33°–34° C., the compound of formula (2).

B. Similarly, replacing [3-hydroxymethyl-1-hydroxycyclopent-3-en-2-yl]acetic acid, Y-lactone with [(1S,2R)-3-hydroxymethyl-1-hydroxy-2-methylcyclopent-3-en-2-yl]acetic acid, Y-lactone, and carrying out the procedures of 1A above, [(1S,2R)-3-chloromethyl-1-hydroxy-2-methylcyclopent-3-en-2-yl]acetic acid was prepared, $[\alpha]_D = +39.1°$ (C=1.023, CHCl$_3$).

PREPARATION 2

Preparation of 1-phenylsulfonyl-2-oxo-3-phenoxypropane and Related Compounds of Formula (2a)

A. n-Butyllithium (8.5 ml, 1.6M in hexane) was added at −72° C. to a solution of methylphenyl sulfone (2.14 g, 13.7 mmol) in 80 ml of tetrahydrofuran. The reaction mixture was then allowed to warm slowly to −20° C. and maintained at this temperature for 25 minutes. It was then recooled to −72° C. and ethyl phenoxyacetate (1.48 g, 8.22 mmol) was added dropwise. The cooling bath was removed, the mixture was stirred at 20° C. for 14 hrs. and then poured into 100 ml of saturated NH$_4$Cl and extracted with diethyl ether. The combined organic extracts were washed with brine, dried over anhydrous magnesium sulfate and the solvent removed under reduced pressure. The crude residue was purified by column chromatography (silica gel, methylene chloride) giving 1-phenylsulfonyl-2-oxo-3-phenoxypropane, the compound of formula (2a), 800 mg.

B. Similarly, following the procedure of A above and substituting the appropriate ester in place of ethyl phenoxyacetate, the following compounds of formula (2a) were prepared.

1-phenylsulfonyl-2-oxo-2-cyclohexylethane; and
1-phenylsulfonyl-2-oxoheptane.

C. Similarly, following the procedure of A above and substituting the appropriate ester in place of ethyl phenoxyacetate, the following compounds of formula (2a) are prepared.

1-phenylsulfonyl-2-oxo-3-phenylpropane;
1-phenylsulfonyl-2-oxo-3-methyloctane;
1-phenylsulfonyl-2-oxoundecane;
1-phenylsulfonyl-2-oxo-7,7,7-trifluoroheptane;
1-phenylsulfonyl-2-oxo-3-cyclopentylpropane;
1-phenylsulfonyl-2-oxo-3-methyl-3-phenoxypropane; and
1-phenylsulfonyl-2-oxo-3-methylheptane.

PREPARATION 3

Preparation of [3-(2'-phenylsulfonyl-3'-oxo-4'-phenoxybut-1'-yl)-1-hydroxycyclopent-3-en-2-yl]acetic acid, Y-lactone and Related Compounds of Formula (3)

A. A mixture of [3-chloromethyl-1-hydroxy-cyclopent-3-en-2-yl]acetic acid, Y-lactone, the compound of formula (2), (2.89 g, 16.8 mmol), 1-phenylsulfonyl-2-oxo-3-phenoxypropane, the compound of formula (2a), (5.69 g, 20 mmol), prepared as shown in 2a above, and anhydrous potassium carbonate (2.3 g, 16.8 mmol) in 50 ml of N,N-dimethylformamide was stirred at 35° C. for 4 hours and at 50° C. for 1 hour. It was then poured into ice-cold 10% hydrochloric acid (50 ml), the phases separated and the aqueous layer extracted with diethyl ether (3×30 ml). The combined organic extracts were washed with brine, dried over anhydrous magnesium sulfate and the solvent removed under reduced pressure. The residue was purified by column chromatography (silica gel hexane/ethyl acetate, 60/40) giving [3-(2'-phenylsulfonyl-3'-oxo-4'-phenoxybut-1'-yl)-1-hydroxycyclopent-3-en-2-yl]acetic acid, Y-lactone, the compound of formula (3), 5.26 g.

B. Similarly, replacing [3-chloromethyl-1-hydroxycyclopent-3-en-2-yl]acetic acid, Y-lactone with [(1S,2R)-3-chloromethyl-1-hydroxy-2-methylcyclopent-3-en-2-yl]acetic acid, Y-lactone and following the procedure of A above (except that the reaction mixture is stirred for three days at room temperature), the following compound of formula (3) was prepared:
[(1S,2R)-3-(2'-phenylsulfonyl-3'-oxo-4'-phenoxybut-1'-yl)-1-hydroxy-2-methylcyclopent-3-en-2-yl]acetic acid, Y-lactone, $[\alpha]_D = +12.7°$ (C=1.03, CHCl$_3$).

C. Similarly, following the procedure of A above and replacing 1-phenylsulfonyl-3-oxo-4-phenoxybutane with the appropriate compounds of formula (2a), the following representative compounds of formula (3) were prepared:
[3-(2'-phenylsulfonyl-3'-oxo-3'-cyclohexylprop-1'-yl)-1-hydroxycyclopent-3-en-2-yl]acetic acid, Y-lactone; and
[3-(2'-phenylsulfonyl-3'-oxooct-1'-yl)-1-hydroxycyclopent-3-en-2-yl]acetic acid, Y-lactone.

D. Similarly, following the procedure of A or B above and replacing 1-phenylsulfonyl-3-oxo-4-phenoxybutane with the appropriate compounds of formula (2a), the following representative compounds of formula (3) are prepared:
[3-(2'-phenylsulfonyl-3'-oxo-4'-phenylbut-1'-yl)-1-hydroxycyclopent-3-en-2-yl]acetic acid, Y-lactone;
[3-(2'-phenylsulfonyl-3'-oxo-4'-methylnon-1'-yl)-1-hydroxycyclopent-3-en-2-yl]acetic acid, Y-lactone;
[3-(2'-phenylsulfonyl-3'-oxododec-1'-yl)-1-hydroxycyclopent-3-en-2-yl]acetic acid, Y-lactone;
[3-(2'-phenylsulfonyl-3'-oxo-8',8',8'-trifluorooct-1'-yl)-1-hydroxycyclopent-3-en-2-yl]acetic acid, Y-lactone;
[3-(2'-phenylsulfonyl-3'-oxo-3'-cyclopentylprop-1'-yl)-1-hydroxycyclopent-3-en-2-yl]acetic acid, Y-lactone;
[3-(2'-phenylsulfonyl-3'-oxo-4'-methyl-4'-phenoxybut-1'-yl)-1-hydroxycyclopent-3-en-2-yl]acetic acid, Y-lactone;
[3-(2'-phenylsulfonyl-3'-oxo-4'-methyl-4'-oct-1'-yl)-1-hydroxycyclopent-3 -en-2-yl]acetic acid, Y-lactone;
[(1S,2R)-3-(2'-phenylsulfonyl-3'-oxo-3'-cyclohexylprop-1'-yl)-1-hydroxy-2-methylcyclopent-3-en-2-yl]acetic acid, Y-lactone; and
[(1S,2R)-3-(2'phenylsulfonyl-3'-oxooct-1'-yl)-1-hydroxy-2-methylcyclopent-3-en-2-yl]acetic acid, Y-lactone.

PREPARATION 4

Preparation of [3-(3'-oxo-4'-phenoxybut-1'-yl)-1-hydroxycyclopent-3-en-2-yl]-acetic acid, Y-lactone and Related Compounds of Formula (4)

A. (a) A mixture of [3-(2'-phenylsulfonyl-3'-oxo-4'-phenoxybut-1'-yl)-1-hydroxycyclopent-3-en-2-yl]acetic acid, Y-lactone, the compound of formula (3), (2.915 g, 6.83 mmol) and zinc powder (8.94 g, 137 mmol) in 25 ml of acetic acid was refluxed for 10 min. Tetrahydrofuran (100 ml) was then added, the mixture filtered and the solid washed with diethyl ether (2×100 ml). The combined organic washings were extracted with 5% aqueous sodium bicarbonate solution (100 ml), washed with brine, dried over anhydrous magnesium sulfate and the solvent removed under reduced pressure. The residue was purified by column chromatography (silica gel, hexane/ethyl acetate, 60/40), giving [3-(3'-oxo-4'-phenoxybut-1'-yl)-1-hydroxy-cyclopent-3-en-2-yl]acetic acid, Y-lactone, the compound of formula (4) 1.130 g.

(b) In the preparation above, aluminum/mercury amalgam in tetrahydrofuran/water solution may be used in place of zinc/acetic acid as a reducing agent to remove the phenylsulfonyl group.

B. Similarly, replacing [3-(2'-phenylsulfonyl-3'-oxo-4'-phenoxybut-1'-yl)-1-hydroxycyclopent-3-en-2-yl]acetic acid, Y-lactone with [(1S,2R)-3-(2'-phenylsulfonyl-3'-oxo-4'-phenoxybut-1'-yl)-1-hydroxy-2-methylcyclopent-3-en-2-yl]acetic acid, Y-lactone and following the procedure of A above, the following compound of formula (4) was prepared:
[(1S,2R)-3-(3'-oxo-4'-phenoxybut-1'-yl)-1-hydroxy-2-methylcyclopent-3-en-2-yl]acetic acid, Y-lactone.

C. Similarly, following the procedure of A above and replacing [3-(2'-phenylsulfonyl-3'-oxo-4'-phenoxybut-1'-yl)-1-hydroxycyclopent-3-en-2-yl]acetic acid, Y-lactone with the appropriate compounds of formula (3), the following representative compounds of formula (4) were prepared:
[3-(3'-oxo-3'-cyclohexylprop-1'-yl)-1-hydroxycyclopent-3-en-2-yl]acetic acid, Y-lactone; and
[3-(3'-oxooct-1'-yl)-1-hydroxycyclopent-3-en-2-yl]acetic acid, Y-lactone.

D. Similarly, following the procedure of A above and replacing 3-[2-(phenylsulfonyl)-3-oxo-4-phenoxybut-1-yl)-1α-hydroxy-3-cyclopentene-2α-acetic acid Y-lactone with the appropriate compounds of formula (3), the following representative compounds of formula (4) are prepared:
[3-(3'-oxo-4'-phenylbut-1'-yl)-1-hydroxycyclopent-3-en-2-yl]acetic acid, Y-lactone;
[3-(3'-oxo-4'-methylnon-1'-yl)-1-hydroxycyclopent-3-en-2-yl]acetic acid, Y-lactone;
[3-(3'-oxododec-1'-yl)-1-hydroxycyclopent-3-en-2-yl]acetic acid, Y-lactone;
[3-(3'-oxo-8',8',8'-trifluorooct-1'-yl)-1-hydroxycyclopent-3-en-2-yl]acetic acid, Y-lactone;
[3-(3'-oxo-3'-cyclopentylprop-1'-yl)-1-hydroxycyclopent-3-en-2-yl]acetic acid, Y-lactone;
[3-(3'-oxo-4'-methyl-4'-phenoxybut-1'-yl)-1-hydroxycyclopent-3-en-2-yl]acetic acid, Y-lactone;
[3-(3'-oxo-4'-methyloct-1'-yl)-1-hydroxycyclopent-3-en-2-yl]acetic acid, Y-lactone;
[(1S,2R)-3-(3'-oxo-3'-cyclohexylprop-1'-yl)-1-hydroxy-2-methylcyclopent-3-en-2-yl]acetic acid, Y-lactone; and
[(1S,2R)-3-(3'-oxooct-1'-yl)-1-hydroxy-2-methylcyclopent-3-en-2-yl]acetic acid, Y-lactone.

PREPARATION 5

Preparation of
(±)-[3-(3'-hydroxy-4'-phenoxybut-1'-yl)-1-hydroxycyclopent-3-en-2-yl]acetic acid, Y-lactone and Related Compounds of Formula (5)

A. Where $R_3$ is Hydrogen

Sodium borohydride (149 mg, 3.94 mmol) was added to a solution of [3-(3'-oxo-4'-phenoxybut-1'-yl)-1-hydroxy-cyclopent-3-en-2-yl]acetic acid, Y-lactone, the compound of formula (4), (1.130 g, 3.95 mmol) in 10 ml of methanol at 0° C. After 5 min, solid ammonium chloride (1 g) was added, the methanol was the solvent removed under reduced pressure and the residue partitioned between water (10 ml) and ethyl acetate (10 ml). The organic phase was dried over anhydrous magnesium sulfate and the solvent removed under reduced pressure to give (±)-[3-(3'-hydroxy-4'-phenoxybut-1'-yl)-1-hydroxycyclopent-3-en-2-yl]acetic acid, Y-lactone, the compound of formula (5).

B. Where $R_3$ is lower alkyl

A solution of 3 ml of 3M phenylmagnesium bromide in diethylether is added to a solution of 1.0 g of [3-(3'-oxo-4'-phenoxybut-1'-yl)-1-hydroxy-cyclopent-3-en-2-yl]acetic acid, Y-lactone, the compound of formula (4), (1.130 g, 3.95 mmol) in tetrahydrofuran at 0° C., the mixture stirred for 30 minutes at 0° C., then at 25° C. for 18 hours. The reaction is quenched with 10 ml of water and extracted with diethylether. The organic extract is washed with water, dried over anhydrous magnesium sulfate and the solvent removed under reduced pressure to give (±)-[3-(3'-hydroxy-3'-methyl-4'-phenoxybut-1'-yl)-1-hydroxycyclopent-3-en-2-yl]acetic acid, Y-lactone, the compound of formula (5).

C. Similarly, replacing [3-(3'-oxo-4'-phenoxybut-1'-yl)-1-hydroxycyclopent-3-en-2-yl]acetic acid, Y-lactone with [(1S,2R)-3-(3'-oxo-4'-phenoxybut-1'-yl)-1-hydroxy-2-methylcyclopent-3-en-2-yl]acetic acid, Y-lactone and following the procedure of A above, the following compound of formula (5) was prepared:
[(1S,2R,3'RS)-3-(3'-hydroxy-4'-phenoxybut-1'-yl)-1-hydroxy-2-methylcyclopent-3-en-2-yl]acetic acid, Y-lactone.

D. Similarly, following the procedure of A or B above and replacing [3-(3'-oxo-4'-phenoxybut-1'-yl)-1-hydroxycyclopent-3-en-2-yl]acetic acid, Y-lactone with the appropriate compounds of formula (4), the following representative compounds of formula (5) were prepared:
(±)-[3-(3'-hydroxy-3'-cyclohexylprop-1'-yl)-1-hydroxycyclopent-3-en-2-yl]acetic acid, Y-lactone; and
(±)-[3-(3'-hydroxyoct-1'-yl)-1-hydroxycyclopent-3-en-2-yl]acetic acid, Y-lactone.

E. Similarly, following the procedure of A or B above and replacing [3-(3'-oxo-4'-phenoxybut-1'-yl)-1-hydroxycyclopent-3-en-2-yl]acetic acid, Y-lactone with the appropriate compounds of formula (4), the following representative compounds of formula (5) are prepared:
(±)-[3-(3'-hydroxy-4'-phenylbut-1'-yl)-1-hydroxycyclopent-3-en-2-yl]acetic acid, Y-lactone;
(±)-[3-(3'-hydroxy-4'-methylnon-1'-yl)-1-hydroxycyclopent-3-en-2-yl]acetic acid, Y-lactone;
(±)-[3-(3'-hydroxydodec-1'-yl)-1-hydroxycyclopent-3-en-2-yl]acetic acid, Y-lactone;
(±)-[3-(3'-hydroxy-8',8',8'-trifluorooct-1'-yl)-1-hydroxycyclopent-3-en-2-yl]acetic acid, Y-lactone;
(±)-[3-(3'-hydroxy-3'-cyclopentylprop-1'-yl)-1-hydroxycyclopent-3-en-2-yl]acetic acid, Y-lactone;
(±)-[3-(3'-hydroxy-4'-methyl-4'-phenoxybut-1'-yl)-1-hydroxycyclopent-3-en-2-yl]acetic acid, Y-lactone;
(±)-[3-(3'-hydroxy-4'-methyloct-1'-yl)-1-hydroxycyclopent-3-en-2-yl]acetic acid, Y-lactone;
[(1S,2R,3'RS)-3-(3'-hydroxy-3'-cyclohexylprop-1'-yl)-1-hydroxy-2-methylcyclopent-3-en-2-yl]acetic acid, Y-lactone;
[(1S,2R,3'RS)-3-(3'-hydroxyoct-1'-yl)-1-hydroxy-2-methylcyclopent-3-en-2-yl]acetic acid, Y-lactone.
(±)-[3-(3'-hydroxy-3'-methyl-3'-cyclohexyl-prop-1'-yl)-1-hydroxycyclopent-3-en-2-yl]acetic acid, Y-lactone;
(±)-[3-(3'-hydroxy-3'-methyl-oct-1'-yl)-1-hydroxycyclopent-3-en-2-yl]acetic acid, Y-lactone; and
[(1S,2R,3'RS)-3-(3'-hydroxy-4'-phenoxybut-1'-yl)-1-hydroxy-2-n-butylcyclopent-3-en-2-yl]acetic acid, Y-lactone.

PREPARATION 6

Preparation of
[(±)-3-(3'-t-butyldimethylsilyloxy-4'-phenoxybut-1'-yl)-1-hydroxycyclopent-3-en-2-yl]acetic acid, Y-lactone and Related Compounds of Formula (6)

A. A solution of [3-(3'-hydroxy-4'-phenoxybut-1'-yl)-1-hydroxycyclopent-3-en-2-yl]acetic acid, Y-lactone (1.2 g) in 2 ml of N,N-dimethylformamide was stirred at room temperature, and imidazole (672 mg, 9.88 mmol) and t-butyldimethylsilyl chloride (714 mg, 4.74 mmol) were added successively. After 10 hrs, the mixture was poured into water (50 ml) and extracted with benzene (3×10 ml). The combined organic extracts were dried over anhydrous magnesium sulfate and the solvent removed under reduced pressure. The residue was purified by column chromatography (silica gel, hexane/ethyl acetate, 80/20) giving [(±)-3-(3'-t-butyldimethylsilyloxy-4'-phenoxybut-1'-yl)-1-hydroxycyclopent-3-en-2-yl]acetic acid, Y-lactone, the compound of formula (6), 1.437 g.

B. Similarly, replacing [(±)-3-(3'-hydroxy-4'-phenoxybut-1'-yl)-1-hydroxycyclopent-3-en-2-yl]acetic acid, Y-lactone with [(1S,2R,3RS)-3-(3'-hydroxy-4'-phenoxybut-1'-yl)-1-hydroxy-2-methylcyclopent-3-en-2-yl]acetic acid, Y-lactone and following the procedure of A above, the following compound of formula (5) was prepared:
[(1S,2R,3RS)-3-(3'-t-butyldimethylsilyloxy-4'-phenoxybut-1'-yl)-1-hydroxy-2-methylcyclopent-3-en-2-yl]acetic acid, Y-lactone.

C. Similarly, following the procedure of A above and replacing [(±)-3-(3'-hydroxy-4'-phenoxybut-1'-yl)-1-hydroxycyclopent-3-en-2-yl]acetic acid, Y-lactone with the appropriate compounds of formula (5), the following representative compounds of formula (6) were prepared:
[(±)-3-(3'-t-butyldimethylsilyloxy-3'-cyclohexylprop-1'-yl)-1-hydroxycyclopent-3-en-2-yl]acetic acid, Y-lactone; and
[(±)-3-(3'-t-butyldimethylsilyloxyoct-1'-yl)-1-hydroxycyclopent-3-en-2-yl]acetic acid, Y-lactone.

D. Similarly, following the procedure of A above and replacing [(±)-3-(3'-hydroxy-4'-phenoxybut-1'-yl)-1-hydroxycyclopent-3-en-2-yl]acetic acid, Y-lactone with the appropriate compounds of formula (5), the following representative compounds of formula (6) are prepared:

[(±)-3-(3'-t-butyldimethylsilyloxy-4'-phenylbut-1'-yl)-1-hydroxycyclopent-3-en-2-yl]acetic acid, Y-lactone;
[(±)-3-(3'-t-butyldimethylsilyloxy-4'-methylnon-1'-yl)-1-hydroxycyclopent-3-en-2-yl]acetic acid, Y-lactone;
[(±)-3-(3'-t-butyldimethylsilyloxydodec-1'-yl)-1-hydroxycyclopent-3-en-2-yl]acetic acid, Y-lactone;
[(±)-3-(3'-t-butyldimethylsilyloxy-8',8',8'-trifluorooct-1'-yl)-1-hydroxycyclopent-3-en-2-yl]acetic acid, Y-lactone;
[(±)-3-(3'-t-butyldimethylsilyloxy-3'-cyclopentylprop-1'-yl)-1-hydroxycyclopent-3-en-2-yl]acetic acid, Y-lactone;
[(±)-3-(3'-t-butyldimethylsilyloxy-4'-methyl-4'-phenoxybut-1'-yl)-1-hydroxycyclopent-3-en-2-yl]acetic acid, Y-lactone;
[(±)-3-(3'-t-butyldimethylsilyloxy-4'-methyl-4'-oct-1'-yl)-1-hydroxycyclopent-3-en-2-yl]acetic acid, Y-lactone;
[(1S,2R,3'RS)-3-(3'-t-butyldimethylsilyloxy-3'-cyclohexylprop-1'-yl)-1-hydroxy-2-methylcyclopent-3-en-2-yl]acetic acid, Y-lactone;
[(1S,2R,3'RS)-3-(3'-t-butyldimethylsilyloxyoct-1'-yl)-1-hydroxy-2-methylcyclopent-3-en-2-yl]acetic acid, Y-lactone.
[(±)-3-(3'-t-butyldimethylsilyloxy-3'-methyl-3'-cyclohexylprop-1'-yl)-1-hydroxycyclopent-3-en-2-yl]acetic acid, Y-lactone;
[(±)-3-(3'-t-butyldimethylsilyloxy-3'-methyl-oct-1'-yl)-1-hydroxycyclopent-3-en-2-yl]acetic acid, Y-lactone; and
[(1S,2R,3'RS)-3-(3'-t-butyldimethylsilyloxy-4'-phenoxybut-1'-yl)-1-hydroxy-2-n-butylcyclopent-3-en-2-yl]acetic acid, Y-lactone.

PREPARATION 7

Preparation of [(1S,2R,3R,4R,3'S)-4-(4''-biphenylcarbonyloxy)-3-(3'-hydroxy-4'-phenoxybut-1'-yl)-1-hydroxycyclopent-2-yl]acetic acid, Y-lactone and Related Compounds of Formula (10)

A. A solution of [(1S,2R,3S,4R,3'S)-4-(4''-biphenylcarbonyloxy)-3-(3'-hydroxy-4'-phenoxybut-(E)-enyl)-1-hydroxycyclopent-2-yl]acetic acid, Y-lactone, the compound of formula (9) (362 mg, 0.744 mmol), in 15 ml of ethyl acetate was added to a prehydrogenated suspension of Raney nickel catalyst (500 mg) in 15 ml of methanol. After hydrogenating for 18 hrs, the mixture was filtered through Celite, solvent removed from the filtrate under reduced pressure and the residue purified by column chromatography (silica gel, methylene chloride/acetone, 9/1) giving [(1S,2R,3R,4R,3'S)-4-(4''-biphenylcarbonyloxy)-3-(3'-hydroxy-4'-phenoxybut-1'-yl)-1-hydroxycyclopent-2-yl]acetic acid Y-lactone, the compound of formula (10), 323 mg.

B. Similarly, following the procedure of A above and replacing [(1S,2R,3S,4R,3'S)-4-(4''-biphenylcarbonyloxy)-3-(3'-hydroxy-4'-phenoxybut-(E)-enyl)-1-hydroxycyclopent-2-yl]acetic acid Y-lactone with [(1S,2R,3S,4R,3'R)-4-(4''-biphenylcarbonyloxy)-3-(3'-hydroxy-4'-phenoxybut-(E)-enyl)-1-hydroxycyclopent-2-yl]acetic acid Y-lactone, the following compound of formula (10) was prepared:
[(1S,2R,3R,4R,3'R)-4-(4''-biphenylcarbonyloxy)-3-(3'-hydroxy-4'-phenoxybut-1'-yl)-1-hydroxycyclopent-2-yl]acetic acid, Y-lactone.

C. Similarly, following the procedure of A above and replacing [(1S,2R,3S,4R,3''S)-4-(4''-biphenylcarbonyloxy)-3-(3'-hydroxy-4'-phenoxybut-(E)-enyl)-1-hydroxycyclopent-2-yl]acetic acid, Y-lactone with the appropriate compound of formula (9), the following representative compounds of formula (10) are prepared:
[(1S,2R,3R,4R,3'RS)-4-(4''-biphenylcarbonyloxy)-3-(3'-hydroxy-4'-phenoxybut-1'-yl)-1-hydroxycyclopent-2-yl]acetic acid, Y-lactone;
[(1S,2R,3S,4R,3'S)-4-(4''-biphenylcarbonyloxy)-3-(3'-hydroxy-3'-cyclohexylprop-1'-yl)-1-hydroxycyclopent-2-yl]-acetic acid, Y-lactone;
[(1S,2R,3S,4R,3'R)-4-(4''-biphenylcarbonyloxy)-3-(3'-hydroxy-3'-cyclohexylprop-1'-yl)-1-hydroxycyclopent-2-yl]-acetic acid, Y-lactone;
[(1S,2R,3S,4R,3'RS)-4-(4''-biphenylcarbonyloxy)-3-(3'-hydroxy-3'-cyclohexylprop-1'-yl)-1-hydroxycyclopent-2-yl]-acetic acid, Y-lactone;
[(1S,2R,3S,4R,3'S)-4-(4''-biphenylcarbonyloxy)-3-(3'-hydroxyoct-1'-yl)-1-hydroxycyclopent-2-yl]acetic acid, Y-lactone;
[(1S,2R,3S,4R,3'R)-4-(4''-biphenylcarbonyloxy)-3-(3'-hydroxyoct-1'-yl)-1-hydroxycyclopent-2-yl]acetic acid, Y-lactone;
[(1S,2R,3S,4R,3'RS)-4-(4''-biphenylcarbonyloxy)-3-(3'-hydroxyoct-1'-yl)-1-hydroxycyclopent-2-yl]acetic acid, Y-lactone;
[(1S,2R,3S,4R,3'S)-4-(4''-biphenylcarbonyloxy)-3-(3'-hydroxy-4'-methylnon-1'-yl)-1-hydroxycyclopent-2-yl]acetic acid, Y-lactone;
[(1S,2R,3S,4R,3'RS)-4-(4''-biphenylcarbonyloxy)-3-(3'-hydroxy-4'-methylnon-1'-yl)-1-hydroxycyclopent-2-yl]acetic acid, Y-lactone;
[(1S,2R,3S,4R,3'S)-4-(4''-biphenylcarbonyloxy)-3-(3'-hydroxy-4'-phenylbut-1'-yl)-1-hydroxycyclopent-2-yl]acetic acid, Y-lactone;
[(1S,2R,3S,4R,3'RS)-4-(4''-biphenylcarbonyloxy)-3-(3'-hydroxy-4'-phenylbut-1'-yl)-1-hydroxycyclopent-2-yl]acetic acid, Y-lactone;
[(1S,2R,3S,4R,3'S)-4-(4''-biphenylcarbonyloxy)-3-(3'-hydroxy-4'-cyclopentylprop-1'-yl)-1-hydroxycyclopent-2-yl]acetic acid, Y-lactone;
[(1S,2R,3S,4R,3'RS)-4-(4''-biphenylcarbonyloxy)-3-(3'-hydroxy-4'-cyclopentylprop-1'-yl)-1-hydroxycyclopent-2-yl]acetic acid, Y-lactone;
[(1S,2R,3S,4R,3'S)-4-(4''-biphenylcarbonyloxy)-3-(3'-hydroxy-4'-methyl-4'-phenoxybut-1'-yl)-1-hydroxycyclopent-2-yl]acetic acid, Y-lactone;
[(1S,2R,3S,4R,3'RS)-4-(4''-biphenylcarbonyloxy)-3-(3'-hydroxy-4'-methyl-4'-phenoxybut-1'-yl)-1-hydroxycyclopent-2-yl]acetic acid, Y-lactone;
[(1S,2R,3S,4R,3'S)-4-(4''-biphenylcarbonyloxy)-3-(3'-hydroxy-4'-methyloct-1'-yl)-1-hydroxycyclopent-2-yl]acetic acid, Y-lactone;
[(1S,2R,3S,4R,3'RS)-4-(4''-biphenylcarbonyloxy)-3-(3'-hydroxy-4'-methyloct-1'-yl)-1-hydroxycyclopent-2-yl]acetic acid, Y-lactone;
[(1S,2R,3S,4R,3'S)-4-(4''-biphenylcarbonyloxy)-3-(3'-hydroxy-3'-methyl-3'-cyclohexylprop-1'-yl)-1-hydroxycyclopent-2-yl]acetic acid, Y-lactone;
[(1S,2R,3S,4R,3'RS)-4-(4''-biphenylcarbonyloxy)-3-(3'-hydroxy-3'-methyl-3'-cyclohexylprop-1'-yl)-1-hydroxycyclopent-2-yl]acetic acid, Y-lactone;
[(1S,2R,3S,4R,3'S)-4-(4''-biphenylcarbonyloxy)-3-(3'-hydroxy-3'-methyloct-1'-yl)-1-hydroxycyclopent-2-yl]acetic acid, Y-lactone; and
[(1S,2R,3S,4R,3'RS)-4-(4''-biphenylcarbonyloxy)-3-(3'-hydroxy-3'-methyloct-1'-yl)-1-hydroxycyclopent-2-yl]acetic acid, Y-lactone.

PREPARATION 8

Preparation of
[(1S,2R,3R,4R,3'S)-4-(4"-biphenylcarbonyloxy)-3-(3'-t-butyldimethylsilyloxy-4'-phenoxybut-1'-yl)-1-hydroxycyclopent-2-yl]acetic acid, Y-lactone and Related Compounds of Formula (11)

A. Imidazole (1.26 g, 18.5 mmol) and t-butyldimethylchlorosilane (1.40 g, 9.2 mmol) were added to a solution of [(1S,2R,3R,4R,3'S)-4-(4"-biphenylcarbonyloxy)-3-(3'-hydroxy-4'-phenoxybut-1'-yl)-1-hydroxycyclopent-2-yl]acetic acid, Y-lactone, the compound of formula (10), (2.57 g, 5.29 mmol) in 16 ml of N,N-dimethylformamide and stirred at room temperature. After 3 hrs, the mixture was poured into 20 ml of water and extracted with benzene (5×20 ml). The combined organic extracts were washed with water (20 ml), dried over anhydrous magnesium sulfate and the solvent removed under reduced pressure, giving [(1S,2R,3R,4R,3'S)-4-(4"-biphenylcarbonyloxy)-3-(3'-t-butyldimethylsilyloxy-4'-phenoxybut-1'-yl)-1-hydroxycyclopent-2-yl]acetic acid, Y-lactone, the compound of formula (11). The product was used for the next step without purification. An analytical sample was obtained by recrystallization from hexane.

B. Similarly, following the procedure of A above and replacing [(1S,2R,3R,4R,3'S)-4-(4"-biphenylcarbonyloxy)-3-(3'-hydroxy-4'-phenoxybut-1'-yl)-1-hydroxycyclopent-2-yl]acetic acid, Y-lactone with [(1S,2R,3R,4R,3'R)-4-(4"-biphenylcarbonyloxy)-3-(3'-hydroxy-4'-phenoxybut-1'-yl)-1-hydroxycyclopent-2-yl]acetic acid, Y-lactone, the following compound of formula (11) was prepared:

[(1S,2R,3R,4R,3'R)-4-(4"-biphenylcarbonyloxy)-3-(3'-t-butyldimethylsilyloxy-4'-phenoxybut-1'-yl)-1-hydroxycyclopent-2-yl]acetic acid, Y-lactone.

C. Similarly, following the procedure of A above and replacing [(1S,2R,3R,4R,3'S)-4-(4"-biphenylcarbonyloxy)-3-(3'-hydroxy-4'-phenoxybut-1'-yl)-1-hydroxycyclopent-2-yl]acetic acid, Y-lactone with the appropriate compound of formula (10), the following representative compounds of formula (11) are prepared:

[(1S,2R,3R,4R,3'RS)-4-(4"-biphenylcarbonyloxy)-3-(3'-t-butyldimethylsilyloxy-4'-phenoxybut-1'-yl)-1-hydroxycyclopent-2-yl]acetic acid, Y-lactone;

[(1S,2R,3S,4R,3'S)-4-(4"-biphenylcarbonyloxy)-3-(3'-t-butyldimethylsilyloxy-3'-cyclohexylprop-1'-yl)-1-hydroxycyclopent-2-yl]acetic acid, Y-lactone;

[(1S,2R,3S,4R,3'R)-4-(4"-biphenylcarbonyloxy)-3-(3'-t-butyldimethylsilyloxy-3'-cyclohexylprop-1'-yl)-1-hydroxycyclopent-2-yl]acetic acid, Y-lactone;

[(1S,2R,3S,4R,3'RS)-4-(4"-biphenylcarbonyloxy)-3-(3'-t-butyldimethylsilyloxy-3'-cyclohexylprop-1'-yl)-1-hydroxycyclopent-2-yl]acetic acid, Y-lactone;

[(1S,2R,3S,4R,3'S)-4-(4"-biphenylcarbonyloxy)-3-(3'-t-butyldimethylsilyloxyoct-1'-yl)-1-hydroxycyclopent-2-yl]acetic acid, Y-lactone;

[(1S,2R,3S,4R,3'R)-4-(4"-biphenylcarbonyloxy)-3-(3'-t-butyldimethylsilyloxyoct-1'-yl)-1-hydroxycyclopent-2-yl]acetic acid, Y-lactone;

[(1S,2R,3S,4R,3'RS)-4-(4"-biphenylcarbonyloxy)-3-(3'-t-butyldimethylsilyloxyoct-1'-yl)-1-hydroxycyclopent-2-yl-acetic acid, Y-lactone;

[(1S,2R,3S,4R,3'S)-4-(4"-biphenylcarbonyloxy)-3-(3'-t-butyldimethylsilyloxy-4'-methylnon-1'-yl)-1-hydroxycyclopent-2-yl]acetic acid, Y-lactone;

[(1S,2R,3S,4R,3'RS)-4-(4"-biphenylcarbonyloxy)-3-(3'-t-butyldimethylsilyloxy-4'-methylnon-1'-yl)-1-hydroxycyclopent-2-yl]acetic acid, Y-lactone;

[(1S,2R,3S,4R,3'S)-4-(4"-biphenylcarbonyloxy)-3-(3'-t-butyldimethylsilyloxy-4'-phenylbut-1'-yl)-1-hydroxycyclopent-2-yl]acetic acid, Y-lactone;

[(1S,2R,3S,4R,3'RS)-4-(4"-biphenylcarbonyloxy)-3-(3'-t-butyldimethylsilyloxy-4'-phenylbut-1'-yl)-1-hydroxycyclopent-2-yl]acetic acid, Y-lactone;

[(1S,2R,3S,4R,3'S)-4-(4"-biphenylcarbonyloxy)-3-(3'-t-butyldimethylsilyloxy-4'-cyclopentylprop-1'-yl)-1-hydroxycyclopent-2-yl]acetic acid, Y-lactone;

[(1S,2R,3S,4R,3'RS)-4-(4"-biphenylcarbonyloxy)-3-(3'-t-butyldimethylsilyloxy-4'-cyclopentylprop-1'-yl)-1-hydroxycyclopent-2-yl]acetic acid, Y-lactone;

[(1S,2R,3S,4R,3'S)-4-(4"-biphenylcarbonyloxy)-3-(3'-t-butyldimethylsilyloxy-4'-methyl-4'-phenoxybut-1'-yl)-1-hydroxycyclopent-2-yl]acetic acid, Y-lactone;

[(1S,2R,3S,4R,3'RS)-4-(4"-biphenylcarbonyloxy)-3-(3'-t-butyldimethylsilyloxy-4'-methyl-4'-phenoxybut-1'-yl)-1-hydroxycyclopent-2-yl]acetic acid, Y-lactone;

[(1S,2R,3S,4R,3'S)-4-(4"-biphenylcarbonyloxy)-3-(3'-t-butyldimethylsilyloxy-4'-methyloct-1'-yl)-1-hydroxycyclopent-2-yl]acetic acid, Y-lactone;

[(1S,2R,3S,4R,3'RS)-4-(4"-biphenylcarbonyloxy)-3-(3'-t-butyldimethylsilyloxy-4-methyloct-1'-yl)-1-hydroxycyclopent-2-yl]acetic acid, Y-lactone;

[(1S,2R,3S,4R,3'S)-4-(4"-biphenylcarbonyloxy)-3-(3'-t-butyldimethylsilyloxy-3'-methyl-3'-cyclohexylprop-1'-yl)-1-hydroxycyclopent-2-yl]acetic acid, Y-lactone;

[(1S,2R,3S,4R,3'RS)-4-(4"-biphenylcarbonyloxy)-3-(3'-t-butyldimethylsilyloxy-3'-methyl-3'-cyclohexylprop-1'-yl)-1-hydroxycyclopent-2-yl]acetic acid, Y-lactone;

[(1S,2R,3S,4R,3'S)-4-(4"-biphenylcarbonyloxy)-3-(3'-t-butyldimethylsilyloxy-3'-methyloct-1'-yl)-1-hydroxycyclopent-2-yl]acetic acid, Y-lactone; and

[(1S,2R,3S,4R,3'RS)-4-(4"-biphenylcarbonyloxy)-3-(3'-t-butyldimethylsilyloxy-3'-methyloct-1'-yl)-1-hydroxycyclopent-2-yl]acetic acid, Y-lactone.

PREPARATION 9

Preparation of
[(1S,2R,3R,4R,3'S)-4-hydroxy-3-(3'-t-butyldimethylsilyloxy-4'-phenoxybut-1'-yl)-1-hydroxycyclopent-2-yl]acetic acid, Y-lactone and Related Compounds of Formula (12)

A. A solution of [(1S,2R,3R,4R,3'S)-4-(4"-biphenylcarbonyloxy)-3-(3'-t-butyldimethylsilyloxy-4'-phenoxybut-1'-yl)-1-hydroxycyclopent-2-yl]acetic acid, Y-lactone, the compound of formula (11), (3.12 g, 5.19 mmol) in 20 ml of methanol was stirred for 24 hrs with anhydrous potassium carbonate (240 mg, 1.7 mmol) at room temperature. Then acetic acid (0.203 ml, 3.3 mmol) was added, the solvent removed under reduced pressure and the residue partitioned between water (30 ml) and ethyl acetate (30 ml). The aqueous phase was extracted with ethyl acetate (4×30 ml), and the combined organic extracts were dried over anhydrous magnesium sulfate and the solvent removed under reduced pressure. The residue was purified by column chromatography (silica gel, hexane/ethyl acetate, 60/40) giving [(1S,2R,3R,4R,3'S)-4-hydroxy-3-(3'-t-butyldimethylsilyloxy-4'-phenoxybut-1'-yl)-1-hydroxycyclopent-2-yl]acetic acid, Y-lactone, the compound of formula (12), 1.47 g.

B. Similarly, following the procedure of A above and replacing [(1S,2R,3R,4R,3'S)-4-(4''-biphenylcarbonyloxy)-3-(3'-t-butyldimethylsilyloxy-4'-phenoxybut-1'-yl)-1-hydroxycyclopent-2-yl]acetic acid, Y-lactone with [(1S,2R,3R,4R,3'R)-4-(4''-biphenylcarbonyloxy)-3-(3'-t-butyldimethylsilyloxy-4'-phenoxybut-1'-yl)-1-hydroxycyclopent-2-yl]acetic acid, Y-lactone, the following compound of formula (12) was prepared:

[(1S,2R,3R,4R,3'R)-4-hydroxy-3-(3'-t-butyldimethylsilyloxy-4'-phenoxybut-1'-yl)-1-hydroxycyclopent-2-yl]-acetic acid, Y-lactone.

C. Similarly, following the procedure of A above and replacing [(1S,2R,3R,4R,3'S)-4-(4''-biphenylcarbonyloxy)-3-(3'-t-butyldimethylsilyloxy-4'-phenoxybut-1'-yl)-1-hydroxycyclopent-2-yl]acetic acid, Y-lactone with the appropriate compound of formula (11), the following representative compounds of formula (12) are prepared:

[(1S,2R,3R,4R,3'RS)-4-hydroxy-3-(3'-t-butyldimethylsilyloxy-4'-phenoxybut-1'-yl)-1-hydroxycyclopent-2-yl]-acetic acid, Y-lactone;

[(1S,2R,3R,4R,3'S)-4-hydroxy-3-(3'-t-butyldimethylsilyloxy-3'-cyclohexylprop-1'-yl)-1-hydroxycyclopent-2-yl]acetic acid, Y-lactone;

[(1S,2R,3R,4R,3'R)-4-hydroxy-3-(3'-t-butyldimethylsilyloxy-3'-cyclohexylprop-1'-yl)-1-hydroxycyclopent-2-yl]acetic acid, Y-lactone;

[(1S,2R,3R,4R,3'RS)-4-hydroxy-3-(3'-t-butyldimethylsilyloxy-3'-cyclohexylprop-1'-yl)-1-hydroxycyclopent-2-yl]acetic acid, Y-lactone;

[(1S,2R,3R,4R,3'S)-4-hydroxy-3-(3'-t-butyldimethylsilyloxyoct-1'-yl)-1-hydroxycyclopent-2-yl]acetic acid, Y-lactone;

[(1S,2R,3R,4R,3'R)-4-hydroxy-3-(3'-t-butyldimethylsilyloxyoct-1'-yl)-1-hydroxycyclopent-2-yl]acetic acid, Y-lactone;

[(1S,2R,3R,4R,3'RS)-4-hydroxy-3-(3'-t-butyldimethylsilyloxyoct-1'-yl)-1-hydroxycyclopent-2-yl]acetic acid, Y-lactone;

[(1S,2R,3R,4R,3'S)-4-hydroxy-3-(3'-t-butyldimethylsilyloxy-4'-methylnon-1'-yl)-1-hydroxycyclopent-2-yl]acetic acid, Y-lactone;

[(1S,2R,3R,4R,3'RS)-4-hydroxy-3-(3'-t-butyldimethylsilyloxy-4'-methylnon-1'-yl)-1-hydroxycyclopent-2-yl]acetic acid, Y-lactone;

[(1S,2R,3R,4R,3'S)-4-hydroxy-3-(3'-t-butyldimethylsilyloxy-4'-phenylbut-1'-yl)-1-hydroxycyclopent-2-yl]acetic acid, Y-lactone;

[(1S,2R,3R,4R,3'RS)-4-hydroxy-3-(3'-t-butyldimethylsilyloxy-4'-phenylbut-1'-yl)-1-hydroxycyclopent-2-yl]acetic acid, Y-lactone;

[(1S,2R,3R,4R,3'S)-4-hydroxy-3-(3'-t-butyldimethylsilyloxy-4'-cyclopentylprop-1'-yl)-1-hydroxycyclopent-2-yl]acetic acid, Y-lactone;

[(1S,2R,3R,4R,3'RS)-4-hydroxy-3-(3'-t-butyldimethylsilyloxy-4'-cyclopentylprop-1'-yl)-1-hydroxycyclopent-2-yl]acetic acid, Y-lactone;

[(1S,2R,3R,4R,3'S)-4-hydroxy-3-(3'-t-butyldimethylsilyloxy-4'-methyl-4'-phenoxybut-1'-yl)-1-hydroxycyclopent-2-yl]acetic acid, Y-lactone;

[(1S,2R,3R,4R,3'RS)-4-hydroxy-3-(3'-t-butyldimethylsilyloxy-4'-methyl-4'-phenoxybut-1'-yl)-1-hydroxycyclopent-2-yl]acetic acid, Y-lactone;

[(1S,2R,3R,4R,3'S)-4-hydroxy-3-(3'-t-butyldimethylsilyloxy-4'-methyloct-1'-yl)-1-hydroxycyclopent-2-yl]acetic acid, Y-lactone;

[(1S,2R,3R,4R,3'RS)-4-hydroxy-3-(3'-t-butyldimethylsilyloxy-4'-methyloct-1'-yl)-1-hydroxycyclopent-2-yl]acetic acid, Y-lactone;

[(1S,2R,3R,4R,3'S)-4-hydroxy-3-(3'-t-butyldimethylsilyloxy-3'-methyl-3'-cyclohexylprop-1'-yl)-1-hydroxycyclopent-2-yl]acetic acid, Y-lactone;

[(1S,2R,3R,4R,3'RS)-4-hydroxy-3-(3'-t-butyldimethylsilyloxy-3'-methyl-3'-cyclohexylprop-1'-yl)-1-hydroxycyclopent-2-yl]acetic acid, Y-lactone;

[(1S,2R,3R,4R,3'S)-4-hydroxy-3-(3'-t-butyldimethylsilyloxy-3'-methyloct-1'-yl)-1-hydroxycyclopent-2-yl]acetic acid, Y-lactone; and

[(1S,2R,3R,4R,3'RS)-4-hydroxy-3-(3'-t-butyldimethylsilyloxy-3'-methyloct-1'-yl)-1-hydroxycyclopent-2-yl]acetic acid, Y-lactone.

PREPARATION 10

Preparation of [(1S,2R,3'S)-3-(3'-t-butyldimethylsilyloxy-4'-phenoxybut-1'-yl)-1-hydroxycyclopent-3-en-2-yl]acetic acid, Y-lactone and Related Compounds of Formula (6)

A. Trifluoromethanesulfonic anhydride (8.0 g, 28.5 mmol) was added dropwise at −20° C. to a solution of [(1S,2R,3R,4R,3'S)-4-hydroxy-3-(3'-t-butyldimethylsilyloxy-4'-phenoxybut-1'-yl)-1-hydroxycyclopent-2-yl]acetic acid, Y-lactone, the compound of formula (12), (8.0 g, 19.01 mmol) and 2,4,6-collidine (7.37 g, 60.83 mmol) in 40 ml of dry methylene chloride. After stirring for 10 min at −20° C., the temperature was allowed to reach 20° C. over a period of 2 hrs and stirred for 1 hour more. It was then poured into water (50 ml) and extracted with methylene chloride (3×30 ml). The combined organic extracts were washed with 10% hydrochloric acid (30 ml) and saturated sodium bicarbonate (30 ml), dried over anhydrous magnesium sulfate and the solvent removed under reduced pressure. The residue was purified by column chromatography (silica gel, hexane/ethyl acetate, 80/20) giving [(1S,2R,3'S)-3-(3'-t-butyldimethylsilyloxy-4'-phenoxybut-1'-yl)-1-hydroxycyclopent-3-en-2-yl]acetic acid, Y-lactone, the compound of formula (6), 7.25 g.

B. Similarly, following the procedure of A above and replacing [(1S,2R,3R,4R,3'S)-4-hydroxy-3-(3'-t-butyldimethylsilyloxy-4'-phenoxybut-1'-yl)-1-hydroxycyclopent-2-yl]acetic acid, Y-lactone with [(1S,2R,3R,4R,3'R)-4-hydroxy-3-(3'-t-butyldimethylsilyloxy-4'-phenoxybut-1'-yl)-1-hydroxycyclopent-2-yl]acetic acid, Y-lactone, the following compound of formula (6) was prepared:

[(1S,2R,3'R)-3-(3'-t-butyldimethylsilyloxy-4'-phenoxybut-1'-yl)-1-hydroxycyclopent-3-en-2-yl]acetic acid, Y-lactone.

C. Similarly, following the procedure of A above and replacing [(1S,2R,3R,4R,3'S)-4-hydroxy-3-(3'-t-butyldimethylsilyloxy-4'-phenoxybut-1'-yl)-1-hydroxycyclopent-2-yl]acetic acid, Y-lactone with the appropriate compound of formula (12), the following representative compounds of formula (6) are prepared:

[(1S,2R,3'RS)-3-(3'-t-butyldimethylsilyloxy-4'-phenoxybut-1'-yl)-1-hydroxycyclopent-3-en-2-yl]acetic acid, Y-lactone;

[(1S,2R,3'S)-3-(3'-t-butyldimethylsilyloxy-3'-cyclohexylprop-1'-yl)-1-hydroxycyclopent-3-en-2-yl]acetic acid, Y-lactone;

[(1S,2R,3'R)-3-(3'-t-butyldimethylsilyloxy-3'-cyclohexylprop-1'-yl)-1-hydroxycyclopent-3-en-2-yl]acetic acid, Y-lactone;

[(1S,2R,3'RS)-3-(3'-t-butyldimethylsilyloxy-3'-cyclohexylprop-1'-yl)-1-hydroxycyclopent-3-en-2-yl]acetic acid, Y-lactone;

[(1S,2R,3'S)-3-(3'-t-butyldimethylsilyloxyoct-1'-yl)-1-hydroxycyclopent-3-en-2-yl]acetic acid, Y-lactone;

[(1S,2R,3'R)-3-(3'-t-butyldimethylsilyloxyoct-1'-yl)-1-hydroxycyclopent-3-en-2-yl]acetic acid, Y-lactone;

[(1S,2R,3'RS)-3-(3'-t-butyldimethylsilyloxyoct-1'-yl)-1-hydroxycyclopent-3-en-2-yl]acetic acid, Y-lactone;

[(1S,2R,3'S)-3-(3'-t-butyldimethylsilyloxy-4'-methylnon-1'-yl)-1-hydroxycyclopent-3-en-2-yl]acetic acid, Y-lactone;

[(1S,2R,3'RS)-3-(3'-t-butyldimethylsilyloxy-4'-methylnon-1'-yl)-1-hydroxycyclopent-3-en-2-yl]acetic acid, Y-lactone;

[(1S,2R,3'S)-3-(3'-t-butyldimethylsilyloxy-4'-phenylbut-1'-yl)-1-hydroxycyclopent-3-en-2-yl]acetic acid, Y-lactone;

[(1S,2R,3'RS)-3-(3'-t-butyldimethylsilyloxy-4'-phenylbut-1'-yl)-1-hydroxycyclopent-3-en-2-yl]acetic acid, Y-lactone;

[(1S,2R,3'S)-3-(3'-t-butyldimethylsilyloxy-4'-cyclopentylprop-1'-yl)-1-hydroxycyclopent-3-en-2-yl]acetic acid, Y-lactone;

[(1S,2R,3'RS)-3-(3'-t-butyldimethylsilyloxy-4'-cyclopentylprop-1'-yl)-1-hydroxycyclopent-3-en-2-yl]acetic acid, Y-lactone;

[(1S,2R,3'S)-3-(3'-t-butyldimethylsilyloxy-4'-methyl-4'-phenoxybut-1'-yl)-1-hydroxycyclopent-3-en-2-yl]acetic acid, Y-lactone;

[(1S,2R,3'RS)-3-(3'-t-butyldimethylsilyloxy-4'-methyl-4'-phenoxybut-1'-yl)-1-hydroxycyclopent-3-en-2-yl]acetic acid, Y-lactone;

[(1S,2R,3'S)-3-(3'-t-butyldimethylsilyloxy-4'-methyloct-1'-yl)-1-hydroxycyclopent-3-en-2-yl]acetic acid, Y-lactone;

[(1S,2R,3'RS)-3-(3'-t-butyldimethylsilyloxy-4'-methyloct-1'-yl)-1-hydroxycyclopent-3-en-2-yl]acetic acid, Y-lactone;

[(1S,2R,3'S)-3-(3'-t-butyldimethylsilyloxy-3'-methyl-3'-cyclohexylprop-1'-yl)-1-hydroxycyclopent-3-en-2-yl]acetic acid, Y-lactone;

[(1S,2R,3'RS)-3-(3'-t-butyldimethylsilyloxy-3'-methyl-3'-cyclohexylprop-1'-yl)-1-hydroxycyclopent-3-en-2-yl]acetic acid, Y-lactone;

[(1S,2R,3'S)-3-(3'-t-butyldimethylsilyloxy-3'-methyloct-1'-yl)-1-hydroxycyclopent-3-en-2-yl]acetic acid, Y-lactone; and

[(1S,2R,3'RS)-3-(3'-t-butyldimethylsilyloxy-3'-methyloct-1'-yl)-1-hydroxycyclopent-3-en-2-yl]acetic acid, Y-lactone.

PREPARATION 11

Preparation of (8R,9S,15S)-9-hydroxy-15-(t-butyldimethylsilyloxy)-16-phenoxy-17,18,19,20-tetranorprosta-5(Z),11-dienoic acid, methyl ester and related Compounds of Formula (7) where X is cis —CH=CH— and m is 3

A. A solution of diisobutylaluminum hydride (1.44 M in toluene, 1.5 ml) was added dropwise at −78° C. to a solution of [(1S,2R,3'S)-3-(3'-t-butyldimethylsilyloxy-4'-phenoxybut-1'-yl)-1-hydroxycyclopent-3-en-2-yl]acetic acid, Y-lactone, the compound of formula (6), (727 mg, 1.80 mmol) in 5 ml of toluene. After 30 min, the excess of hydride was destroyed with a few drops of methanol, and the reaction mixture allowed to warm up to room temperature. It was then diluted with methylene chloride (50 ml), filtered through Celite and the solvent removed under reduced pressure. The residue was dissolved in 4 ml of dimethylsulfoxide and added to a solution of the ylid formed by treating a solution of 4-carboxybutyltriphenylphosphonium bromide (2.66 g, 6.00 mmol) in 4.5 ml of dimethylsulfoxide with 5.7 ml of 2M dimsyl sodium in dimethylsulfoxide, (prepared by dissolving 1.56 g sodium hydride in 30 ml dimethyl sulfoxide at 65° C. under nitrogen). After 2 hours the reaction was poured onto a mixture of iced water (100 ml) and ethyl acetate/ether 1:1 (50 ml). The mixture was then acidified to pH 3–4 with solid citric acid, and after separation of the phases the aqueous phase was extracted with ethyl acetate-ether 1:1 (2×50 ml). The combined organic extracts were washed with brine, dried over anhydrous magnesium sulfate and the solvent removed under reduced pressure. The residue was dissolved in excess of an ethereal solution of diazomethane, and after 5 min the solvent removed under reduced pressure. Column chromatography (silica gel, hexane/ethyl acetate, 80/20) of the residue afforded (8R,9S,15S)-9-hydroxy-15-(t-butyldimethylsilyloxy)-16-phenoxy-17,18,19,20-tetranorprosta-5(Z),11-dienoic acid, methyl ester, the compound of formula (7) where X is cis —CH=CH— and m is 3, 446 mg.

B. Similarly, following the procedure of A above and replacing [(1S,2R,3'S)-3-(3'-t-butyldimethylsilyloxy-4'-phenoxybut-1'-yl)-1-hydroxycyclopent-3-en-2-yl]acetic acid, Y-lactone with the appropriate compound of formula (6), the following compounds of formula (7) were prepared:

(8R,9S,15R)-9-hydroxy-15-(t-butyldimethylsilyloxy)-16-phenoxy-17,18,19,20-tetranorprosta-5(Z),11-dienoic acid, methyl ester;

(±)-9-hydroxy-15-(t-butyldimethylsilyloxy)-16-phenoxy-17,18,19,20-tetranorprosta-5(Z),11-dienoic acid, methyl ester;

(8R,9S,15S)-8-methyl-9-hydroxy-15-(t-butyldimethylsilyloxy)-16-phenoxy-17,18,19,20-tetranorprosta-5(Z),11-dienoic acid, methyl ester;

(±)-9-hydroxy-15-(t-butyldimethylsilyloxy)-15-cyclohexyl-16,17,18,19,20-pentanorprosta-5(Z),11-dienoic acid, methyl ester; and (±)-9-hydroxy-15-(t-butyldimethylsilyloxy)-prosta-5(Z),11-dienoic acid, methyl ester.

C. Similarly, following the procedure of A above and replacing [(1S,2R,3'S)-3-(3'-t-butyldimethylsilyloxy-4'-phenoxybut-1'-yl)-1-hydroxycyclopent-3-en-2-yl]acetic acid, Y-lactone with the appropriate compound of formula (6), the following compounds of formula (7) are prepared:

[(±)-9-hydroxy-15-(t-butyldimethylsilyloxy)-16-phenyl-17,18,19,20-tetranorprosta-5(Z),11-dienoic acid, methyl ester;

[(±)-9-hydroxy-15-(t-butyldimethylsilyloxy)-16,20-dimethylprosta-5(Z),11-dienoic acid, methyl ester;

[(±)-9-hydroxy-15-(t-butyldimethylsilyloxy)-20-butylprosta-5(Z),11-dienoic acid, methyl ester;

[(±)-9-hydroxy-15-(t-butyldimethylsilyloxy)-20,20,20-trifluoroprosta-5(Z),11-dienoic acid, methyl ester;

(±)-9-hydroxy-15-(t-butyldimethylsilyloxy)-15-cyclopentyl-16,17,18,19,20-pentanorprosta-5(Z),11-dienoic acid, methyl ester;

[(±)-9-hydroxy-15-(t-butyldimethylsilyloxy)-16-methyl-16-phenoxy-17,18,19,20-tetranorprosta-5(Z),11-dienoic acid, methyl ester;

[(±)-9-hydroxy-15-(t-butyldimethylsilyloxy)-16-methylprosta-5(Z),11-dienoic acid, methyl ester;

[(8R,9S,15RS)-8-methyl-9-hydroxy-15-(t-butyldimethylsilyloxy)-15-cyclohexyl-16,17,18,19,20-pentanorprosta-5(Z),11-dienoic acid, methyl ester;
[(8R,9S,15RS)-8-methyl-9-hydroxy-15-(t-butyldimethylsilyloxy)-prosta-5(Z),11-dienoic acid, methyl ester;
[(±)-9-hydroxy-15-(t-butyldimethylsilyloxy)-15-methyl-15-cyclohexyl-16,17,18,19,20-pentanorprosta-5(Z),11-dienoic acid, methyl ester;
[(±)-9-hydroxy-15-(t-butyldimethylsilyloxy)-15-methylprosta-5(Z),11-dienoic acid, methyl ester;
[(8R,9S,15RS)-8-n-butyl-9-hydroxy-15-(t-butyldimethylsilyloxy)-16-phenoxy-17,18,19,20-tetranorprosta-5(Z),11-dienoic acid, methyl ester;
[(8R,9S,15RS)-9-hydroxy-15-(t-butyldimethylsilyloxy)-16-phenoxybut-1'-yl)-17,18,19,20-tetranorprosta-5(Z),11-dienoic acid, methyl ester;
[(8R,9S,15S)-9-hydroxy-15-(t-butyldimethylsilyloxy)-15-cyclohexyl-16,17,18,19,20-pentanorprosta-5(Z),11-dienoic acid, methyl ester;
[(8R,9S,15R)-9-hydroxy-15-(t-butyldimethylsilyloxy)-15-cyclohexyl-16,17,18,19,20-pentanorprosta-5(Z),11-dienoic acid, methyl ester;
[(8R,9S,15RS)-9-hydroxy-15-(t-butyldimethylsilyloxy)-15-cyclohexyl-16,17,18,19,20-pentanorprosta-5(Z),11-dienoic acid, methyl ester;
[(8R,9S,15S)-9-hydroxy-15-(t-butyldimethylsilyloxy)-prosta-5(Z),11-dienoic acid, methyl ester;
[(8R,9S,15R)-9-hydroxy-15-(t-butyldimethylsilyloxy)-prosta-5(Z),11-dienoic acid, methyl ester;
[(8R,9S,15RS)-9-hydroxy-15-(t-butyldimethylsilyloxy)-prosta-5(Z),11-dienoic acid, methyl ester;
[((8R,9S,15S)-9-hydroxy-15-(t-butyldimethylsilyloxy)-16,20-dimethylprosta-5(Z),11-dienoic acid, methyl ester;
[((8R,9S,15RS)-9-hydroxy-15-(t-butyldimethylsilyloxy)-16,20-dimethylprosta-5(Z),11-dienoic acid, methyl ester;
[(8R,9S,15S)-9-hydroxy-15-(t-butyldimethylsilyloxy)-16-phenyl-17,18,19,20-tetranorprosta-5(Z),11-dienoic acid, methyl ester;
[(8R,9S,15RS)-9-hydroxy-15-(t-butyldimethylsilyloxy)-16-phenyl-17,18,19,20-tetranorprosta-5(Z),11-dienoic acid, methyl ester;
[(8R,9S,15S)-9-hydroxy-15-(t-butyldimethylsilyloxy)-15-cyclopentyl-16,17,18,19,20-pentanorprosta-5(Z),11-dienoic acid, methyl ester;
[(8R,9S,15RS)-9-hydroxy-15-(t-butyldimethylsilyloxy)-15-cyclopentyl-16,17,18,19,20-pentanorprosta-5(Z),11-dienoic acid, methyl ester;
[(8R,9S,15S)-9-hydroxy-15-(t-butyldimethylsilyloxy)-16-methyl-16-phenoxy-17,18,19,20-tetranorprosta-5(Z),11-dienoic acid, methyl ester;
[(8R,9S,15RS)-9-hydroxy-15-(t-butyldimethylsilyloxy)-16-methyl-16-phenoxy-17,18,19,20-tetranorprosta-5(Z),11-dienoic acid, methyl ester;
[(8R,9S,15R)-9-hydroxy-15-(t-butyldimethylsilyloxy)-16-methylprosta-5(Z),11-dienoic acid, methyl ester;
[(8R,9S,15RS)-9-hydroxy-15-(t-butyldimethylsilyloxy)-16-methylprosta-5(Z),11-dienoic acid, methyl ester;
[(8R,9S,15R)-9-hydroxy-15-(t-butyldimethylsilyloxy)-15-methyl-15-cyclohexyl-16,17,18,19,20-pentanorprosta-5(Z),11-dienoic acid, methyl ester;
[(8R,9S,15RS)-9-hydroxy-15-(t-butyldimethylsilyloxy)-15-methyl-15-cyclohexyl-16,17,18,19,20-pentanorprosta-5(Z),11-dienoic acid, methyl ester;
[(8R,9S,15S)-9-hydroxy-15-(t-butyldimethylsilyloxy)-15-methyl-16-methylprosta-5(Z),11-dienoic acid, methyl ester; and
[(8R,9S,15RS)-9-hydroxy-15-(t-butyldimethylsilyloxy)-15-methyl-16-methylprosta-5(Z),11-dienoic acid, methyl ester.

PREPARATION 12

Preparation of [(1S,2R,3R,4R,3'S)-4-tetrahydropyranyloxy-3-(3'-t-butyldimethylsilyloxy-4'-phenoxybut-1'-yl)-1-hydroxycyclopent-2-yl]acetic acid, Y-lactone and Related Compounds of Formula (15)

A. Freshly distilled dihydropyran (0.21 ml, 2.29 mmol) was added to a solution of [(1S,2R,3R,4R,3'S)-4-hydroxy-3-(3'-t-butyldimethylsilyloxy-4'-phenoxybut-1'-yl)-1-hydroxycyclopent-2-yl]acetic acid, Y-lactone, the compound of formula (12), (643 mg, 1.53 mmol) and p-toluenesulfonic acid (2.1 mg, 0.0122 mmol) in 5 ml of methylene chloride. After 30 minutes, pyridine (0.03 ml, 0.352 mmol) was added and the mixture was washed with water (2 ml). The organic layer was dried (anhydrous magnesium sulfate) and evaporated. The residue was purified by preparative TLC (silica gel, hexane/ethyl acetate 1/1) giving [(1S,2R,3R,4R,3'S)-4-tetrahydropyranyloxy-3-(3'-t-butyldimethylsilyloxy-4'-phenoxybut-1'-yl)-1-hydroxycyclopent-2-yl]acetic acid, Y-lactone, the compound of formula (15) (710 mg).

B. Similarly, following the procedure of A above and replacing [(1S,2R,3R,4R,3'S)-4-hydroxy-3-(3'-t-butyldimethylsilyloxy-4'-phenoxybut-1'-yl)-1-hydroxycyclopent-2-yl]acetic acid, T-lactone with the appropriate compound of formula (12), the following compounds of formula (15) are prepared:
[(1S,2R,3R,4R,3'R)-4-tetrahydropyranyloxy-3-(3'-t-butyldimethylsilyloxy-4'-phenoxybut-1'-yl)-1-hydroxycyclopent-2-yl]-acetic acid, Y-lactone;
[(1S,2R,3R,4R,3'RS)-4-tetrahydropyranyloxy-3-(3'-t-butyldimethylsilyloxy-4'-phenoxybut-1'-yl)-1-hydroxycyclopent-2-yl]-acetic acid, Y-lactone;
[(1S,2R,3S,4R,3'S)-4-tetrahydropyranyloxy-3-(3'-t-butyldimethylsilyloxy-3'-cyclohexylprop-1'-yl)-1-hydroxycyclopent-2-yl]acetic acid, Y-lactone;
[(1S,2R,3S,4R,3'R)-4-tetrahydropyranyloxy-3-(3'-t-butyldimethylsilyloxy-3'-cyclohexylprop-1'-yl)-1-hydroxycyclopent-2-yl]acetic acid, Y-lactone;
[(1S,2R,3S,4R,3'RS)-4-tetrahydropyranyloxy-3-(3'-t-butyldimethylsilyloxy-3'-cyclohexylprop-1'-yl)-1-hydroxycyclopent-2-yl]acetic acid, Y-lactone;
[(1S,2R,3S,4R,3'S)-4-tetrahydropyranyloxy-3-(3'-t-butyldimethylsilyloxyoct-1'-yl)-1-hydroxycyclopent-2-yl]acetic acid, Y-lactone;
[(1S,2R,3S,4R,3'R)-4-tetrahydropyranyloxy-3-(3'-t-butyldimethylsilyloxyoct-1'-yl)-1-hydroxycyclopent-2-yl]acetic acid, Y-lactone;
[(1S,2R,3S,4R,3'R)-4-tetrahydropyranyloxy-3-(3'-t-butyldimethylsilyloxyoct-1'-yl)-1-hydroxycyclopent-2-yl]acetic acid, Y-lactone;
[(1S,2R,3S,4R,3'S)-4-tetrahydropyranyloxy-3-(3'-t-butyldimethylsilyloxy-4'-methylnon-1'-yl)-1-hydroxycyclopent-2-yl]-acetic acid, Y-lactone;
[(1S,2R,3S,4R,3'RS)-4-tetrahydropyranyloxy-3-(3'-t-butyldimethylsilyloxy-4'-methylnon-1'-yl)-1-hydroxycyclopent-2-yl]-acetic acid, Y-lactone;
[(1S,2R,3S,4R,3'S)-4-tetrahydropyranyloxy-3-(3'-t-butyldimethylsilyloxy-4'-phenylbut-1'-yl)-1-hydroxycyclopent-2-yl]-acetic acid, Y-lactone;

[(1S,2R,3S,4R,3'RS)-4-tetrahydropyranyloxy-3-(3'-t-butyldimethylsilyloxy-4'-phenylbut-1'-yl)-1-hydroxycyclopent-2-yl]-acetic acid, Y-lactone;

[(1S,2R,3S,4R,3'S)-4-tetrahydropyranyloxy-3-(3'-t-butyldimethylsilyloxy-4'-cyclopentylprop-1'-yl)-1-hydroxycyclopent-2-yl]acetic acid, Y-lactone;

[(1S,2R,3S,4R,3'RS)-4-tetrahydropyranyloxy-3-(3'-t-butyldimethylsilyloxy-4'-cyclopentylprop-1'-yl)-1-hydroxycyclopent-2-yl]acetic acid, Y-lactone;

[(1S,2R,3S,4R,3'S)-4-tetrahydropyranyloxy-3-(3'-t-butyldimethylsilyloxy-4'-methyl-4'-phenoxybut-1'-yl)-1-hydroxycyclopent-2-yl]acetic acid, Y-lactone;

[(1S,2R,3S,4R,3'RS)-4-tetrahydropyranyloxy-3-(3'-t-butyldimethylsilyloxy-4'-methyl-4'-phenoxybut-1'-yl)-1-hydroxycyclopent-2-yl]acetic acid, Y-lactone;

[(1S,2R,3S,4R,3'S)-4-tetrahydropyranyloxy-3-(3'-t-butyldimethylsilyloxy-4'-methyloct-1'-yl)-1-hydroxycyclopent-2-yl]acetic acid, Y-lactone;

[(1S,2R,3S,4R,3'RS)-4-tetrahydropyranyloxy-3-(3'-t-butyldimethylsilyloxy-4'-methyloct-1'-yl)-1-hydroxycyclopent-2-yl]acetic acid, Y-lactone;

[(1S,2R,3S,4R,3'S)-4-tetrahydropyranyloxy-3-(3'-t-butyldimethylsilyloxy-3'-cyclohexylprop-1'-yl)-1-hydroxy-2-methylcyclopent-2-yl]acetic acid, Y-lactone;

[(1S,2R,3S,4R,3'RS)-4-tetrahydropyranyloxy-3-(3'-t-butyldimethylsilyloxy-3'-cyclohexylprop-1'-yl)-1-hydroxy-2-methylcyclopent-2-yl]acetic acid, Y-lactone;

[(1S,2R,3S,4R,3'S)-4-tetrahydropyranyloxy-3-(3'-t-butyldimethylsilyloxyoct-1'-yl)-1-hydroxy-2-methylcyclopent-2-yl]acetic acid, Y-lactone;

[(1S,2R,3S,4R,3'RS)-4-tetrahydropyranyloxy-3-(3'-t-butyldimethylsilyloxyoct-1'-yl)-1-hydroxy-2-methylcyclopent-2-yl]acetic acid, Y-lactone;

[(1S,2R,3S,4R,3'S)-4-tetrahydropyranyloxy-3-(3'-t-butyldimethylsilyloxy-3'-methyl-3'-cyclohexylprop-1'-yl)-1-hydroxycyclopent-2-yl]acetic acid, Y-lactone;

[(1S,2R,3S,4R,3'RS)-4-tetrahydropyranyloxy-3-(3'-t-butyldimethylsilyloxy-3'-methyl-3'-cyclohexylprop-1'-yl)-1-hydroxycyclopent-2-yl]acetic acid, Y-lactone;

[(1S,2R,3S,4R,3'S)-4-tetrahydropyranyloxy-3-(3'-t-butyldimethylsilyloxy-3'-methyloct-1'-yl)-1-hydroxycyclopent-2-yl]acetic acid, Y-lactone;

[(1S,2R,3S,4R,3'RS)-4-tetrahydropyranyloxy-3-(3'-t-butyldimethylsilyloxy-3'-methyloct-1'-yl)-1-hydroxycyclopent-2yl]acetic acid, Y-lactone;

[(1S,2R,3S,4R,3'S)-4-tetrahydropyranyloxy-3-(3'-t-butyldimethylsilyloxy-4'-phenoxybut-1'-yl)-1-hydroxy-2-n-butylcyclopent-2-yl]acetic acid, Y-lactone; and

[(1S,2R,3S,4R,3'RS)-4-tetrahydropyranyloxy-3-(3'-t-butyldimethylsilyloxy-4'-phenoxybut-1'-yl)-1-hydroxy-2-n-butylcyclopent-2-yl]acetic acid, Y-lactone.

PREPARATION 13

Preparation of (8R,9S,15S)-9-hydroxy-11-tetrahydropyranyloxy-15-(t-butyldimethylsilyloxy)-16-phenoxy-17,18,19,20-tetranorprosta-5(Z)-enoic acid, methyl ester and Related Compounds of Formula (16)

A. A solution of diisobutylaluminum hydride (1.44 M in toluene, 5.8 ml) was added dropwise at −78° C. to a solution of [(1S,2R,3R,4R,3'S)-4-tetrahydropyranyloxy-3-(3'-t-butyldimethylsilyloxy-4'-phenoxybut-1'-yl)-1-hydroxycyclopent-2-yl]acetic acid, Y-lactone, the compound of formula (15), (3.54 g, 7.014 mmol) in 5 ml of toluene. After 30 min, the excess of hydride was destroyed with a few drops of methanol, and the reaction mixture allowed to warm up to room temperature. It was then diluted with methylene chloride (50 ml), filtered through Celite and the solvent removed under reduced presure. The residue was dissolved in 4 ml of dimethylsulfoxide and added to a solution of the ylid formed by treating a solution of 4-carboxybutyltriphenylphosphonium bromide (10.34 g, 23.3 mmol) in 15 ml of dimethylsulfoxide with 22.2 ml of 2M dimsyl sodium in dimethylsulfoxide, (prepared by dissolving 1.56 g sodium hydride in 30 ml dimethyl sulfoxide at 65° C. under nitrogen). After 2 hours the reaction was poured onto a mixture of iced water (100 ml) and ethyl acetate/ether 1:1 (50 ml). The mixture was then acidified to pH 3–4 with solid citric acid, and after separation of the phases the aqueous phase was extracted with ethyl acetate/ether 1:1 (2×50 ml). The combined organic extracts were washed with brine, dried over anhydrous magnesium sulfate and the solvent removed under reduced pressure. The residue was dissolved in excess of ethereal solution of diazomethane, and after 5 min the solvent removed under reduced pressure. Column chromatography (silica gel, hexane/ethyl acetate 80/20) of the residue afforded (8R,9S,15S)-9-hydroxy-11-tetrahydropyranyloxy-15-(t-butyldimethylsilyloxy)-16-phenoxy-17,18,19,20-tetranorprosta-5(Z)-enoic acid, methyl ester, the compound of formula (16), 1.5 g.

B. Similarly, following the procedure of A above and replacing [(1S,2R,3R,4R,3's)-4-tetrahydropyranyloxy-3-(3'-t-butyldimethylsilyloxy-4'-phenoxybut-1'-yl)-1-hydroxycyclopent-2-yl]acetic acid, Y-lactone with the appropriate compound of formula (15), the following compounds of formula (16) are prepared:

(8R,9S,15R)-9-hydroxy-11-tetrahydropyranyloxy-15-(t-butyldimethylsilyloxy)-16-phenoxy-17,18,19,20-tetranorprosta-5(Z)-enoic acid, methyl ester;

(8R,9S,15RS)-9-hydroxy-11-tetrahydropyranyloxy-15-(t-butyldimethylsilyloxy)-16-phenoxy-17,18,19,20-tetranorprosta-5(Z)-enoic acid, methyl ester;

(8R,9S,15S)-8-methyl-9-hydroxy-11-tetrahydropyranyloxy-15-(t-butyldimethylsilyloxy)-16-phenoxy-17,18,19,20-tetranorprosta-5(Z)-enoic acid, methyl ester;

(8R,9S,15S)-9-hydroxy-11-tetrahydropyranyloxy-15-(t-butyldimethylsilyloxy)-15-cyclohexyl-16,17,18,19,20-pentanorprosta-5(Z)-enoic acid, methyl ester;

(8R,9S,15R)-9-hydroxy-11-tetrahydropyranyloxy-15-(t-butyldimethylsilyloxy)-15-cyclohexyl-16,17,18,19,20-pentanorprosta-5(Z)-enoic acid, methyl ester;

(8R,9S,15RS)-9-hydroxy-11-tetrahydropyranyloxy-15--(t-butyldimethylsilyloxy)---cyclohexyl-16,17,18,19,20-pentanorprosta-5(Z)-enoic acid, methyl ester;

(8R,9S,15S)-9-hydroxy-11-tetrahydropyranyloxy-15-(t-butyldimethylsilyloxy)prosta-5(Z)-enoic acid, methyl ester;

(8R,9S,15R)-9-hydroxy-11-tetrahydropyranyloxy-15-(t-butyldimethylsilyloxy)prosta-5(Z)-enoic acid, methyl ester;

(8R,9S,15RS)-9-hydroxy-11-tetrahydropyranyloxy-15-(t-butyldimethylsilyloxy)prosta-5(Z)-enoic acid, methyl ester;

(8R,9S,15S)-9-hydroxy-11-tetrahydropyranyloxy-15-(t-butyldimethylsilyloxy)-16,20-dimethylprosta-5(Z)-enoic acid, methyl ester;
(8R,9S,15RS)-9-hydroxy-11-tetrahydropyranyloxy-15-(t-butyldimethylsilyloxy)-16,20-dimethylprosta-5(Z)-enoic acid, methyl ester;
(8R,9S,15S)-9-hydroxy-11-tetrahydropyranyloxy-15-(t-butyldimethylsilyloxy)-16-phenyl-17,18,19,20-tetranorprosta-5(Z)-enoic acid, methyl ester;
(8R,9S,15RS)-9-hydroxy-11-tetrahydropyranyloxy-15-(t-butyldimethylsilyloxy)-16-phenyl-17,18,19,20-tetranorprosta-5(Z)-enoic acid, methyl ester;
(8R,9S,15S)-9-hydroxy-11-tetrahydropyranyloxy-15-(t-butyldimethylsilyloxy)-15-cyclopentyl-16,17,18,19,20-pentanorprosta-5(Z)-enoic acid, methyl ester;
(8R,9S,15RS)-9-hydroxy-11-tetrahydropyranyloxy-15-(t-butyldimethylsilyloxy)-15-cyclopentyl-16,17,18,19,20-pentanorprosta-5(Z)-enoic acid, methyl ester;
(8R,9S,15S)-9-hydroxy-11-tetrahydropyranyloxy-15-(t-butyldimethylsilyloxy)-16-methyl-16-phenoxy-17,18,19,20-tetranorprosta-5(Z)-enoic acid, methyl ester;
(8R,9S,15RS)-9-hydroxy-11-tetrahydropyranyloxy-15-(t-butyldimethylsilyloxy)-16-methyl-16-phenoxy-17,18,19,20-tetranorprosta-5(Z)-enoic acid, methyl ester;
(8R,9S,15S)-9-hydroxy-11-tetrahydropyranyloxy-15-(t-butyldimethylsilyloxy)-16-methylprosta-5(Z)-enoic acid, methyl ester;
(8R,9S,15RS)-9-hydroxy-11-tetrahydropyranyloxy-15-(t-butyldimethylsilyloxy)-16-methylprosta-5(Z)-enoic acid, methyl ester;
(8R,9S,15S)-8-methyl-9-hydroxy-11-tetrahydropyranyloxy-15-(t-butyldimethylsilyloxy)-15-cyclohexyl-16,17,18,19,20-pentanorprosta-5(Z)-enoic acid, methyl ester;
(8R,9S,15RS)-8-methyl-9-hydroxy-11-tetrahydropyranyloxy-15-(t-butyldimethylsilyloxy)-15-cyclohexyl-16,17,18,19,20-pentanorprosta-5(Z)-enoic acid, methyl ester;
(8R,9S,15S)-8-methyl-9-hydroxy-11-tetrahydropyranyloxy-15-(t-butyldimethylsilyloxy)prosta-5(Z)-enoic acid, methyl ester;
(8R,9S,15RS)-8-methyl-9-hydroxy-11-tetrahydropyranyloxy-15-(t-butyldimethylsilyloxy)prosta-5(Z)-enoic acid, methyl ester;
(8R,9S,15S)-9-hydroxy-11-tetrahydropyranyloxy-15-(t-butyldimethylsilyloxy)-15-cyclohexyl-18,19,20-pentanorprosta-5(Z)-enoic acid, methyl ester;
(8R,9S,15RS)-9-hydroxy-11-tetrahydropyranyloxy-15-(t-butyldimethylsilyloxy)-15-methyl-15-cyclohexyl-16,17,18,19,20-pentanorprosta-5(Z)-enoic acid, methyl ester;
(8R,9S,15S)-9-hydroxy-11-tetrahydropyranyloxy-15-(t-butyldimethylsilyloxy)-15-methylprosta-5(Z)-enoic acid, methyl ester;
(8R,9S,15RS)-9-hydroxy-11-tetrahydropyranyloxy-15-(t-butyldimethylsilyloxy)-15-methylprosta-5(Z)-enoic acid, methyl ester;
(8R,9S,15S)-8-n-butyl-9-hydroxy-11-tetrahydropyranyloxy-15-(t-butyldimethylsilyloxy)-16-phenoxy-17,18,19,20-tetranorprosta-5(Z)-enoic acid, methyl ester; and
(8R,9S,15RS)-8-n-butyl-9-hydroxy-11-tetrahydropyranyloxy-15-(t-butyldimethylsilyloxy)-16-phenoxy-17,18,19,20-tetranorprosta-5(Z)-enoic acid, methyl ester.

PREPARATION 14

Preparation of (8R,9S,15S)-9-hydroxy-11-tetrahydropyranyloxy-15-(t-butyldimethylsilyloxy)-16-phenoxy-17,18,19,20-tetranorprostanoic acid, methyl ester and Related Compounds of Formula (17)

A. A solution of (8R,9S,15S)-9-hydroxy-11-tetrahydropyranyloxy-15-(t-butyldimethylsilyloxy)-16-phenoxy-17,18,19,20-tetranorprosta-5(Z)-enoic acid, methyl ester, the compound of formula (16), (1.50 g, 2.48 mmol) in 20 ml of EtOH was stirred under hydrogen at atmospheric pressure with 225 mg of 5% Pd/C for 20 hours. After filtration and evaporation of the solvent, the residue was purified by column chromatography (silica gel, hexane/ethyl acetate 85/15) giving 1.14 g of (8R,9S,15S)-9-hydroxy-11-tetrahydropyranyloxy-15-(t-butyldimethylsilyloxy)-16-phenoxy-17,18,19,20-tetranorprostanoic acid, methyl ester, the compound of formula (16).

B. Similarly, following the procedure of A above and replacing (8R,9S,15S)-9-hydroxy-11-tetrahydropyranyloxy-15-(t-butyldimethylsilyloxy)-16-phenoxy-17,18,19,20-tetranorprosta-5-(Z)-enoic acid, methyl ester with the appropriate compound of formula (16), the following compounds of formula (17) are prepared:
(8R,9S,15R)-9-hydroxy-11-tetrahydropyranyloxy-15-(t-butyldimethylsilyloxy)-16-phenoxy-17,18,19,20-tetranorprostanoic acid, methyl ester;
(8R,9S,15RS)-9-hydroxy-11-tetrahydropyranyloxy-15-(t-butyldimethylsilyloxy)-16-phenoxy-17,18,19,20-tetranorprostanoic acid, methyl ester;
(8R,9S,15S)-8-methyl-9-hydroxy-11-tetrahydropyranyloxy-15-(t-butyldimethylsilyloxy)-16-phenoxy-17,18,19,20-tetranorprostanoic acid, methyl ester;
(8R,9S,15S)-9-hydroxy-11-tetrahydropyranyloxy-15-(t-butyldimethylsilyloxy)-15-cyclohexyl-16,17,18,19,20-pentanorprostanoic acid, methyl ester;
(8R,9S,15R)-9-hydroxy-11-tetrahydropyranyloxy-15-(t-butyldimethylsilyloxy)-15-cyclohexyl-16,17,18,19,20-pentanorprostanoic acid, methyl ester;
(8R,9S,15RS)-9-hydroxy-11-tetrahydropyranyloxy-15-(t-butyldimethylsilyloxy)-15-cyclohexyl-16,17,18,19,20-pentanorprostanoic acid, methyl ester;
(8R,9S,15S)-9-hydroxy-11-tetrahydropyranyloxy-15-(t-butyldimethylsilyloxy)prostanoic acid, methyl ester;
(8R,9S,15R)-9-hydroxy-11-tetrahydropyranyloxy-15-(t-butyldimethylsilyloxy)prostanoic acid, methyl ester;
(8R,9S,15RS)-9-hydroxy-11-tetrahydropyranyloxy-15-(t-butyldimethylsilyloxy)prostanoic acid, methyl ester;
(8R,9S,15RS)-9-hydroxy-11-tetrahydropyranyloxy-15-(t-butyldimethylsilyloxy)-16,20-dimethylprostanoic acid,
(8R,9S,15RS)-9-hydroxy-11-tetrahydropyranyloxy-15-(t-butyldimethylsilyloxy)-16,20-dimethylprostanoic acid, methyl ester;
(8R,9S,15S)-9-hydroxy-11-tetrahydropyranyloxy-15-(t-butyldimethylsilyloxy)-16-penyl-17,18,19,20-tetranorprostanoic acid, methyl ester;
(8R,9S,15RS)-9-hydroxy-11-tetrahydropyranyloxy-15-(t-butyldimethylsilyloxy)-16-phenyl-17,18,19,20-tetranorprostanoic acid, methyl ester;

(8R,9S,15S)-9-hydroxy-11-tetrahydropyranyloxy-15-(t-butyldimethylsilyloxy)-15-cyclopentyl-16,17,18,19,20-pentanorprostanoic acid, methyl ester;

(8R,9S,15RS)-9-hydroxy-11-tetrahydropyranyloxy-15-(t-butyldimethylsilyloxy)-15-cyclopentyl-16,17,18,19,20-pentanorprostanoic acid, methyl ester;

(8R,9S,15S)-9-hydroxy-11-tetrahydropyranyloxy-15-(t-butyldimethylsilyloxy)-16-methyl-16-phenoxy-17,18,19,20-tetranorprostanoic acid, methyl ester;

(8R,9S,15RS)-9-hydroxy-11-tetrahydropyranyloxy-15-(t-butyldimethylsilyloxy)-16-methyl-16-phenoxy-17,18,19,20-tetranorprostanoic acid, methyl ester;

(8R,9S,15S)-9-hydroxy-11-tetrahydropyranyloxy-15-(t-butyldimethylsilyloxy)-16-methylprostanoic acid, methyl ester;

(8R,9S,15RS)-9-hydroxy-11-tetrahydropyranyloxy-15-(t-butyldimethylsilyloxy)-16-methylprostanoic acid, methyl ester;

(8R,9S,15S)-8-methyl-9-hydroxy-11-tetrahydropyranyloxy-15-(t-butyldimethylsilyloxy)-15-cyclohexyl-16,17,18,19,20-pentanorprostanoic acid, methyl ester;

(8R,9S,15RS)-8-methyl-9-hydroxy-11-tetrahydropyranyloxy-15-(t-butyldimethylsilyloxy)-15-cyclohexyl-16,17,18,19,20-pentanorprostanoic acid, methyl ester;

(8R,9S,15S)-8-methyl-9-hydroxy-11-tetrahydropyranyloxy-15-(t-butyldimethylsilyloxy)prostanoic acid, methyl ester;

(8R,9S,15RS)-8-methyl-9-hydroxy-11-tetrahydropyranyloxy-15-(t-butyldimethylsilyloxy)prostanoic acid, methyl ester;

(8R,9S,15S)-9-hydroxy-11-tetrahydropyranyloxy-15-(t-butyldimethylsilyloxy)-15-methyl-15-cyclohexyl-16,17,18,19,20-pentanorprostanoic acid, methyl ester;

(8R,9S,15RS)-9-hydroxy-11-tetrahydropyranyloxy-15-(t-butyldimethylsilyloxy)-15-methyl-15-cyclohexyl-16,17,18,19,20-pentanorprostanoic acid, methyl ester;

(8R,9S,15S)-9-hydroxy-11-tetrahydropyranyloxy-15-(t-butyldimethylsilyloxy)-15-methylprostanoic acid, methyl ester;

(8R,9S,15RS)-9-hydroxy-11-tetrahydropyranyloxy-15-(t-butyldimethylsilyloxy)-15-methylprostanoic acid, methyl ester;

(8R,9S,15S)-8-n-butyl-9-hydroxy-11-tetrahydropyranyloxy-15-(t-butyldimethylsilyloxy)-16-phenoxy-17,18,19,20-tetranorprostanoic acid, methyl ester; and (8R,9S,15RS)-8-n-butyl-9-hydroxy-11-tetrahydropyranyloxy-15-(t-butyldimethylsilyloxy)-16-phenoxy-17,18,19,20-tetranorprostanoic acid, methyl ester.

PREPARATION 15

Preparation of (8R,9S,15S)-9-(4-biphenylcarbonyloxy)-11-tetrahydropyranyloxy-15-(t-butyldimethylsilyloxy)-16-phenoxy-17,18,19,20-tetranorprostanoic acid methyl ester and Related Compounds of Formula (18)

A. Dimethylaminopyridine (825 mg, 6.75 mmol) was added to a solution of 4-biphenylcarbonyl chloride (1.22 g, 5.63 mmol) and (8R,9S,15S)-9-hydroxy-11-tetrahydropyranyloxy-15-(t-butyldimethylsilyloxy)-16-phenoxy-17,18,19,20-tetranorprostanoic acid, methyl ester, the compound of formula (17), (1.365 g, 2.25 mmol) in 15 ml of methylene chloride. After 1 hour the solvent was evaporated and the residue purified by column chromatography (silica gel, hexane/ethyl acetate, 90/10) giving 1.646 g of (8R,9S,15S)-9-(4-biphenylcarbonyloxy)-11-tetrahydropyranyloxy-15-(t-butyldimethylsilyloxy)-16-phenoxy-17,18,19,20-tetranorprostanoic acid, methyl ester, the compound of formula (18).

B. Similarly, following the procedure of A above and replacing (8R,9S,15S)-9-hydroxy-11-tetrahydropyranyloxy-15-(t-butyldimethylsilyloxy)-16-phenoxy-17,18,19,20-tetranorprostanoic acid, methyl ester with the appropriate compound of formula (17), the following compounds of formula (18) are prepared:

(8R,9S,15R)-9-(4-biphenylcarbonyloxy)-11-tetrahydropyranyloxy-15-(t-butyldimethylsilyloxy)-16-phenoxy-17,18,19,20-tetranorprostanoic acid, methyl ester;

(8R,9S,15RS)-9-(4-biphenylcarbonyloxy)-11-tetrahydropyranyloxy-15-(t-butyldimethylsilyloxy)-16-phenoxy-17,18,19,20-tetranorprostanoic acid, methyl ester;

(8R,9S,15S)-8-methyl-9-(4-biphenylcarbonyloxy)-11-tetrahydropyranyloxy-15-(t-butyldimethylsilyloxy)-16-phenoxy-17,18,19,20-tetranorprostanoic acid, methyl ester;

(8R,9S,15S)-9-(4-biphenylcarbonyloxy)-11-tetrahydropyranyloxy-15-(t-butyldimethylsilyloxy)-15-cyclohexyl-16,17,18,19,20-pentanorprostanoic acid, methyl ester;

(8R,9S,15R)-9-(4-biphenylcarbonyloxy)-11-tetrahydropyranyloxy-15-(t-butyldimethylsilyloxy)-15-cyclohexyl-16,17,18,19,20-pentanorprostanoic acid, methyl ester;

(8R,9S,15RS)-9-(4-biphenylcarbonyloxy)-11-tetrahydropyranyloxy-15-(t-butyldimethylsilyloxy)-15-cyclohexyl-16,17,18,19,20-pentanorprostanoic acid, methyl ester;

(8R,9S,15S)-9-(4-biphenylcarbonyloxy)-11-tetrahydropyranyloxy-15-(t-butyldimethylsilyloxy)prostanoic acid, methyl ester;

(8R,9S,15R)-9-(4-biphenylcarbonyloxy)-11-tetrahydropyranyloxy-15-(t-butyldimethylsilyloxy)prostanoic acid, methyl ester;

(8R,9S,15RS)-9-(4-biphenylcarbonyloxy)-11-tetrahydropyranyloxy-15-(t-butyldimethylsilyloxy)prostanoic acid, methyl ester;

(8R,9S,15S)-9-(4-biphenylcarbonyloxy)-11-tetrahydropyranyloxy-15-(t-butyldimethylsilyloxy)-16,20-dimethylprostanoic acid, methyl ester;

(8R,9S,15RS)-9-(4-biphenylcarbonyloxy)-11-tetrahydropyranyloxy-15-(t-butyldimethylsilyloxy)-16,20-dimethylprostanoic acid, methyl ester;

(8R,9S,15S)-9-(4-biphenylcarbonyloxy)-11-tetrahydropyranyloxy-15-(t-butyldimethylsilyloxy)-16-phenyl-17,18,19,20-tetranorprostanoic acid, methyl ester;

(8R,9S,15RS)-9-(4-biphenylcarbonyloxy)-11-tetrahydropyranyloxy-15-(t-butyldimethylsilyloxy)-16-phenyl-17,18,19,20-tetranorprostanoic acid, methyl ester;

(8R,9S,15S)-9-(4-biphenylcarbonyloxy)-11-tetrahydropyranyloxy-15-(t-butyldimethylsilyloxy)-15-cyclopentyl-16,17,18,19,20-pentanorprostanoic acid, methyl ester;

(8R,9S,15RS)-9(4-biphenylcarbonyloxy)-11-tetrahydropyranyloxy-15-(t-butyldimethylsilyloxy)-15-cyclopentyl-16,17,18,19,20-pentanorprostanoic acid, methyl ester;

(8R,9S,15S)-9-(4-biphenylcarbonyloxy)-11-tetrahydropyranyloxy-15-(t-butyldimethylsilyloxy)-16- methyl-16-phenoxy-17,18,19,20-tetranorprostanoic acid, methyl ester;
(8R,9S,15RS)-9-(4-biphenylcarbonyloxy)-11-tetrahydropyranyloxy-15-(t-butyldimethylsilyloxy)-16-methyl-16-phenoxy-17,18,19,20-tetranorprostanoic acid, methyl ester;
(8R,9S,15S)-9-(4-biphenylcarbonyloxy)-11-tetrahydropyranyloxy-15-(t-butyldimethylsilyloxy)-16-methylprostanoic acid, methyl ester;
(8R,9S,15RS)-9-(4-biphenylcarbonyloxy)-11-tetrahydropyranyloxy-15-(t-butyldimethylsilyloxy)-16-methylprostanoic acid, methyl ester;
(8R,9S,15S)-8-methyl-9-(4-biphenylcarbonyloxy)-11-tetrahydropyranyloxy-15-(t-butyldimethylsilyloxy)-15-cyclohexyl-16,17,18,19,20-pentanorprostanoic acid, methyl ester;
(8R,9S,15RS)-8-methyl-9(4-biphenylcarbonyloxy)-11-tetrahydropyranyloxy-15-(t-butyldimethylsilyloxy)-15-cyclohexyl-16,17,18,19,20-pentanorprostanoic acid, methyl ester;
(8R,9S,15S)-8-methyl-9-(4-biphenylcarbonyloxy)-11-tetrahydropyranyloxy-15-(t-butyldimethylsilyloxy)-prostanoic acid, methyl ester;
(8R,9S,15RS)-8-methyl-9-(4-biphenylcarbonyloxy)-11-tetrahydropyranyloxy-15-(t-butyldimethylsilyloxy)-prostanoic acid, methyl ester;
(8R,9S,15S)-9-(4-biphenylcarbonyloxy)-11-tetrahydropyranyloxy-15-(t-butyldimethylsilyloxy)-15-methyl-15-cyclohexyl-16,17,18,19,20-pentanorprostanoic acid, methyl ester;
(8R,9S,15RS)-9-(4-biphenylcarbonyloxy)-11-tetrahydropyranyloxy-15-(t-butyldimethylsilyloxy)-15-methyl-15-cyclohexyl-16,17,18,19,20-pentanorprostanoic acid, methyl ester;
(8R,9S,15S)-9-(4-biphenylcarbonyloxy)-11-tetrahydropyranyloxy-15-(t-butyldimethylsilyloxy)-15-methylprostanoic acid, methyl ester;
(8R,9S,15RS)-9-(4-biphenylcarbonyloxy)-11-tetrahydropyranyloxy-15-(t-butyldimethylsilyloxy)-15-methylprostanoic acid, methyl ester;
(8R,9S,15S)-8-n-butyl-9-(4-biphenylcarbonyloxy)-11-tetrahydropyranyloxy-15-(t-butyldimethylsilyloxy)-16-phenoxy-17,18,19,20-tetranorprostanoic acid, methyl ester; and
(8R,9S,15RS)-8-n-butyl-9-(4-biphenylcarbonyloxy)-11-tetrahydropyranyloxy-15-(t-butyldimethylsilyloxy)-16-phenoxy-17,18,19,20-tetranorprostanoic acid, methyl ester.

PREPARATION 16

Preparation of (8R,9S,15S)-9-(4-biphenylcarbonyloxy)-11-hydroxy-15-(t-butyldimethylsilyloxy)-16-phenoxy-17,18,19,20-tetranorprostanoic acid, methyl ester and Related Compounds of Formula (19)

A. Magnesium bromide etherate (1.438 g, 6.3 mmol) was added to a solution of (8R,9S,15S)-9-(4-biphenylcarbonyloxy)-11-tetrahydropyranyloxy-15-(t-butyldimethylsilyloxy)-16-phenoxy-17,18,19,20-tetranorprostanoic acid, methyl ester, the compound of formula (18), (1.646 g, 2.1 mmol) in 5 ml of anhydrous ether, and the mixture was stirred for 2 hours at room temperature. It was then cooled to 0° C. and 20 ml of ice-cold water was added. The phases were separated and the aqueous phase extracted with ethyl acetate (3×20 ml). The combined organic extracts were dried (anhydrous magnesium sulfate) and evaporated. The residue was purified by column chromatography (silica gel, hexane/ethyl acetate, 85/15) giving 1.377 g of (8R,9S,15S)-9-(4-biphenylcarbonyloxy)-11-hydroxy-15-(t-butyldimethylsilyloxy)-16-phenoxy-17,18,19,20-tetranorprostanoic acid, methyl ester, the compound of formula (19).

B. Similarly, following the procedure of A above and replacing (8R,9S,15S)-9-(4-biphenylcarbonyloxy)-11-tetrahydropyranyloxy-15-(t-butyldimethylsilyloxy)-16-phenoxy-17,18,19,20 -tetranorprostanoic acid, methyl ester with the appropriate compound of formula (18), the following compounds of formula (19) are prepared:
(8R,9S,15R)-9-(4-biphenylcarbonyloxy)-11-hydroxy-15-(t-butyldimethylsilyloxy)-16-phenoxy-17,18,19,20-tetranorprostanoic acid, methyl ester;
(8R,9S,15RS)-9-(4-biphenylcarbonyloxy)-11-hydroxy-15-(t-butyldimethylsilyloxy)-16-phenoxy-17,18,19,20-tetranorprostanoic acid, methyl ester;
(8R,9S,15S)-8-methyl-9-(4-biphenylcarbonyloxy)-11-hydroxy-15-(t-butyldimethylsilyloxy)-16-phenoxy-17,18,19,20-tetranorprostanoic acid, methyl ester;
(8R,9S,15S)-9-(4-biphenylcarbonyloxy)-11-hydroxy-15-(t-butyldimethylsilyloxy)-15-cyclohexyl-16,17,18,19,20-pentanorprostanoic acid, methyl ester;
(8R,9S,15R)-9-(4-biphenylcarbonyloxy)-11-hydroxy-15-(t-butyldimethylsilyloxy)-15-cyclohexyl-16,17,18,19,20-pentanorprostanoic acid, methyl ester;
(8R,9S,15RS)-9-(4-biphenylcarbonyloxy)-11-hydroxy-15-(t-butyldimethylsilyloxy)-15-cyclohexyl-16,17,18,19,20-pentanorprostanoic acid, methyl ester;
(8R,9S,15S)-9-(4-biphenylcarbonyloxy)-11-hydroxy-15-(t-butyldimethylsilyloxy)prostanoic acid, methyl ester;
(8R,9S,15R)-9-(4-biphenylcarbonyloxy)-11-hydroxy-15-(t-butyldimethylsilyloxy)prostanoic acid, methyl ester;
(8R,9S,15RS)-9-(4-biphenylcarbonyloxy)-11-hydroxy-15-(t-butyldimethylsilyloxy)prostanoic acid, methyl ester;
(8R,9S,15S)-9-(4-biphenylcarbonyloxy)-11-hydroxy-15-(t-butyldimethylsilyloxy)-16,20-dimethylprostanoic acid, methyl ester;
(8R,9S,15RS)-9-(4-biphenylcarbonyloxy)-11-hydroxy-15-(t-butyldimethylsilyloxy)-16,20-dimethylprostanoic acid, methyl ester;
(8R,9S,15S)-9-(4-biphenylcarbonyloxy)-11-hydroxy-15-(t-butyldimethylsilyloxy)-16-phenyl-17,18,19,20-tetranorprostanoic acid, methyl ester;
(8R,9S,15RS)-9-(4-biphenylcarbonyloxy)-11-hydroxy-15-(t-butyldimethylsilyloxy)-16-phenyl-17,18,19,20-tetranorprostanoic acid, methyl ester;
(8R,9S,15S)-9(4-biphenylcarbonyloxy)-11-hydroxy-15-(t-butyldimethylsilyloxy)-15-cyclopentyl-16,17,18,19,20-pentanorprostanoic acid, methyl ester;
(8R,9S,15RS)-9-(4-biphenylcarbonyloxy)-11-hydroxy-15-(t-butyldimethylsilyloxy)-15-cyclopentyl-16,17,18,19,20-pentanorprostanoic acid, methyl ester;
(8R,9S,15S)-9-(4-biphenylcarbonyloxy)-11-hydroxy-15-(t-butyldimethylsilyloxy)-16-methyl-16-phenoxy-17,18,19,20-tetranorprostanoic acid, methyl ester;
(8R,9S,15RS)-9-(4-biphenylcarbonyloxy)-11-hydroxy-15-(t-butyldimethylsilyloxy)-16-methyl-16-phenoxy-17,18,19,20-tetranorprostanoic acid, methyl ester;
(8R,9S,15S)-9-(4-biphenylcarbonyloxy)-11-hydroxy-15-(t-butyldimethylsilyloxy)-16-methylprostanoic acid, methyl ester;
(8R,9S,15RS)-9-(4-biphenylcarbonyloxy)-11-hydroxy-15-(t-butyldimethylsilyloxy)-16-methylprostanoic acid, methyl ester;

(8R,9S,15S)-8-methyl-9-(4-biphenylcarbonyloxy)-11-hydroxy-15-(t-butyldimethylsilyloxy)-15-cyclohexyl-16,17,18,19,20-pentanorprostanoic acid, methyl ester;

(8R,9S,15RS)-8-methyl-9-(4-biphenylcarbonyloxy)-11-hydroxy-15-(t-butyldimethylsilyloxy)-15-cyclohexyl-16,17,18,19,20-pentanorprostanoic acid, methyl ester;

(8R,9S,15S)-8-methyl-9-(4-biphenylcarbonyloxy)-11-hydroxy-15-(t-butyldimethylsilyloxy)prostanoic acid, methyl ester;

(8R,9S,15RS)-8-methyl-9-(4-biphenylcarbonyloxy)-11-hydroxy-15-(t-butyldimethylsilyloxy)prostanoic acid, methyl ester;

(8R,9S,15S)-9-(4-biphenylcarbonyloxy)-11-hydroxy-15-(t-butyldimethylsilyloxy)-15-methyl-15-cyclohexyl-16,17,18,19,20-pentanorprostanoic acid, methyl ester;

(8R,9S,15RS)-9-(4-biphenylcarbonyloxy)-11-hydroxy-15-(t-butyldimethylsilyloxy)-15-methyl-15-cyclohexyl-16,17,18,19,20-pentanorprostanoic acid, methyl ester;

(8R,9S,15S)-9-(4-biphenylcarbonyloxy)-11-hydroxy-15-(t-butyldimethylsilyloxy)-15-methylprostanoic acid, methyl ester;

(8R,9S,15RS)-9-(4-biphenylcarbonyloxy)-11-hydroxy-15-(t-butyldimethylsilyloxy)-15-methylprostanoic acid, methyl ester;

(8R,9S,15S)-8-n-butyl-9-(4-biphenylcarbonyloxy)-11-hydroxy-15-(t-butyldimethylsilyloxy)-16-phenoxy-17,18,19,20-tetranorprostanoic acid, methyl ester; and (8R,9S,15RS)-8-n-butyl-9-(4-biphenylcarbonyloxy)-11-hydroxy-15-(t-butyldimethylsilyloxy)-16-phenoxy-17,18,19,20-tetranorprostanoic acid, methyl ester.

PREPARATION 17

Preparation of
(8R,9S,15S)-9-(4-biphenylcarbonyloxy)-15-(t-butyldimethylsilyloxy)-16-phenoxy-17,18,19,20-tetranorprosta-11-enoic acid, methyl ester and Related Compounds of Formula (20)

A. Trifluoromethanesulfonic anhydride (0.46 ml, 2.73 mmol) was added dropwise at −20° C. to a solution of (8R,9S,15S)-9-(4-biphenylcarbonyloxy)-11-hydroxy-15-(t-butyldimethylsilyloxy)-16-phenoxy-17,18,19,20-tetranorprostanoic acid, methyl ester, the compound of formula (19), (1.28 g, 1.82 mmol) and 2,4,6-collidine (0.74 g, 6.1 mmol) in 4 ml of dry methylene chloride. After stirring for 10 min at −20° C., the temperature was allowed to reach 20° C. over a period of 2 hrs and stirred for 1 hour more. It was then poured into water (50 ml) and extracted with methylene chloride (3×30 ml). The combined organic extracts were washed with 10% hydrochloric acid (30 ml) and saturated sodium bicarbonate (30 ml), dried over anhydrous magnesium sulfate and the solvent removed under reduced pressure. The residue was purified by column chromatography (silica gel, hexane/ethyl acetate, 80/20) giving (8R,9S,15S)-9-(4-biphenylcarbonyloxy)-15-(t-butyldimethylsilyloxy)-16-phenoxy-17,18,19,20-tetranorprosta-11-enoic acid, methyl ester, the compound of formula (20), 716 mg. B. Similarly, following the procedure of A above and replacing (8R,9S,15S)-9-(4-biphenylcarbonyloxy)-11-hydroxy-15-(t-butyldimethylsilyloxy)-16-phenoxy-17,18,19,20-tetranorprostanoic acid, methyl ester with the appropriate compound of formula (19), the following compounds of formula (20) are prepared:

(8R,9S,15R)-9-(4-biphenylcarbonyloxy)-15-(t-butyldimethylsilyloxy)-16-phenoxy-17,18,19,20-tetranorprosta-11-enoic acid, methyl ester;

(8R,9S,15RS)-9-(4-biphenylcarbonyloxy)-15-(t-butyldimethylsilyloxy)-16-phenoxy-17,18,19,20-tetranorprosta-11-enoic acid, methyl ester;

(8R,9S,15S)-8-methyl-9-(4-biphenylcarbonyloxy)-15-(t-butyldimethylsilyloxy)-16-phenoxy-17,18,19,20-tetranorprosta-11-enoic acid, methyl ester;

(8R,9S,15S)-9-(4-biphenylcarbonyloxy)-15-(t-butyldimethylsilyloxy)-15-cyclohexyl-16,17,18,19,20-pentanorprosta-11-enoic acid, methyl ester;

(8R,9S,15R)-9-(4-biphenylcarbonyloxy)-15-(t-butyldimethylsilyloxy)-15-cyclohexyl-16,17,18,19,20-pentanorprosta-11-enoic acid, methyl ester;

(8R,9S,15RS)-9-(4-biphenylcarbonyloxy)-15-(t-butyldimethylsilyloxy)-15-cyclohexyl-16,17,18,19,20-pentanorprosta-11-enoic acid, methyl ester;

(8R,9S,15S)-9-(4-biphenylcarbonyloxy)-15-(t-butyldimethylsilyloxy)prosta-11-enoic acid, methyl ester;

(8R,9S,15R)-9-(4-biphenylcarbonyloxy)-15-(t-butyldimethylsilyloxy)prosta-11-enoic acid, methyl ester;

(8R,9S,15RS)-9-(4-biphenylcarbonyloxy)-15-(t-butyldimethylsilyloxy)prosta-11-enoic acid, methyl ester;

(8R,9S,15S)-9-(4-biphenylcarbonyloxy)-15-(t-butyldimethylsilyloxy)-16,20-dimethylprosta-11-enoic acid, methyl ester;

(8R,9S,15RS)-9-(4-biphenylcarbonyloxy)-15-(t-butyldimethylsilyloxy)-16,20-dimethylprosta-11-enoic acid, methyl ester;

(8R,9S,15S)-9-(4-biphenylcarbonyloxy)-15-(t-butyldimethylsilyloxy)-16-phenyl-17,18,19,20-tetranorprosta-11-enoic acid, methyl ester;

(8R,9S,15RS)-9-(4-biphenylcarbonyloxy)-15-(t-butyldimethylsilyloxy)-16-phenyl-17,18,19,20-tetranorprosta-11-enoic acid, methyl ester;

(8R,9S,15S)-9-(4-biphenylcarbonyloxy)-15-(t-butyldimethylsilyloxy)-15-cyclopentyl-16,17,18,19,20-pentanorprosta-11-enoic acid, methyl ester;

(8R,9S,15RS)-9-(4-biphenylcarbonyloxy)-15-(t-butyldimethylsilyloxy)-15-cyclopentyl-16,17,18,19,20-pentanorprosta-11-enoic acid, methyl ester;

(8R,9S,15S)-9-(4-biphenylcarbonyloxy)-15-(t-butyldimethylsilyloxy)-16-methyl-16-phenoxy-17,18,19,20-tetranorprosta-11-enoic acid, methyl ester;

(8R,9S,15RS)-9-(4-biphenylcarbonyloxy)-15-(t-butyldimethylsilyloxy)-16-methyl-16-phenoxy-17,18,19,20-tetranorprosta-11-enoic acid, methyl ester;

(8R,9S,15S)-9-(4-biphenylcarbonyloxy)-15-(t-butyldimethylsilyloxy)-16-methylprosta-11-enoic acid, methyl ester;

(8R,9S,15RS)-9-(4-biphenylcarbonyloxy)-15-(t-butyldimethylsilyloxy)-16-methylprosta-11-enoic acid, methyl ester;

(8R,9S,15S)-8-methyl-9-(4-biphenylcarbonyloxy)15-(t-butyldimethylsilyloxy)-15-cyclohexyl-16,17,18,19,20-pentanorprosta-11-enoic acid, methyl ester;

(8R,9S,15RS)-8-methyl-9-(4-biphenylcarbonyloxy)-15-(t-butyldimethylsilyloxy)-15-cyclohexyl-16,17,18,19,20-pentanorprosta-11-enoic acid, methyl ester;

(8R,9S,15S)-8-methyl-9-(4-biphenylcarbonyloxy)-15-(t-butyldimethylsilyloxy)prosta-11-enoic acid, methyl ester;

(8R,9S,15RS)-8-methyl-9-(4-biphenylcarbonyloxy)-15-(t-butyldimethylsilyloxy)prosta-11-enoic acid, methyl ester;
(8R,9S,15S)-9-(4-biphenylcarbonyloxy)-15-(t-butyldimethylsilyloxy)-15-methyl-15-cyclohexyl-16,17,18,19,20-pentanorprosta-11-enoic acid, methyl ester;
(8R,9S,15RS)-9-(4-biphenylcarbonyloxy)-15-(t-butyldimethylsilyloxy)-15-methyl-15-cyclohexyl-16,17,18,19,20-pentanorprosta-11-enoic acid, methyl ester;
(8R,9S,15S)-9-(4-biphenylcarbonyloxy)-15-(t-butyldimethylsilyloxy)-15-methylprosta-11-enoic acid, methyl ester;
(8R,9S,15RS)-9-(4-biphenylcarbonyloxy)-15-(t-butyldimethylsilyloxy)-15-methylprosta-11-enoic acid, methyl ester;
(8R,9S,15S)-8-n-butyl-9-(4-biphenylcarbonyloxy)-15-(t-butyldimethylsilyloxy)-16-phenoxy-17,18,19,20-tetranorprosta-11-enoic acid, methyl ester; and
(8R,9S,15RS)-8-n-butyl-9-(4-biphenylcarbonyloxy)-15-(t-butyldimethylsilyloxy)-16-phenoxy-17,18,19,20-tetranorprosta-11-enoic acid, methyl ester.

PREPARATION 18

Preparation of (8R,9S,15S)-9-hydroxy-15-(t-butyldimethylsilyloxy)-16-phenoxy-17,18,19,20-tetranorprosta-11-enoic acid, methyl ester and Related Compounds of Formula (7) where X is —CH$_2$CH$_2$—and m is 3

A. A suspension of (8R,9S,15S)-9-(4-biphenylcarbonyloxy)-15-(t-butyldimethylsilyloxy)-16-phenoxy-17,18,19,20-tetranorprosta-11-enoic acid, methyl ester, the compound of formula (20), (600 mg, 0.88 mmol) in 5 ml of methanol was stirred for 48 hrs with anhydrous potassium carbonate (363 mg, 2.63 mmol) at room temperature. Then the mixture was poured into 50 ml of ice-water and acidified with 20% aqueous oxalic acid (20 ml). After extraction with ethyl acetate (3 times 50 ml) the combined extracts were dried with anhydrous magnesium sulfate and the solvent removed under reduced pressure. The residue was purified by column chromatography (silica gel, hexane/ethyl acetate, 85/15) giving (8R,9S,15S)-9-hydroxy-15-(t-butyldimethylsilyloxy)-16-phenoxy-17,18,19,20-tetranorprosta-11-enoic acid, methyl ester, the compound of formula (7) where X is —CH$_2$CH$_2$—and m is 3, 295 mg.

B. Similarly, following the procedure of A above and replacing (8R,9S,15S)-9-(4-biphenylcarbonyloxy)-15-(t-butyldimethylsilyloxy)-16-phenoxy-17,18,19,20-tetranorprosta-11-enoic acid, methyl ester with the appropriate compound of formula (20), the following compounds of formula (7) where X is —CH$_2$CH$_2$13 and m is 3 are prepared:
(8R,9S,15R)-9-hydroxy-15-(t-butyldimethylsilyloxy)-16-phenoxy-17,18,19,20-tetranorprosta-11-enoic acid, methyl ester;
(8R,9S,15RS)-9-hydroxy-15-(t-butyldimethylsilyloxy)-16-phenoxy-17,18,19,20-tetranorprosta-11-enoic acid, methyl ester;
(8R,9S,15S)-8-methyl-9-hydroxy-15-(t-butyldimethylsilyloxy)-16-phenoxy-17,18,19,20-tetranorprosta-11-enoic acid, methyl ester;
(8R,9S,15S)-9-hydroxy-15-(t-butyldimethylsilyloxy)-15-cyclohexyl-16,17,18,19,20-pentanorprosta-11-enoic acid, methyl ester;
(8R,9S,15R)-9-hydroxy-15-(t-butyldimethylsilyloxy)-15-cyclohexyl-16,17,18,19,20-pentanorprosta-11-enoic acid, methyl ester;
(8R,9S,15RS)-9-hydroxy-15-(t-butyldimethylsilyloxy)-15-cyclohexyl-16,17,18,19,20-pentanorprosta-11-enoic acid, methyl ester;
(8R,9S,15S)-9-hydroxy-15-(t-butyldimethylsilyloxy)-prosta-11-enoic acid, methyl ester;
(8R,9S,15R)-9-hydroxy-15-(t-butyldimethylsilyloxy)-prosta-11-enoic acid, methyl ester;
(8R,9S,15RS)-9-hydroxy-15-(t-butyldimethylsilyloxy)-prosta-11-enoic acid, methyl ester;
(8R,9S,15S)-9-hydroxy-15-(t-butyldimethylsilyloxy)-16,20-dimethylprosta-11-enoic acid, methyl ester;
(8R,9S,15RS)-9-hydroxy-15-(t-butyldimethylsilyloxy)-16,20-dimethylprosta-11-enoic acid, methyl ester;
(8R,9S,15S)-9-hydroxy-15-(t-butyldimethylsilyloxy)-16-phenyl-17,18,19,20-tetranorprosta-11-enoic acid, methyl ester;
(8R,9S,15RS)-9-hydroxy-15-(t-butyldimethylsilyloxy)-16-phenyl-17,18,19,20-tetranorprosta-11-enoic acid, methyl ester;
(8R,9S,15S)-9-hydroxy-15-(t-butyldimethylsilyloxy)-15-cyclopentyl-16,17,18,19,20-pentanorprosta-11-enoic acid, methyl ester;
(8R,9S,15RS)-9-hydroxy-15-(t-butyldimethylsilyloxy)-15-cyclopentyl-16,17,18,19,20-pentanorprosta-11-enoic acid, methyl ester;
(8R,9S,15S)-9-hydroxy-15-(t-butyldimethylsilyloxy)-16-methyl-16-phenoxy-17,18,19,20-tetranorprosta-11-enoic acid, methyl ester;
(8R,9S,15RS)-9-hydroxy-15-(t-butyldimethylsilyloxy)-16-methyl-16-phenoxy-17,18,19,20-tetranorprosta-11-enoic acid, methyl ester;
(8R,9S,15S)-9-hydroxy-15-(t-butyldimethylsilyloxy)-16-methylprosta-11-enoic acid, methyl ester;
(8R,9S,15RS)-9-hydroxy-15-(t-butyldimethylsilyloxy)-16-methylprosta-11-enoic acid, methyl ester;
(8R,9S,15S)-8-methyl-9-hydroxy-15-(t-butyldimethylsilyloxy)-15-cyclohexyl-16,17,18,19,20-pentanorprosta-11-enoic acid, methyl ester;
(8R,9S,15RS)-8-methyl-9-hydroxy-15-(t-butyldimethylsilyloxy)-15-cyclohexyl-16,17,18,19,20-pentanorprosta-11-enoic acid, methyl ester;
(8R,9S,15S)-8-methyl-9-hydroxy-15-(t-butyldimethylsilyloxy)prosta-11-enoic acid, methyl ester;
(8R,9S,15RS)-8-methyl-9-hydroxy-15-(t-butyldimethylsilyloxy)prosta-11-enoic acid, methyl ester;
(8R,9S,15S)-9-hydroxy-15-(t-butyldimethylsilyloxy)-15-methyl-15-cyclohexyl-16,17,18,19,20-pentanorprosta-11-enoic acid, methyl ester;
(8R,9S,15RS)-9-hydroxy-15-(t-butyldimethylsilyloxy)-15-methyl-15-cyclohexyl-16,17,18,19,20-pentanorprosta-11-enoic acid, methyl ester;
(8R,9S,15S)-9-hydroxy-15-(t-butyldimethylsilyloxy)-15-methylprosta-11-enoic acid, methyl ester;
(8R,9S,15RS)-9-hydroxy-15-(t-butyldimethylsilyloxy)-15-methylprosta-11-enoic acid, methyl ester;
(8R,9S,15S)-8-n-butyl-9-hydroxy-15-(t-butyldimethylsilyloxy)-16-phenoxy-17,18,19,20-tetranorprosta-11-enoic acid, methyl ester; and
(8R,9S,15RS)-8-n-butyl-9-hydroxy-15-(t-butyldimethylsilyloxy)-16-phenoxy-17,18,19,20-tetranorprosta-11-enoic acid, methyl ester.

PREPARATION 19

Preparation of
(1S,2R,3'S)-3-[3'-(t-butyldimethylsilyloxy)-4'-phenoxybut-1'-yl]-1-hydroxy-2-(prop-1-en-3-yl)cyclopent-3-ene and Related Compounds of Formula (21)

A. To a solution of diisobutylaluminum hydride in toluene (0.12 ml of a 1.98 M solution, 2.38 mmol) was added at −76° C. a solution of [(1S,2R,3'S)-3-(3'-t-butyldimethylsilyloxy-4'-phenoxybut-1'-yl)-1-hydroxycyclopent-3-en-2-yl]acetic acid, Y-lactone, the compound of formula (6) (490 mg, 1.217 mmol), in 10 ml of toluene. After 30 minutes, methanol (1.5 ml) was added dropwise followed by 3 drops of saturated aqueous sodium chloride solution and 5 ml of ethyl acetate. The cooling bath was removed and the mixture was stirred at room temperature until a gel formed. Then the mixture was filtered through Celite and the filtrate evaporated. The residue was dissolved in 5 ml of tetrahydrofuran and 1.4 ml of a solution of methylidenephosphorane (0.86 M in tetrahydrofuran, 1.22 mmol) was added. After 30 minutes, the mixture was poured into saturated ammonium chloride (10 ml), the phases were separated and the aqueous phase was extracted with ether (3×10 ml). The combined organic extracts were dried (anhydrous magnesium sulfate) and evaporated. The residue was purified by column chromatography (silica gel, benzene/ethyl acetate, 95/5), giving 488 mg of (1S,2R,3'S)-3-[3'-(t-butyldimethylsilyloxy)-4'-phenoxybut-1'-yl]-1-hydroxy-2-(prop-1-en-3-yl)cyclopent-3-ene, the compound of formula (21).

B. Similarly, following the procedure of A above and replacing [(1S,2R,3'S)-3-(3'-t-butyldimethylsilyloxy-4'-phenoxybut-1'-yl)-1-hydroxycyclopent-3-en-2-yl]acetic acid, Y-lactone, with the appropriate compound of formula (6), the following compounds of formula (21) are prepared:

[(1S,2R,3'R)-3-(3'-t-butyldimethylsilyloxy-4'-phenoxybut-1'-yl)-1-hydroxy-2-(prop-1-en-3-yl)cyclopent-3-ene;

[(1S,2R,3'RS)-3-(3'-t-butyldimethylsilyloxy-4'-phenoxybut-1'-yl)-1-hydroxy-2-(prop-1-en-3-yl)cyclopent-3-ene;

[(1S,2R,3'S)-3-(3'-t-butyldimethylsilyloxy-3'-cyclohexylprop-1'-yl)-1-hydroxy-2-(prop-1-en-3-yl)-cyclopent-3-ene;

[(1S,2R,3'R)-3-(3'-t-butyldimethylsilyloxy-3'-cyclohexylprop-1-hydroxy-2-(prop-1-en-3-yl)cyclopent-3-ene;

[(1S,2R,3'RS)-3-(3'-t-butyldimethylsilyloxy-3'-cyclohexylprop-1'-yl)-1-hydroxy-2-(prop-1-en-3-yl)cyclopent-3-ene;

[(1S,2R,3'S)-3-(3'-t-butyldimethylsilyloxyoct-1'-yl)-1-hydroxy-2-(prop-1-en-3-yl)cyclopent-3-ene;

[(1S,2R,3'R)-3-(3'-t-butyldimethylsilyloxyoct-1'-yl)-1-hydroxy-2-(prop-1-en-3-yl)cyclopent-3-ene;

[(1S,2R,3'RS)-3-(3'-t-butyldimethylsilyloxyoct-1'-yl)-1-hydroxy-2-(prop-1-en-3-yl)cyclopent-3-ene;

[(1S,2R,3'S)-3-(3'-t-butyldimethylsilyloxy-4'-methylnon-1'-yl)-1-hydroxy-2-(prop-1-en-3-yl)cyclopent-3-ene;

[(1S,2R,3'RS)-3-(3'-t-butyldimethylsilyloxy-4'-methylnon-1'-yl)-1-hydroxy-2-(prop-1-en-3-yl)cyclopent-3-ene;

[(1S,2R,3'S)-3-(3'-t-butyldimethylsilyloxy-4'-phenylbut-1'-yl)-1-hydroxy-2-(prop-1-en-3-yl)cyclopent-3-ene;

[(1S,2R,3'RS)-3-(3'-t-butyldimethylsilyloxy-4'-phenylbut-1'-yl)-1-hydroxy-2-(prop-1-en-3-yl)cyclopent-3-ene;

[(1S,2R,3'S)-3-(3'-t-butyldimethylsilyloxy-4'-cyclopentylprop-1'-yl)-1-hydroxy-2-(prop-1-en-3-yl)cyclopent-3-ene;

[(1S,2R,3'RS)-3-(3'-t-butyldimethylsilyloxy-4'-cyclopentylprop-1'-yl)-1-hydroxy-2-(prop-1-en-3-yl)cyclopent-3-ene;

[(1S,2R,3'S)-3-(3'-t-butyldimethylsilyloxy-4'-methyl-4'-phenoxybut-1'-yl)-1-hydroxy-2

[(1S,2R,3'RS)-3-(3'-t-butyldimethylsilyloxy-4'-methyl-4'-phenoxybut-1'-yl)-1-hydroxy-2-(prop-1-en-3-yl)cyclopent-3-ene; cyclopent-3-ene;

[(1S,2R,3'S)-3-(3'-t-butyldimethylsilyloxy-4'-methyloct-1'-yl)-1-hydroxy-2-(prop-1-en-3-yl)cyclopent-3-ene;

[(1S,2R,3'RS)-3-(3'-t-butyldimethylsilyloxy-4'-methyloct-1'-yl)-1-hydroxy-2-(prop-1-en-3-yl)cyclopent-3-ene;

[(1S,2R,3'S)-3-(3'-t-butyldimethylsilyloxy-3'-methyl-3'-cyclohexylprop-1'-yl)-1-hydroxy-2-(prop-1-en-3-yl)-cyclopent-3-ene;

[(1S,2R,3'RS)-3-(3'-t-butyldimethylsilyloxy-3'-methyl-3'-cyclohexylprop-1'-yl)-1-hydroxy-2-(prop-1-en-3-yl)cyclopent-3-ene;

[(1S,2R,3'S)-3-(3'-t-butyldimethylsilyloxy-3'-methyloct-1'-yl)-1-hydroxy-2-(prop-1-en-3-yl)cyclopent-3-ene;

[(1S,2R,3'RS)-3-(3'-t-butyldimethylsilyloxy-3'-methyloct-1'-yl)-1-hydroxy-2-(prop-1-en-3-yl)cyclopent-3-ene.

[(±)-3-(3'-t-butyldimethylsilyloxy-4'-phenoxybut-1'-yl)-1-hydroxy-2-(prop-1-en-3-yl)cyclopent-3-ene;

[(1S,2R,3RS)-3-(3'-t-butyldimethylsilyloxy-4'-phenoxybut-1'-yl)-1-hydroxy-2-methyl-2-(prop-1-en-3-yl)cyclopent-3-ene;

[(±)-3-(3'-t-butyldimethylsilyloxy-3'-cyclohexylprop-1'-yl)-1-hydroxy-2-(prop-1-en-3-yl)cyclopent-3-ene;

[(±)-3-(3'-t-butyldimethylsilyloxyoct-1'-yl)-1-hydroxy-2-(prop-1-en-3-yl)cyclopent-3-ene;

[(±)-3-(3'-t-butyldimethylsilyloxy-4'-phenylbut-1'-yl)-1-hydroxy-2-(prop-1-en-3-yl)cyclopent-3-ene;

[(±)-3-(3'-t-butyldimethylsilyloxy-4'-methylnon-1'-yl)-1-hydroxy-2-(prop-1-en-3-yl)-cyclopent-3-ene;

[(±)-3-(3'-t-butyldimethylsilyloxydodec-1'-yl)-1-hydroxy-2-(prop-1-en-3-yl)cyclopent-3-ene;

[(±)-3-(3'-t-butyldimethylsilyloxy-8', 8',8'-trifluorooct-1'-yl)-1-hydroxy-2-(prop-1-en-3-yl)-cyclopent-3-ene;

[(±)-3-(3'-t-butyldimethylsilyloxy-3'-cyclopentylprop-1'-yl)-1-hydroxy-2-(prop-1-en-3-yl)cyclopent-3-ene;

[(±)-3-(3'-t-butyldimethylsilyloxy-4'-methyl-4'-phenoxybut-1'-yl)-1-hydroxy-2-(prop-1-en-3-yl)cyclopent-3-ene;

[(±)-3-(3'-t-butyldimethylsilyloxy-4'-methyl-4'-oct-1'-yl)-1-hydroxy-2-(prop-1-en-3-yl)cyclopent-3-ene;

[(1S,2R,3'RS)-3-(3'-t-butyldimethylsilyloxy-3'-cyclohexylprop-1'-yl)-1-hydroxy-2-methyl-2-(prop-1-en-3-yl)cyclopent-3-ene;

[(1S,2R,3'RS)-3-(3'-t-butyldimethylsilyloxyoct-1'-yl)-1-hydroxy-2-methyl-2-(prop-1-en-3-yl)cyclopent-3-ene;

[(±)-3-(3'-t-butyldimethylsilyloxy-3'-methyl-3'-cyclohexylprop-1'-yl)-1-hydroxy-2-(prop-1-en-3-yl)cyclopent-3-ene;

[(±)-3-(3'-t-butyldimethylsilyloxy-3'-methyloct-1'-yl)-1-hydroxy-2-(prop-1-en-3-yl)cyclopent-3-ene; and

[(1S,2R,3'RS)-3-(3'-t-butyldimethylsilyloxy-4'-phenoxybut-1'-yl)-1-hydroxy-2-n-butyl-2-(prop-1-en-3-yl)cyclopent-3-ene.

PREPARATION 20

Preparation of
(1S,2R,3'S)-3-[3'-(t-butyldimethylsilyloxy)-4'-phenoxybut-1'-yl]-1-(triethylsilyloxy)-2-(prop-1-en-3-yl)cyclopent-3-ene and Related Compounds of Formula (22)

A. Imidazole (0.29 g, 4.2 mmol) and triethylchlorosilane (0.32 g, 2.1 mmol) were added to a solution of (1S,2R,3'S)-3-[3'-(t-butyldimethylsilyloxy)-4'-phenoxybut-1'-yl]-1-hydroxy-2-(prop-1-en-3-yl)cyclopent-3-ene, the compound of formula (21), (0.48 g, 1.2 mmol) in 6 ml of N,N-dimethylformamide and stirred at room temperature. After 3 hrs, the mixture was poured into 10 ml of water and extracted with benzene (5×10 ml). The combined organic extracts were washed with water (20 ml), dried over anhydrous magnesium sulfate and the solvent removed under reduced pressure, giving (1S,2R,3'S)-3-[3'-(t-butyldimethylsilyloxy)-4'-phenoxybut-1'-yl]-1-(triethylsilyloxy)-2-(prop-1-en-3-yl)cyclopent-3-ene, the compound of formula (22).

B. Similarly, following the procedure of A above and replacing (1S,2R,3'S)-3-[3'-(t-butyldimethylsilyloxy)-4'-phenoxybut-1'-yl]-1-hydroxy-2-(prop-1-en-3-yl)cyclopent-3-ene with the appropriate compound of formula (21), the following compounds of formula (22) are prepared:

[(1S,2R,3'R)-3-(3'-t-butyldimethylsilyloxy-4'-phenoxybut-1'-yl)-1-(triethylsilyloxy)-2-(prop-1-en-3-yl)cyclopent-3-ene;

[(1S,2R,3'RS)-3-(3'-t-butyldimethylsilyloxy-4'-phenoxybut-1'-yl)-1-(triethylsilyloxy)-2-(prop-1-en-3-yl)cyclopent-3-ene;

[(1S,2R,3'S)-3-(3'-t-butyldimethylsilyloxy-3'-cyclohexylprop-1'-yl)-1-(triethylsilyloxy)-2-(prop-1-en-3-yl)cyclopent-3-ene;

[(1S,2R,3'R)-3-(3'-t-butyldimethylsilyloxy-3'-cyclohexylprop-1'-yl)-1-(triethylsilyloxy)-2-(prop-1-en-3-yl)cyclopent-3-ene;

[(1S,2R,3'RS)-3-(3'-t-butyldimethylsilyloxy-3'-cyclohexylprop-1'-yl)-1-(triethylsilyloxy)-2-(prop-1-en-3-yl)cyclopent-3-ene;

[(1S,2R,3'S)-3-(3'-t-butyldimethylsilyloxyoct-1'-yl)-1-(triethylsilyloxy)-2-(prop-1-en-3-yl)cyclopent-3-ene;

[(1S,2R,3'R)-3-(3'-t-butyldimethylsilyloxyoct-1'-yl)-1-(triethylsilyloxy)-2-(prop-1-en-3-yl)cyclopent-3-ene;

[(1S,2R,3'RS)-3-(3'-t-butyldimethylsilyloxyoct-1'-yl)-1-(triethylsilyloxy)-2-(prop-1-en-3-yl)cyclopent-3-ene;

[(1S,2R,3'S)-3-(3'-t-butyldimethylsilyloxy-4'-methylnon-1'-yl)-1-(triethylsilyloxy)-2-(prop-1-en-3-yl)cyclopent-3-ene;

[(1S,2R,3'RS)-3-(3'-t-butyldimethylsilyloxy-4'-methylnon-1'-yl)-1-(triethylsilyloxy)-2-(prop-1-en-3-yl)cyclopent-3-ene;

[(1S,2R,3'S)-3-(3'-t-butyldimethylsilyloxy-4'-phenylbut-1'-yl)-1-(triethylsilyloxy)-2-(prop-1-en-3-yl)cyclopent-3-ene;

[(1S,2R,3'RS)-3-(3'-t-butyldimethylsilyloxy-4'-phenylbut-1'-yl)-1-(triethylsilyloxy)-2-(prop-1-en-3-yl)cyclopent-3-ene;

[(1S,2R,3'S)-3-(3'-t-butyldimethylsilyloxy-4'-cyclopentylprop-1'-yl)-1-(triethylsilyloxy)-2-(prop-1-en-3-yl)cyclo-pent-3-ene;

[(1S,2R,3'RS)-3-(3'-t-butyldimethylsilyloxy-4'-cyclopentylprop-1'-yl)-1-(triethylsilyloxy)-2-(prop-1-en-3-yl)cyclo-pent-3-ene;

[(1S,2R,3'S)-3-(3'-t-butyldimethylsilyloxy-4'-methyl-4'-phenoxybut-1'-yl)-1-(triethylsilyloxy)-2-(prop-1-en-3-yl)cyclopent-3-ene;

[(1S,2R,3'RS)-3-(3'-t-butyldimethylsilyloxy-4'-methyl-4'-phenoxybut-1'-yl)-1-(triethylsilyloxy)-2-(prop-1-en-3-yl)cyclopent-3-ene;

[(1S,2R,3'S)-3-(3'-t-butyldimethylsilyloxy-4'-methyloct-1'-yl)-1-(triethylsilyloxy)-2-(prop-1-en-3-yl)cyclopent-3-ene;

[(1S,2R,3'RS)-3-(3'-t-butyldimethylsilyloxy-4'-methyloct-1'-yl)-1-(triethylsilyloxy)-2-(prop-1-en-3-yl)cyclopent-3-ene;

[(1S,2R,3'S)-3-(3'-t-butyldimethylsilyloxy-3'-methyl-3'-cyclohexylprop-1'-yl)-1-(triethylsilyloxy)-2-(prop-1-en-3-yl)cyclopent-3-ene;

[(1S,2R,3'RS)-3-(3'-t-butyldimethylsilyloxy-3'-methyl-3'-cyclohexylprop-1'-yl)-1-(triethylsilyloxy)-2-(prop-1-en-3-yl)cyclopent-3-ene;

[(1S,2R,3'S)-3-(3'-t-butyldimethylsilyloxy-3'-methyloct-1'-yl)-1-(triethylsilyloxy)-2-(prop-1-en-3-yl)cyclopent-3-ene;

[(1S,2R,3'RS)-3-(3'-t-butyldimethylsilyloxy-3'-methyloct-1'-yl)-1-(triethylsilyloxy)-2-(prop-1-en-3-yl)cyclopent-3-ene.

[(±)-3-(3'-t-butyldimethylsilyloxy-4'-phenoxybut-1'-yl)-1-(triethylsilyloxy)-2-(prop-1-en-3-yl)cyclopent-3-ene;

[(1S,2R,3RS)-3-(3'-t-butyldimethylsilyloxy-4'-phenoxybut-1'-yl)-1-(triethylsilyloxy)-2-methyl-2-(prop-1-en-3-yl)cyclopent-3-ene;

[(±)-3-(3'-t-butyldimethylsilyloxy-3'-cyclohexylprop-1'-yl)-1-(triethylsilyloxy)-2-(prop-1-en-3-yl)cyclopent-3-ene;

[(±)-3-(3'-t-butyldimethylsilyloxyoct-1'-yl)-1-(triethylsilyloxy)-2-(prop-1-en-3-yl)cyclopent-3-ene;

[(±)-3-(3'-t-butyldimethylsilyloxy-4'-phenylbut-1'-yl)-1-(triethylsilyloxy)-2-(prop-1-en-3-yl)cyclopent-3-ene;

[(±)-3-(3'-t-butyldimethylsilyloxy-4'-methylnon-1'-yl)-1-(triethylsilyloxy)-2-(prop-1-en-3-yl)cyclopent-3-ene;

[(±)-3-(3'-t-butyldimethylsilyloxydodec-1'-yl)-1-(triethylsilyloxy)-2-(prop-1-en-3-yl)cyclopent-3-ene;

[(±)-3-(3'-t-butyldimethylsilyloxy-8',8',8'-trifluorooct-1'-yl)-1-(triethylsilyloxy)-2-(prop-1-en-3-yl)cyclopent-3-ene;

[(±)-3-(3'-t-butyldimethylsilyloxy-3'-cyclopentylprop-1'-yl)-1-(triethylsilyloxy)-2-(prop-1-en-3-yl)cyclopent-3-ene;

[(±)-3-(3'-t-butyldimethylsilyloxy-4'-methyl-4'-phenoxybut-1'-yl)-1-(triethylsilyloxy)-2-(prop-1-en-3-yl)cyclopent-3-ene;

[(±)-3-(3'-t-butyldimethylsilyloxy-4'-methyl-4'-oct-1'-yl)-1-(triethylsilyloxy)-2-(prop-1-en-3-yl)cyclopent-3-ene;

[(1S,2R,3'RS)-3-(3'-t-butyldimethylsilyloxy-3'-cyclohexylprop-1'-yl)-1-(triethylsilyloxy)-2-methyl-2-(prop-1-en-3-yl)cyclopent-3-ene;

[(1S,2R,3'RS)-3-(3'-t-butyldimethylsilyloxyoct-1'-yl)-1-(triethylsilyloxy)-2-methyl-2-(prop-1-en-3-yl)cyclopent-3-ene;

[(±)-3-(3'-t-butyldimethylsilyloxy-3'-methyl-3'-cyclohexylprop-1'-yl)-1-(triethylsilyloxy)-2-(prop-1-en-3-yl)cyclopent-3-ene;

[(±)-3-(3'-t-butyldimethylsilyloxy-3'-methyloct-1'-yl)-1-(triethylsilyloxy)-2-(prop-1-en-3-yl)cyclopent-3-ene; and

[(1S,2R,3'RS)-3-(3'-t-butyldimethylsilyloxy-4'-phenoxybut-1'-yl)-1-(triethylsilyloxy)-2-n-butyl-2-(prop-1-en-3-yl)cyclopent-3-ene.

PREPARATION 21

Preparation of (1S,2R,3'S)-3-[3'-(t-butyldimethylsilyloxy)-4'-phenoxybut-1'-yl]-1-(triethylsilyloxy)-2-(1-hydroxyprop-3-yl)cyclopent-3-ene and Related Compounds of Formula (23)

A. A solution of 9-borabicyclo[3.3.1]nonane, 0.5M in tetrahydrofuran (4.48 ml, 2.24 mmol), was added to a solution of (1S,2R,3'S)-3-[3'-(t-butyldimethylsilyloxy)-4'-phenoxybut-1'-yl]-1-(triethylsilyloxy)-2-(prop-1-en-3-yl)cyclopent-3-ene, the compound of formula (22) (578 mg, 1.12 mmol), in 5 ml of tetrahydrofuran. After 40 minutes a solution of 3M sodium hydroxide (3 ml) was added, followed by 30% hydrogen peroxide (3 ml), (keeping the temperature lower than 30° C.), and the mixture was stirred for 10 more minutes. It was then diluted with ether (10 ml), the phases were separated and the aqueous phase was extracted with ether (3×5 ml). The combined organic extracts were dried (anhydrous magnesium sulfate), evaporated and the residue was purified by column chromatography (silica gel, hexane/ethyl acetate, 90/10) giving 534 mg of (1S,2R,3'S)-3-[3'-(t-butyldimethylsilyloxy)-4'-phenoxybut-1'-yl]-1-(triethylsilyloxy)-2-(1-hydroxyprop-3-yl)cyclopent-3-ene, the compound of formula (23).

B. Similarly, following the procedure of A above and replacing (1S,2R,3'S)-3-[3'-(t-butyldimethylsilyloxy)-4'-phenoxybut-1'-yl]-1-(triethylsilyloxy)-2-(prop-1-en-3-yl)cyclopent-3-ene with the appropriate compound of formula (22), the following compounds of formula (23) are prepared:

[(1S,2R,3'R)-3-(3'-t-butyldimethylsilyloxy-4'-phenoxybut-1'-yl)-1-(triethylsilyloxy)-2-(1-hydroxyprop-3-yl)cyclopent-3-ene;

[(1S,2R,3'RS)-3-(3'-t-butyldimethylsilyloxy-4'-phenoxybut-1'-yl)-1-(triethylsilyloxy)-2-(1-hydroxyprop-3-yl)cyclopent-3-ene;

[(1S,2R,3'S)-3-(3'-t-butyldimethylsilyloxy-3'-cyclohexylprop-1'-yl)-1-(triethylsilyloxy)-2-(1-hydroxyprop-3-yl)cyclopent-3-ene;

[(1S,2R,3'R)-3-(3'-t-butyldimethylsilyloxy-3'-cyclohexylprop-1'-yl)-1-(triethylsilyloxy)-2-(1-hydroxyprop-3-yl)cyclopent-3-ene;

[(1S,2R,3'RS)-3-(3'-t-butyldimethylsilyloxy-3'-cyclohexylprop-1'-yl)-1-(triethylsilyloxy)-2-(1-hydroxyprop-3-yl)cyclopent-3-ene;

[(1S,2R,3'S)-3-(3'-t-butyldimethylsilyloxyoct-1'-yl)-1-(triethylsilyloxy)-2-(1-hydroxyprop-3-yl)cyclopent-3-ene;

[(1S,2R,3'R)-3-(3'-t-butyldimethylsilyloxyoct-1'-yl)-1-(triethylsilyloxy)-2-(1-hydroxyprop-3-yl)cyclopent-3-ene;

[(1S,2R,3'RS)-3-(3'-t-butyldimethylsilyloxyoct-1'-yl)-1-(triethylsilyloxy)-2-(1-hydroxyprop-3-yl)cyclopent-3-ene;

[(1S,2R,3'S)-3-(3'-t-butyldimethylsilyloxy-4'-methylnon-1'-yl)-1-(triethylsilyloxy)-2-(1-hydroxyprop-3-yl)cyclopent-3-ene;

[(1S,2R,3'RS)-3-(3'-t-butyldimethylsilyloxy-4'-methylnon-1'-yl)-1-(triethylsilyloxy)-2-(1-hydroxyprop-3-yl)cyclopent-3ene;

[(1S,2R,3'S)-3-(3'-t-butyldimethylsilyloxy-4'-phenylbut-1'-yl)-1-(triethylsilyloxy)-2-(1-hydroxyprop-3-yl)cyclopent-3-ene;

[(1S,2R,3'RS)-3-(3'-t-butyldimethylsilyloxy-4'-phenylbut-1'-yl)-1-(triethylsilyloxy)-2-(1-hydroxyprop-3-yl)cyclopent-3-ene;

[(1S,2R,3'S)-3-(3'-t-butyldimethylsilyloxy-4'-cyclopentylprop-1'-yl)-1-(triethylsilyloxy)-2-(1-hydroxyprop-3-yl)cyclopent-3ene;

[(1S,2R,3'RS)-3-(3'-t-butyldimethylsilyloxy-4'-cyclopentylprop-1'-yl)-1-(triethylsilyloxy)-2-(1-hydroxyprop-3-yl)cyclopent-3-ene;

[(1S,2R,3'S)-3-(3'-t-butyldimethylsilyloxy-4'-methyl-4'-phenoxybut-1'-yl)-1-(triethylsilyloxy)-2-(1-hydroxyprop-3-yl)cyclopent-3-ene;

[(1S,2R,3'RS)-3-(3'-t-butyldimethylsilyloxy-4'-methyl-4'-phenoxybut-1'-yl)-1-(triethylsilyloxy)-2-(1-hydroxyprop-3-yl)cyclopent-3-ene;

[(1S,2R,3'S)-3-(3'-t-butyldimethylsilyloxy-4'-methyloct-1'-yl)-1-(triethylsilyloxy)-2-(1-hydroxyprop-3-yl)cyclopent-3-ene;

[(1S,2R,3'RS)-3-(3'-t-butyldimethylsilyloxy-4'-methyloct-1'-yl)-1-(triethylsilyloxy)-2-(1-hydroxyprop-3-yl)cyclopent-3-ene;

[(1S,2R,3'S)-3-(3'-t-butyldimethylsilyloxy-3'-methyl-3'-cyclohexylprop-1'-yl)-1-(triethylsilyloxy)-2-(1-hydroxyprop-3-yl)cyclopent-3-ene;

[(1S,2R,3'RS)-3-(3'-t-butyldimethylsilyloxy-3'-methyl-3'-cyclohexylprop-1'-yl)-1-(triethylsilyloxy)-2-(1-hydroxyprop-3-yl)cyclopent-3-ene;

[(1S,2R,3'S)-3-(3'-t-butyldimethylsilyloxy-3'-methyloct-1'-yl)-1-(triethylsilyloxy)-2-(1-hydroxyprop-3-yl)cyclopent-3-ene;

[(1S,2R,3'RS)-3-(3'-t-butyldimethylsilyloxy-3'-methyloct-1'-yl)-1-(triethylsilyloxy)-2-(1-hydroxyprop-3-yl)cyclopent-3-ene.

[(±)-3-(3'-t-butyldimethylsilyloxy-4'-phenoxybut-1'-yl)-1-(triethylsilyloxy)-2-(1-hydroxyprop-3-yl)cyclopent-3-ene;

[(1S,2R,3RS)-3-(3'-t-butyldimethylsilyloxy-4'-phenoxybut-1'-yl)-1-(triethylsilyloxy)-2-methyl-2-(1-hydroxyprop-3-yl)cyclopent-3-ene;

[(±)-3-(3'-t-butyldimethylsilyloxy-3'-cyclohexylprop-1'-yl)-1-(triethylsilyloxy)-2-(1-hydroxyprop-3-yl)cyclopent-3-ene;

[(±)-3-(3'-t-butyldimethylsilyloxyoct-1'-yl)-1-(triethylsilyloxy)-2-(1-hydroxyprop-3-yl)cyclopent-3-ene;

[(±)-3-(3'-t-butyldimethylsilyloxy-4'-phenylbut-1'-yl)-1-(triethylsilyloxy)-2-(1-hydroxyprop-3-yl)cyclopent-3-ene;

[(±)-3-(3'-t-butyldimethylsilyloxy-4'-methylnon-1'-yl)-1-(triethylsilyloxy)-2-(1-hydroxyprop-3-yl)cyclopent-3-ene;

[(±)-3-(3'-t-butyldimethylsilyloxydodec-1'-yl)-1-(triethylsilyloxy)-2-(1-hydroxyprop-3-yl)cyclopent-3-ene;

[(±)-3-(3'-t-butyldimethylsilyloxy-8',8',8'-trifluorooct-1'-yl)-1-(triethylsilyloxy)-2-(1-hydroxyprop-3-yl)cyclopent-3-ene;

[(±)-3-(3'-t-butyldimethylsilyloxy-3'-cyclopentylprop-1'-yl)-1-(triethylsilyloxy)-2-(1-hydroxyprop-3-yl)cyclopent-3-ene;

[(±)-3-(3'-t-butyldimethylsilyloxy-4'-methyl-4'-phenoxybut-1'-yl)-1-(triethylsilyloxy)-2-(1-hydroxyprop-3-yl)cyclopent-3-ene;

[(±)-3-(3'-t-butyldimethylsilyloxy-4'-methyl-4'-oct-1'-yl)-1-(triethylsilyloxy)-2-(1-hydroxyprop-3-yl)cyclopent-3-ene;

[(1S,2R,3'RS)-3-(3'-t-butyldimethylsilyloxy-3'-cyclohexylprop-1'-yl)-1-(triethylsilyloxy)-2-methyl-2-(1-hydroxyprop-3-yl)cyclopent-3-ene;

[(1S,2R,3'RS)-3-(3'-t-butyldimethylsilyloxyoct-1'-yl)-1-(triethylsilyloxy)-2-methyl-2-(1-hydroxyprop-3-yl)cyclopent-3-ene;

[(±)-3-(3'-t-butyldimethylsilyloxy-3'-methyl-3'-cyclohexylprop-1'-yl)-1-(triethylsilyloxy)-2-(1-hydroxyprop-3-yl)cyclopent-3-ene;

[(±)-3-(3'-t-butyldimethylsilyloxy-3'-methyloct-1'-yl)-1-(triethylsilyloxy)-2-(1-hydroxyprop-3-yl)cyclopent-3ene; and

[(1S,2R,3'RS)-3-(3'-t-butyldimethylsilyloxy-4'-phenoxybut-1'-yl)-1-(triethylsilyloxy)-2-n-butyl-2-(1-hydroxyprop-3-yl)cyclopent-3-ene.

PREPARATION 22

Preparation of (8S,9R,15S)-9-(triethylsilyloxy)-15-(t-butyldimethylsilyloxy)-16-phenoxy-17,18,19,20-tetranorprosta-3,4,11-trienoic acid, methyl ester and Related Compounds of Formula (25)

A. Dimethylsulfoxide (0.318 ml, 4.48 mmol) was added slowly to a solution of oxalyl chloride (0.286 ml, 3.36 mmol) in 5 ml of methylene chloride cooled to −75° C. After 10 minutes, a solution of (1S,2R,3'S)-3-[3'-(t-butyldimethylsilyloxy)-4'-phenoxybut-1'-yl]-1-(triethylsilyloxy)-2-(1-hydroxyprop-3-yl)cyclopent-3-ene (564 mg, 1.0 mmol), the compound of formula (23), in 3 ml of methylene chloride was added dropwise, the mixture was stirred for 25 minutes and then triethylamine (0.936 ml, 6.72 mmol) was added dropwise and stirred at −75° C. for 1 hour. The reaction mixture was then poured into saturated ammonium chloride (5 ml), the phases were separated and the aqueous phase was extracted with methylene chloride (3×5 ml). The combined organic extracts were dried (anhydrous magnesium sulfate) and evaporated. The residue was dissolved in 3 ml of tetrahydrofuran, cooled to 5° C. and treated with 2 ml of a 1.5 M solution of ethynylmagnesium chloride in tetrahydrofuran. After 10 minutes, the reaction mixture was poured into saturated ammonium chloride and extracted with ether (5×5 ml). The combined organic extracts were dried (anhydrous magnesium sulfate) and evaporated to yield the crude alkynols of formula (24) as an epimeric mixture. This mixture was dissolved in 10 ml of xylene and 1.70 ml (13.5 mmol) of trimethylorthoacetate containing 0.1 ml of propionic acid and the mixture was heated to 110° C. for 5 hours. The volatiles were then evaporated and the residue was purified by column chromatography (silica gel, hexane/ethyl acetate, 80/20) giving 332 mg of (1S,2R,3'S)-9-(triethylsilyloxy)-15-(t-butyldimethylsilyloxy)-16-phenoxy-17,18,19,20-tetranorprosta-3,4,11-trienoic acid, methyl ester, the compound of formula (25).

B. Similarly, following the procedure of A above and replacing (1S,2R,3'S)-3-[3'-(t-butyldimethylsilyloxy)-4'-phenoxybut-1'-yl]-1-(triethylsilyloxy)-2-(1-hydroxyprop-3-yl)cyclopent-3-ene with the appropriate compound of formula (23), the following compounds of formula (24) are prepared:

(8R,9S,15R)-9-(triethylsilyloxy)-15-(t-butyldimethylsilyloxy)-16-phenoxy-17,18,19,20-tetranorprosta-3,4,11-trienoic acid, methyl ester;

(8R,9S,15RS)-9-(triethylsilyloxy)-15-(t-butyldimethylsilyloxy)-16-phenoxy-17,18,19,20-tetranorprosta-3,4,11-trienoic acid, methyl ester;

(8R,9S,15S)-8-methyl-9-(triethylsilyloxy)-15-(t-butyldimethylsilyloxy)-16-phenoxy-17,18,19,20-tetranorprosta-3,4,11-trienoic acid, methyl ester;

(8R,9S,15S)-9-(triethylsilyloxy)-15-(t-butyldimethylsilyloxy)-15-cyclohexyl-16,17,18,19,20-pentanorprosta-3,4,11-trienoic acid, methyl ester;

(8R,9S,15R)-9-(triethylsilyloxy)-15-(t-butyldimethylsilyloxy)-15-cyclohexyl-16,17,18,19,20-pentanorprosta-3,4,11-trienoic acid, methyl ester;

(8R,9S,15RS)-9-(triethylsilyloxy)-15-(t-butyldimethylsilyloxy)-15-cyclohexyl-16,17,18,19,20-pentanorprosta-3,4,11-trienoic acid, methyl ester;

(8R,9S,15S)-9-(triethylsilyloxy)-15-(t-butyldimethylsilyloxy)prosta-3,4,11-trienoic acid, methyl ester;

(8R,9S,15R)-9-(triethylsilyloxy)-15-(t-butyldimethylsilyloxy)prosta-3,4,11-trienoic acid, methyl ester;

(8R,9S,15RS)-9-(triethylsilyloxy)-15-(t-butyldimethylsilyloxy)prosta-3,4,11-trienoic acid, methyl ester;

(8R,9S,15S)-9-(triethylsilyloxy)-15-(t-butyldimethylsilyloxy)-16,20-dimethylprosta-3,4,11-trienoic acid, methyl ester;

(8R,9S,15RS)-9-(triethylsilyloxy)-15-(t-butyldimethylsilyloxy)-16,20-dimethylprosta-3,4,11-trienoic acid, methyl ester;

(8R,9S,15S)-9-(triethylsilyloxy)-15-(t-butyldimethylsilyloxy)-16-phenyl-17,18,19,20-tetranorprosta-3,4,11-trienoic acid, methyl ester;

(8R,9S,15RS)-9-(triethylsilyloxy)-15-(t-butyldimethylsilyloxy)-16-phenyl-17,18,19,20-tetranorprosta-3,4,11-trienoic acid, methyl ester;

(8R,9S,15S)-9-(triethylsilyloxy)-15-(t-butyldimethylsilyloxy)-15-cyclopentyl-16,17,18,19,20-pentanorprosta-3,4,11-trienoic acid, methyl ester;

(8R,9S,15RS)-9-(triethylsilyloxy)-15-(t-butyldimethylsilyloxy)-15-cyclopentyl-16,17,18,19,20-pentanorprosta-3,4,11-trienoic acid, methyl ester;

(8R,9S,15S)-9-(triethylsilyloxy)-15-(t-butyldimethylsilyloxy)-16-methyl-16-phenoxy-17,18,19,20-tetranorprosta-3,4,11-trienoic acid, methyl ester;

(8R,9S,15RS)-9-(triethylsilyloxy)-15-(t-butyldimethylsilyloxy)-16-methyl-16-phenoxy-17,18,19,20-tetranorprosta-3,4,11-trienoic acid, methyl ester;

(8R,9S,15S)-9-(triethylsilyloxy)-15-(t-butyldimethylsilyloxy)-16-methylprosta-3,4,11-trienoic acid, methyl ester;

(8R,9S,15RS)-9-(triethylsilyloxy)-15-(t-butyldimethylsilyloxy)-16-methylprosta-3,4,11-trienoic acid, methyl ester;

(8R,9S,15S)-9-(triethylsilyloxy)-15-(t-butyldimethylsilyloxy)-15-methyl-15-cyclohexyl-16,17,18,19,20-pentanorprosta-3,4,11-trienoic acid, methyl ester;

(8R,9S,15RS)-9-(triethylsilyloxy)-15-(t-butyldimethylsilyloxy)-15-methyl-15-cyclohexyl-16,17,18,19,20-pentanorprosta-3,4,11-trienoic acid, methyl ester;

(8R,9S,15S)-9-(triethylsilyloxy)-15-methyl-15-(t-butyldimethylsilyloxy)prosta-3,4,11-trienoic acid, methyl ester;

(8R,9S,15RS)-9-(triethylsilyloxy)-15-methyl-15-(t-butyldimethylsilyloxy)prosta-3,4,11-trienoic acid, methyl ester;

(±)-9-(triethylsilyloxy)-15-(t-butyldimethylsilyloxy)-16-phenoxy-17,18,19,20-tetranorprosta-3,4,11-trienoic acid, methyl ester;

(±)-9-(triethylsilyloxy)-15-(t-butyldimethylsilyloxy)-15-cyclohexyl-16,17,18,19,20-pentanorprosta-3,4,11-trienoic acid, methyl ester;
(±)-9-(triethylsilyloxy)-15-(t-butyldimethylsilyloxy)-prosta-3,4,11-trienoic acid, methyl ester;
(±)-9-(triethylsilyloxy)-15-(t-butyldimethylsilyloxy)-16,20-dimethylprosta-3,4,11-trienoic acid, methyl ester;
(±)-9-(triethylsilyloxy)-15-(t-butyldimethylsilyloxy)-16-phenyl-17,18,19,20-tetranorprosta-3,4,11-trienoic acid, methyl ester;
(±)-9-(triethylsilyloxy)-15-(t-butyldimethylsilyloxy)-20-butylprosta-3,4,11-trienoic acid, methyl ester;
(±)-9-(triethylsilyloxy)-15-(t-butyldimethylsilyloxy)-20,20,20-trifluoroprosta-3,4,11-trienoic acid, methyl ester;
(±)-9-(triethylsilyloxy)-15-(t-butyldimethylsilyloxy)-15-cyclopentyl-16,17,18,19,20-pentanorprosta-3,4,11-trienoic acid, methyl ester;
(±)-9-(triethylsilyloxy)-15-(t-butyldimethylsilyloxy)-16-methyl-16-phenoxy-17,18,19,20-tetranorprosta-3,4,11-trienoic acid, methyl ester;
(±)-9-(triethylsilyloxy)-15-(t-butyldimethylsilyloxy)-16-methylprosta-3,4,11-trienoic acid, methyl ester;
(±)-9-(triethylsilyloxy)-15-(t-butyldimethylsilyloxy)-15-methyl-15-cyclohexyl-16,17,18,19,20-pentanorprosta-3,4,11-trienoic acid, methyl ester;
(±)-9-(triethylsilyloxy)-15-methyl-15-(t-butyldimethylsilyloxy)prosta-3,4,11-trienoic acid, methyl ester;
(±)-8-n-butyl-9-(triethylsilyloxy)-15-(t-butyldimethylsilyloxy)-16-phenoxy-17,18,19,20-tetranorprosta-3,4,11-trienoic acid, methyl ester.

PREPARATION 23

Preparation of (8S,9R,15S)-9-hydroxy-15-(t-butyldimethylsilyloxy)-16-phenoxy-17,18,19,20-tetranorprosta-3,4,11-trienoic acid, methyl ester and Related Compounds of Formula (7) where X is —CH$_2$CH=C=CH— and m is 1

A. A solution of (8S,9R,15S)-9-(triethylsilyloxy)-15-(t-butyldimethylsilyloxy)-16-phenoxy-17,18,19,20-tetranorprosta-3,4,11-trienoic acid, methyl ester, the compound of formula (25) (77 mg, 0.125 mmol), was dissolved in 2 ml of tetrahydrofuran/acetic acid/water (8:8:1) and after 18 hours at room temperature, the solvents were removed by azeotroping with toluene (2×20 ml). The residue was purified by column chromatography (silica gel, hexane/ethyl acetate, 80/20) giving 29 mg of (8S,9R,15S)-9-hydroxy-15-(t-butyldimethylsilyloxy)-16-phenoxy-17,18,19,20-tetranorprosta-3,4,11-trienoic acid, methyl ester, the compound of formula (7) where X is —CH$_2$CH=C=CH— and m is 1.

B. Similarly, following the procedure of A above and replacing (8S,9R,15S)-9-(triethylsilyloxy)-15-(t-butyldimethylsilyloxy)-16-phenoxy-17,18,19,20-tetranorprosta-3,4,11-trienoic acid, methyl ester with the appropriate compound of formula (25), the following compounds of formula (7) where X is —CH$_2$CH=C=CH— and m is 1 are prepared:

(8R,9S,15R)-9-hydroxy-15-(t-butyldimethylsilyloxy)-16-phenoxy-17,18,19,20-tetranorprosta-3,4,11-trienoic acid, methyl ester;
(8R,9S,15RS)-9-hydroxy-15-(t-butyldimethylsilyloxy)-16-phenoxy-17,18,19,20-tetranorprosta-3,4,11-trienoic acid, methyl ester;
(8R,9S,15S)-8-methyl-9-hydroxy-15-(t-butyldimethylsilyloxy)-16-phenoxy-17,18,19,20-tetranorprosta-3,4,11-trienoic acid, methyl ester;
(8R,9S,15S)-9-hydroxy-15-(t-butyldimethylsilyloxy)-15-cyclohexyl-16,17,18,19,20-pentanorprosta-3,4,11-trienoic acid, methyl ester;
(8R,9S,15R)-9-hydroxy-15-(t-butyldimethylsilyloxy)-15-cyclohexyl-16,17,18,19,20-pentanorprosta-3,4,11-trienoic acid, methyl ester;
(8R,9S,15RS)-9-hydroxy-15-(t-butyldimethylsilyloxy)-15-cyclohexyl-16,17,18,19,20-pentanorprosta-3,4,11-trienoic acid, methyl ester;
(8R,9S,15S)-9-hydroxy-15-(t-butyldimethylsilyloxy)-prosta-3,4,11-trienoic acid, methyl ester;
(8R,9S,15R)-9-hydroxy-15-(t-butyldimethylsilyloxy)-prosta-3,4,11-trienoic acid, methyl ester;
(8R,9S,15RS)-9-hydroxy-15-(t-butyldimethylsilyloxy)-prosta-3,4,11-trienoic acid, methyl ester;
(8R,9S,15S)-9-hydroxy-15-(t-butyldimethylsilyloxy)-16,20-dimethylprosta-3,4,11-trienoic acid, methyl ester;
(8R,9S,15RS)-9-hydroxy-15-(t-butyldimethylsilyloxy)-16,20-dimethylprosta-3,4,11-trienoic acid, methyl ester;
(8R,9S,15S)-9-hydroxy-15-(t-butyldimethylsilyloxy)-16-phenyl-17,18,19,20-tetranorprosta-3,4,11-trienoic acid, methyl ester;
(8R,9S,15RS)-9-hydroxy-15-(t-butyldimethylsilyloxy)-16-phenyl-17,18,19,20-tetranorprosta-3,4,11-trienoic acid, methyl ester;
(8R,9S,15S)-9-hydroxy-15-(t-butyldimethylsilyloxy)-15-cyclopentyl-16,17,18,19,20-pentanorprosta-3,4,11-trienoic acid, methyl ester;
(8R,9S,15RS)-9-hydroxy-15-(t-butyldimethylsilyloxy)-15-cyclopentyl-16,17,18,19,20-pentanorprosta-3,4,11-trienoic acid, methyl ester;
(8R,9S,15S)-9-hydroxy-15-(t-butyldimethylsilyloxy)-16-methyl-16-phenoxy-17,18,19,20-tetranorprosta-3,4,11-trienoic acid, methyl ester;
(8R,9S,15RS)-9-hydroxy-15-(t-butyldimethylsilyloxy)-16-methyl-16-phenoxy-17,18,19,20-tetranorprosta-3,4,11-trienoic acid, methyl ester;
(8R,9S,15S)-9-hydroxy-15-(t-butyldimethylsilyloxy)-16-methylprosta-3,4,11-trienoic acid, methyl ester;
(8R,9S,15RS)-9-hydroxy-15-(t-butyldimethylsilyloxy)-16-methylprosta-3,4,11-trienoic acid, methyl ester;
(8R,9S,15S)-9-hydroxy-15-(t-butyldimethylsilyloxy)-15-methyl-15-cyclohexyl-16,17,18,19,20-pentanorprosta-3,4,11-trienoic acid, methyl ester;
(8R,9S,15RS)-9-hydroxy-15-(t-butyldimethylsilyloxy)-15-methyl-15-cyclohexyl-16,17,18,19,20-pentanorprosta-3,4,11-trienoic acid, methyl ester;
(8R,9S,15S)-9-hydroxy-15-methyl-15-(t-butyldimethylsilyloxy)prosta-3,4,11-trienoic acid, methyl ester;
(8R,9S,15RS)-9-hydroxy-15-methyl-15-(t-butyldimethylsilyloxy)prosta-3,4,11-trienoic acid, methyl ester;
(±)-9-hydroxy-15-(t-butyldimethylsilyloxy)-16-phenoxy-17,18,19,20-tetranorprosta-3,4,11-trienoic acid, methyl ester;
(±)-9-hydroxy-15-(t-butyldimethylsilyloxy)-15-cyclohexyl-16,17,18,19,20-pentanorprosta-3,4,11-trienoic acid, methyl ester;
(±) -9-hydroxy-15-(t-butyldimethylsilyloxy)prosta-3,4,11-trienoic acid, methyl ester;
(±)-9-hydroxy-15-(t-butyldimethylsilyloxy)-16,20-dimethylprosta-3,4,11-trienoic acid, methyl ester;

(±)-9-hydroxy-15-(t-butyldimethylsilyloxy)-16-phenyl-17,18,19,20-tetranorprosta-3,4,11-trienoic acid, methyl ester;

(±)-9-hydroxy-15-(t-butyldimethylsilyloxy)-20-butyl-prosta-3,4,11-trienoic acid, methyl ester;

(±)-9-hydroxy-15-(t-butyldimethylsilyloxy)-20,20,20-trifluoroprosta-3,4,11-trienoic acid, methyl ester;

(±)-9-hydroxy-15-(t-butyldimethylsilyloxy)-15-cyclopentyl-16,17,18,19,20-pentanorprosta-3,4,11-trienoic acid, methyl ester;

(±)-9-hydroxy-15-(t-butyldimethylsilyloxy)-16-methyl-16-phenoxy-17,18,19,20-tetranorprosta-3,4,11-trienoic acid, methyl ester;

(±)-9-hydroxy-15-(t-butyldimethylsilyloxy)-16-methyl-prosta-3,4,11-trienoic acid, methyl ester;

(±)-9-hydroxy-15-(t-butyldimethylsilyloxy)-15-methyl-15-cyclohexyl-16,17,18,19,20-pentanorprosta-3,4,11-trienoic acid, methyl ester;

(±)-9-hydroxy-15-methyl-15-(t-butyldimethylsilyloxy)-prosta-3,4,11-trienoic acid, methyl ester;

(±)-8-n-butyl-9-hydroxy-15-(t-butyldimethylsilyloxy)-16-phenoxy-17,18,19,20-tetranorprosta-3,4,11-trienoic acid, methyl ester.

PREPARATION 24

Preparation of (8R,15S)-9-oxo-15-(t-butyldimethylsilyloxy)-16-phenoxy-17,18,19,20-tetranorprosta-5(Z),11-dienoic acid, methyl ester and Related Compounds of Formula (8)

A. A solution of (8R,9S,15S)-9-hydroxy-15-(t-butyldimethylsilyloxy)-16-phenoxy-17,18,19,20-tetranorprosta-5(Z),11-dienoic acid, methyl ester, the compound of formula (7), (240 mg, 0.477 mmol) in 3 ml of N,N-dimethylformamide was cooled to 0° C. and treated with pyridinium dichromate (898 mg, 2.39 mmol). After 6 hrs the mixture was poured into 50 ml of water and extracted with benzene (3×10 ml). The combined organic extracts were washed with brine, dried over anhydrous magnesium sulfate and the solvent removed under reduced pressure. The residue was purified by column chromatography (silica gel, hexane/ethyl acetate 90/10) giving (8R,15S)-9-oxo-15-(t-butyldimethylsilyloxy)-16-phenoxy-17,18,19,20-tetranorprosta-5(Z),11-dienoic acid, methyl ester, the compound of formula (8) where X is —CH=CH— and m is 3, 150 mg.

B. Similarly, following the procedure of A above and replacing (8R,9S,15S)-9-hydroxy-15-(t-butyldimethylsilyloxy)-16-phenoxy-17,18,19,20-tetranorprosta-5(Z),11-dienoic acid, methyl ester with the appropriate compound of formula (7) where X is —CH=CH— and m is 3, the following compounds of formula (8) were prepared:

(8R,15R)-9-oxo-15-(t-butyldimethylsilyloxy)-16-phenoxy-17,18,19,20-tetranorprosta-5(Z),11-dienoic acid, methyl ester;

(±)-9-oxo-15-(t-butyldimethylsilyloxy)-16-phenoxy-17,18,19,20-tetranorprosta-5(Z),11-dienoic acid, methyl ester;

(8R,15RS)-8-methyl-9-oxo-15-(t-butyldimethylsilyloxy)-16-phenoxy-17,18,19,20-tetranorprosta-5(Z),11-dienoic acid, methyl ester;

(±)-9-oxo-15-(t-butyldimethylsilyloxy)-15-cyclohexyl-16,17,18,19,20-pentanorprosta-5(Z),11-dienoic acid, methyl ester; and (±)-9-oxo-15-(t-butyldimethylsilyloxy)-prosta-5(Z),11-dienoic acid, methyl ester.

C. Similarly, following the procedure of A above and replacing (8R,9S,15S)-9-hydroxy-15-(t-butyldimethylsilyloxy)-16-phenoxy-17,18,19,20-tetranorprosta-5(Z),11-dienoic acid, methyl ester with the appropriate compound of formula (7) where X is —CH$_2$CH$_2$— and m is 3, prepared as shown in Preparation 18A, the following compound of formula (8) was prepared:

(8R,15S)-9-oxo-15-(t-butyldimethylsilyloxy)-16-phenoxy-17,18,19,20-tetranorprosta-11-enoic acid, methyl ester.

D. Similarly, following the procedure of A above and replacing (8R,9S,15S)-9-hydroxy-15-(t-butyldimethylsilyloxy)-16-phenoxy-17,18,19,20-tetranorprosta-5(Z),11-dienoic acid, methyl ester with the appropriate compound of formula (7) where X is —CH$_2$CH=C=CH— and m is 1, prepared as shown in Preparation 23, the following compound of formula (8) was prepared:

(8R,15S)-9-oxo-15-(t-butyldimethylsilyloxy)-16-phenoxy-17,18,19,20-tetranorprosta-3,4,11-trienoic acid, methyl ester.

E. Similarly, following the procedure of A above and replacing (8R,9S,15S)-9-hydroxy-15-(t-butyldimethylsilyloxy)-16-phenoxy-17,18,19,20-tetranorprosta-5(Z),11-dienoic acid, methyl ester with the appropriate compound of formula (7), the following compounds of formula (8) where X is —CH=CH— and m is 3, or where X is —CH$_2$CH$_2$— and m is 3, or where X is —CH$_2$CH=C=CH— and m is 1, are prepared:

[(±)-9-oxo-15-(t-butyldimethylsilyloxy)-16-phenyl-17,18,19,20-tetranorprosta-5(Z),11-dienoic acid, methyl ester;

[(±)-9-oxo-15-(t-butyldimethylsilyloxy)-16,20-dimethylprosta-5(Z),11-dienoic acid, methyl ester;

[(±)-9-oxo-15-(t-butyldimethylsilyloxy)-20-butylprosta-5(Z),11-dienoic acid, methyl ester;

[(±)-9-oxo-15-(t-butyldimethylsilyloxy)-20,20,20-trifluoroprosta-5(Z),11-dienoic acid, methyl ester;

(±)-9-oxo-15-(t-butyldimethylsilyloxy)-15-cyclopentyl-16,17,18,19,20-pentanorprosta-5(Z),11-dienoic acid, methyl ester;

[(±)-9-oxo-15-(t-butyldimethylsilyloxy)-16-methyl-16-phenoxy-17,18,19,20-tetranorprosta-5(Z),11-dienoic acid, methyl ester;

[(±)-9-oxo-15-(t-butyldimethylsilyloxy)-16-methyl-prosta-5(Z),11-dienoic acid, methyl ester;

[(8R,9S,15RS)-8-methyl-9-oxo-15-(t-butyldimethylsilyloxy)-15-cyclohexyl-16,17,18,19,20-pentanorprosta-5(Z),11-dienoic acid, methyl ester;

[(8R,9S,15RS)-8-methyl-9-oxo-15-(t-butyldimethylsilyloxy)-prosta-5(Z),11-dienoic acid, methyl ester;

[(±)-9-oxo-15-(t-butyldimethylsilyloxy)-15-methyl-15-cyclohexyl-16,17,18,19,20-pentanorprosta-5(Z),11-dienoic acid, methyl ester;

[(±)-9-oxo-15-(t-butyldimethylsilyloxy)-15-methyl-prosta-5(Z),11-dienoic acid, methyl ester;

[(8R,9S,15RS)-8-n-butyl-9-oxo-15-(t-butyldimethylsilyloxy)-16-phenoxy-17,18,19,20-tetranorprosta-5(Z),11-dienoic acid, methyl ester;

[(8R,9S,15RS)-9-oxo-15-(t-butyldimethylsilyloxy)-16-phenoxybut-1'-yl)-17,18,19,20-tetranorprosta-5(Z),11-dienoic acid, methyl ester;

[(8R,9S,15S)-9-oxo-15-(t-butyldimethylsilyloxy)-15-cyclohexyl-16,17,18,19,20-pentanorprosta-5(Z),11-dienoic acid, methyl ester;

[(8R,9S,15R)-9-oxo-15-(t-butyldimethylsilyloxy)-15-cyclohexyl-16,17,18,19,20-pentanorprosta-5(Z),11-dienoic acid, methyl ester;
[(8R,9S,15RS)-9-oxo-15-(t-butyldimethylsilyloxy)-15-cyclohexyl-16,17,18,19,20-pentanorprosta-5(Z),11-dienoic acid, methyl ester;
[(8R,9S,15S)-9-oxo-15-(t-butyldimethylsilyloxy)prosta-5(Z),11-dienoic acid, methyl ester;
[(8R,9S,15R)-9-oxo-15-(t-butyldimethylsilyloxy)prosta-5(Z),11-dienoic acid, methyl ester;
[(8R,9S,15RS)-9-oxo-15-(t-butyldimethylsilyloxy)prosta-5(Z),11-dienoic acid, methyl ester;
[(8R,9S,15S)-9-oxo-15-(t-butyldimethylsilyloxy)-16,20-dimethylprosta-5(Z),11-dienoic acid, methyl ester;
[(8R,9S,15RS)-9-oxo-15-(t-butyldimethylsilyloxy)-16,20-dimethylprosta-5(Z),11-dienoic acid, methyl ester;
[(8R,9S,15S)-9-oxo-15-(t-butyldimethylsilyloxy)-16-phenyl-17,18,19,20-tetranorprosta-5(Z),11-dienoic acid, methyl ester;
[(8R,9S,15RS)-9-oxo-15-(t-butyldimethylsilyloxy)-16-phenyl-17,18,19,20-tetranorprosta-5(Z),11-dienoic acid, methyl ester;
[(8R,9S,15S)-9-oxo-15-(t-butyldimethylsilyloxy)-15-cyclopentyl-16,17,18,19,20-pentanorprosta-5(Z),11-dienoic acid, methyl ester;
[(8R,9S,15RS)-9-oxo-15-(t-butyldimethylsilyloxy)-15-cyclopentyl-16,17,18,19,20-pentanorprosta-5(Z),11-dienoic acid, methyl ester;
[(8R,9S,15S)-9-oxo-15-(t-butyldimethylsilyloxy)-16-methyl-16-phenoxy-17,18,19,20-tetranorprosta-5(Z),11-dienoic acid, methyl ester;
[(8R,9S,15RS)-9-oxo-15-(t-butyldimethylsilyloxy)-16-methyl-16-phenoxy-17,18,19,20-tetranorprosta-5(Z),11-dienoic acid, methyl ester;
[(8R,9S,15R)-9-oxo-15-(t-butyldimethylsilyloxy)-16-methylprosta-5(Z),11-dienoic acid, methyl ester;
[(8R,9S,15RS)-9-oxo-15-(t-butyldimethylsilyloxy)-16-methylprosta-5(Z),11-dienoic acid, methyl ester;
[(8R,9S,15R)-9-oxo-15-(t-butyldimethylsilyloxy)-15-methyl-15-cyclohexyl-16,17,18,19,20-pentanorprosta-5(Z),11-dienoic acid, methyl ester;
[(8R,9S,15RS)-9-oxo-15-(t-butyldimethylsilyloxy)-15-methyl-15-cyclohexyl-16,17,18,19,20-pentanorprosta-5(Z),11-dienoic acid, methyl ester;
[(8R,9S,15S)-9-oxo-15-(t-butyldimethylsilyloxy)-15-methyl-16-methylprosta-5(Z),11-dienoic acid, methyl ester; and
[(8R,9S,15RS)-9-oxo-15-(t-butyldimethylsilyloxy)-15-methyl-16-methylprosta-5(Z),11-dienoic acid, methyl ester;
(8R,9S,15R)-9-oxo-15-(t-butyldimethylsilyloxy)-16-phenoxy-17,18,19,20-tetranorprosta-11-enoic acid, methyl ester;
(8R,9S,15RS)-9-oxo-15-(t-butyldimethylsilyloxy)-16-phenoxy-17,18,19,20-tetranorprosta-11-enoic acid, methyl ester;
(8R,9S,15S)-8-methyl-9-oxo)-15-(t-butyldimethylsilyloxy)-16-phenoxy-17,18,19,20-tetranorprosta-11-enoic acid, methyl ester;
(8R,9S,15S)-9-oxo-15-(t-butyldimethylsilyloxy)-15-cyclohexyl-16,17,18,19,20-pentanorprosta-11-enoic acid, methyl ester;
(8R,9S,15R)-9-oxo-15-(t-butyldimethylsilyloxy)-15-cyclohexyl-16,17,18,19,20-pentanorprosta-11-enoic acid, methyl ester;
(8R,9S,15RS)-9-oxo-15-(t-butyldimethylsilyloxy)-15-cyclohexyl-16,17,18,19,20-pentanorprosta-11-enoic acid, methyl ester;
(8R,9S,15S)-9-oxo-15-(t-butyldimethylsilyloxy)prosta-11-enoic acid, methyl ester;
(8R,9S,15R)-9-oxo-15-(t-butyldimethylsilyloxy)prosta-11-enoic acid, methyl ester;
(8R,9S,15RS)-9-oxo-15-(t-butyldimethylsilyloxy)prosta-11-enoic acid, methyl ester;
(8R,9S,15S)-9-oxo-15-(t-butyldimethylsilyloxy)-16,20-dimethylprosta-11-enoic acid, methyl ester;
(8R,9S,15RS)-9-oxo-15-(t-butyldimethylsilyloxy)-16,20-dimethylprosta-11-enoic acid, methyl ester;
(8R,9S,15S)-9-oxo-15-(t-butyldimethylsilyloxy)-16-phenyl-17,18,19,20-tetranorprosta-11-enoic acid, methyl ester;
(8R,9S,15RS)-9-oxo-15-(t-butyldimethylsilyloxy)-16-phenyl-17,18,19,20-tetranorprosta-11-enoic acid, methyl ester;
(8R,9S,15S)-9-oxo-15-(t-butyldimethylsilyloxy)-15-cyclopentyl-16,17,18,19,20-pentanorprosta-11-enoic acid, methyl ester;
(8R,9S,15RS)-9-oxo-15-(t-butyldimethylsilyloxy)-15-cyclopentyl-16,17,18,19,20-pentanorprosta-11-enoic acid, methyl ester;
(8R,9S,15S)-9-oxo-15-(t-butyldimethylsilyloxy)-16-methyl-16-phenoxy-17,18,19,20-tetranorprosta-11-enoic acid, methyl ester;
(8R,9S,15RS)-9-oxo-15-(t-butyldimethylsilyloxy)-16-methyl-16-phenoxy-17,18,19,20-tetranorprosta-11-enoic acid, methyl ester;
(8R,9S,15S)-9-oxo-15-(t-butyldimethylsilyloxy)-16-methylprosta-11-enoic acid, methyl ester;
(8R,9S,15RS)-9-oxo-15-(t-butyldimethylsilyloxy)-16-methylprosta-11-enoic acid, methyl ester;
(8R,9S,15S)-8-methyl-9-oxo-15-(t-butyldimethylsilyloxy)-15-cyclohexyl-16,17,18,19,20-pentanorprosta-11-enoic acid, methyl ester;
(8R,9S,15RS)-8-methyl-9-oxo-15-(t-butyldimethylsilyloxy)-15-cyclohexyl-16,17,18,19,20-pentanorprosta-11-enoic acid, methyl ester;
(8R,9S,15S)-8-methyl-9-oxo-15-(t-butyldimethylsilyloxy)prosta-11-enoic acid, methyl ester;
(8R,9S,15RS)-8-methyl-9-oxo-15-(t-butyldimethylsilyloxy)prosta-11-enoic acid, methyl ester;
(8R,9S,15S)-9-oxo-15-(t-butyldimethylsilyloxy)-15-methyl-15-cyclohexyl-16,17,18,19,20-pentanorprosta-11-enoic acid, methyl ester;
(8R,9S,15RS)-9-oxo-15-(t-butyldimethylsilyloxy)-15-methyl-15-cyclohexyl-16,17,18,19,20-pentanorprosta-11-enoic acid, methyl ester;
(8R,9S,15S)-9-oxo-15-(t-butyldimethylsilyloxy)-15-methylprosta-11-enoic acid, methyl ester;
(8R,9S,15RS)-9-oxo-15-(t-butyldimethylsilyloxy)-15-methylprosta-11-enoic acid, methyl ester;
(8R,9S,15S)-8-n-butyl-9-oxo-15-(t-butyldimethylsilyloxy)-16-phenoxy-17,18,19,20-tetranorprosta-11-enoic acid, methyl ester;
(8R,9S,15RS)-8-n-butyl-9-oxo-15-(t-butyldimethylsilyloxy)-16-phenoxy-17,18,19,20-tetranorprosta-11-enoic acid, methyl ester;
(8R,9S,15R)-9-oxo-15-(t-butyldimethylsilyloxy)-16-phenoxy-17,18,19,20-tetranorprosta-3,4,11-trienoic acid, methyl ester;
(8R,9S,15RS)-9-oxo-15-(t-butyldimethylsilyloxy)-16-phenoxy-17,18,19,20-tetranorprosta-3,4,11-trienoic acid, methyl ester;

(8R,9S,15S)-8-methyl-9-oxo-15-(t-butyldimethylsilyloxy)-16-phenoxy-17,18,19,20-tetranorprosta-3,4,11-trienoic acid, methyl ester;
(8R,9S,15S)-9-oxo-15-(t-butyldimethylsilyloxy)-15-cyclohexyl-16,17,18,19,20-pentanorprosta-3,4,11-trienoic acid, methyl ester;
(8R,9S,15R)-9-oxo-15-(t-butyldimethylsilyloxy)-15-cyclohexyl-16,17,18,19,20-pentanorprosta-3,4,11-trienoic acid, methyl ester;
(8R,9S,15RS)-9-oxo-15-(t-butyldimethylsilyloxy)-15-cyclohexyl-16,17,18,19,20-pentanorprosta-3,4,11-trienoic acid, methyl ester;
(8R,9S,15S)-9-oxo-15-(t-butyldimethylsilyloxy)prosta-3,4,11-trienoic acid, methyl ester;
(8R,9S,15R)-9-oxo-15-(t-butyldimethylsilyloxy)prosta-3,4,11-trienoic acid, methyl ester;
(8R,9S,15RS)-9-oxo-15-(t-butyldimethylsilyloxy)prosta-3,4,11-trienoic acid, methyl ester;
(8R,9S,15S)-9-oxo-15-(t-butyldimethylsilyloxy)-16,20-dimethylprosta-3,4,11-trienoic acid, methyl ester;
(8R,9S,15RS)-9-oxo-15-(t-butyldimethylsilyloxy)-16,20-dimethylprosta-3,4,11-trienoic acid, methyl ester;
(8R,9S,15S)-9-oxo-15-(t-butyldimethylsilyloxy)-16-phenyl-17,18,19,20-tetranorprosta-3,4,11-trienoic acid, methyl ester;
(8R,9S,15RS)-9-oxo-15-(t-butyldimethylsilyloxy)-16-phenyl-17,18,19,20-tetranorprosta-3,4,11-trienoic acid, methyl ester;
(8R,9S,15S)-9-oxo-15-(t-butyldimethylsilyloxy)-15-cyclopentyl-16,17,18,19,20-pentanorprosta-3,4,11-trienoic acid, methyl ester;
(8R,9S,15RS)-9-oxo-15-(t-butyldimethylsilyloxy)-15-cyclopentyl-16,17,18,19,20-pentanorprosta-3,4,11-trienoic acid, methyl ester;
(8R,9S,15S)-9-oxo-15-(t-butyldimethylsilyloxy)-16-methyl-16-phenoxy-17,18,19,20-tetranorprosta-3,4,11-trienoic acid, methyl ester;
(8R,9S,15RS)-9-oxo-15-(t-butyldimethylsilyloxy)-16-methyl-16-phenoxy-17,18,19,20-tetranorprosta-3,4,11-trienoic acid, methyl ester;
(8R,9S,15S)-9-oxo-15-(t-butyldimethylsilyloxy)-16-methylprosta-3,4,11-trienoic acid, methyl ester;
(8R,9S,15RS)-9-oxo-15-(t-butyldimethylsilyloxy)-16-methylprosta-3,4,11-trienoic acid, methyl ester;
(8R,9S,15S)-9-oxo-15-(t-butyldimethylsilyloxy)-15-methyl-15-cyclohexyl-16,17,18,19,20-pentanorprosta-3,4,11-trienoic acid, methyl ester;
(8R,9S,15RS)-9-oxo-15-(t-butyldimethylsilyloxy)-15-methyl-15-cyclohexyl-16,17,18,19,20-pentanorprosta-3,4,11-trienoic acid, methyl ester;
(8R,9S,15S)-9-oxo-15-methyl-15-(t-butyldimethylsilyloxy)prosta-3,4,11-trienoic acid, methyl ester;
(8R,9S,15RS)-9-oxo-15-methyl-15-(t-butyldimethylsilyloxy)prosta-3,4,11-trienoic acid, methyl ester;
(±)-9-oxo-15-(t-butyldimethylsilyloxy)-16-phenoxy-17,18,19,20-tetranorprosta-3,4,11-trienoic acid, methyl ester;
(±)-9-oxo-15-(t-butyldimethylsilyloxy)-15-cyclohexyl-16,17,18,19,20-pentanorprosta-3,4,11-trienoic acid, methyl ester;
(±)-9-oxo-15-(t-butyldimethylsilyloxy)prosta-3,4,11-trienoic acid, methyl ester;
(±)-9-oxo-15-(t-butyldimethylsilyloxy)-16,20-dimethylprosta-3,4,11-trienoic acid, methyl ester;
(±)-9-oxo-15-(t-butyldimethylsilyloxy)-16-phenyl-17,18,19,20-tetranorprosta-3,4,11-trienoic acid, methyl ester;
(±)-9-oxo-15-(t-butyldimethylsilyloxy)-20-butylprosta-3,4,11-trienoic acid, methyl ester;
(±)-9-oxo-15-(t-butyldimethylsilyloxy)-20,20,20-trifluoroprosta-3,4,11-trienoic acid, methyl ester;
(±)-9-oxo-15-(t-butyldimethylsilyloxy)-15-cyclopentyl-16,17,18,19,20-pentanorprosta-3,4,11-trienoic acid, methyl ester;
(±)-9-oxo-15-(t-butyldimethylsilyloxy)-16-methyl-16-phenoxy-17,18,19,20-tetranorprosta-3,4,11-trienoic acid, methyl ester;
(±)-9-oxo-15-(t-butyldimethylsilyloxy)-16-methylprosta-3,4,11-trienoic acid, methyl ester;
(±)-9-oxo-15-(t-butyldimethylsilyloxy)-15-methyl-15-cyclohexyl-16,17,18,19,20-pentanorprosta-3,4,11-trienoic acid, methyl ester;
(±)-9-oxo-15-methyl-15-(t-butyldimethylsilyloxy)prosta-3,4,11-trienoic acid, methyl ester; and
(±)-8-n-butyl-9-oxo-15-(t-butyldimethylsilyloxy)-16-phenoxy-17,18,19,20-tetranorprosta-3,4,11-trienoic acid, methyl ester.

EXAMPLE 1

Preparation of (8R,15S)-9-oxo-15-hydroxy-16-phenoxy-17,18,19,20-tetranorprosta-5(Z),11-dienoic acid, methyl ester and Related Compounds of Formula (I)

A. (8R,15S)-9-oxo-15-(t-butyldimethylsilyloxy)-16-phenoxy-17,18,19,20-tetranorprosta-5(Z),11-dienoic acid, methyl ester, the compound of formula (8) where X is —CH=CH— and m is 3, (150 mg, 0.300 mmol) was stirred with 3 ml of a solution containing 2.5% of hydrofluoric acid and 2.5% of water in acetonitrile. After 25 min, the mixture was poured into 20 ml of water and extracted with methylene chloride (3×5 ml). The combined organic extracts were dried over anhydrous magnesium sulfate and the solvent removed under reduced pressure. The residue was purified by column chromatography (silica gel, hexane/ethyl acetate, 80/20) to give (8R,15S)-9-oxo-15-hydroxy-16-phenoxy-17,18,19,20-tetranorprosta-5(Z),11-dienoic acid, methyl ester, the compound of formula (I) where X is —CH=CH— and m is 3, 104 mg; $[\alpha]_D = -25.2°$ (C=1.048, CHCl$_3$)

B. Similarly, following the procedure of A above and replacing (8R,15S)-9-oxo-15-(t-butyldimethylsilyloxy)-16-phenoxy-17,18,19,20-tetranorprosta-5(Z),11-dienoic acid, methyl ester with the appropriate compound of formula (8) where X is —CH=CH— and m is 3, the following compounds of formula (I) were prepared:

(±)-9-oxo-15-hydroxy-16-phenoxy-17,18,19,20-tetranorprosta-5(Z),11-dienoic acid, methyl ester; MS 386(M+);

(8R,15R)-9-oxo-15-hydroxy-16-phenoxy-17,18,19,20-tetranorprosta-5(Z),11-dienoic acid, methyl ester; $[\alpha]_D = -16.76°$ (C=1.038, CHCl$_3$);

(8R,15RS)-8-methyl-9-oxo-15-hydroxy-16-phenoxy-17,18,19,20-tetranorprosta-5(Z),11-dienoic acid, methyl ester; MS 400 (M+);

(±)-9-oxo-15-hydroxy-15-cyclohexyl-16,17,18,19,20-pentanorprosta-5(Z),11-dienoic acid, methyl ester; MS 362 (M+) and (±)-9-oxo-15-hydroxyprosta-5(Z),11-dienoic acid, methyl ester; MS 350 (M+).

C. Similarly, following the procedure of A above and replacing (8R,15S)-9-oxo-15-(t-butyldimethylsilyloxy)-16-phenoxy-17,18,19,20-tetranorprosta-5(Z),11-dienoic acid, methyl ester with the appropriate compound of formula (8) where X is —CH$_2$CH$_2$— and m is 3, the following compound of formula (I) was prepared:

(8R,15S)-9-oxo-15-hydroxy-16-phenoxy-17,18,19,20-tetranorprosta-11-enoic acid, methyl ester; [α]$_D$= −16.1° (C=0.225, CHCl$_3$).

D. Similarly, following the procedure of A above and replacing (8R,15S)-9-oxo-15-(t-butyldimethylsilyloxy)-16-phenoxy-17,18,19,20-tetranorprosta-5(Z),11-dienoic acid, methyl ester with the appropriate compound of formula (8) where X is —CH$_2$CH=C=CH— and m is 1, the following compound of formula (I) was prepared:

(8R,15S)-9-oxo-15-hydroxy-16-phenoxy-17,18,19,20-tetranorprosta-3,4,11-trienoic acid, methyl ester; [α]$_D$= −28.9° (C=0.301, CHCl$_3$).

E. Similarly, following the procedure of A above and replacing (8R,15S)-9-oxo-15-(t-butyldimethylsilyloxy)-16-phenoxy-17,18,19,20-tetranorprosta-5(Z),11-dienoic acid, methyl ester with the appropriate compound of formula (7), the following compounds of formula (8) where X is —CH=CH— and m is 3, or where X is —CH$_2$CH$_2$— and m is 3, or where X is —CH$_2$CH=C=CH— and m is 1, are prepared:

[(±)-9-oxo-15-hydroxy-16-phenyl-17,18,19,20-tetranorprosta-5(Z),11-dienoic acid, methyl ester;
[(±)-9-oxo-15-hydroxy-16,20-dimethylprosta-5(Z),11-dienoic acid, methyl ester;
(±)-9-oxo-15-hydroxy-20-butylprosta-5(Z),11-dienoic acid, methyl ester;
(±)-9-oxo-15-hydroxy-20,20,20-trifluoroprosta-5(Z),11-dienoic acid, methyl ester;
(±)-9-oxo-15-hydroxy-15-cyclopentyl-16,17,18,19,20-pentanorprosta-5(Z),11-dienoic acid, methyl ester;
[(±)-9-oxo-15-hydroxy-16-methyl-16-phenoxy-17,18,19,20-tetranorprosta-5(Z),11-dienoic acid, methyl ester;
[(±)-9-oxo-15-hydroxy-16-methylprosta-5(Z),11-dienoic acid, methyl ester;
[(8R,15RS)-8-methyl-9-oxo-15-hydroxy-15-cyclohexyl-16,17,18,19,20-pentanorprosta-5(Z),11-dienoic acid, methyl ester;
[(8R,15RS)-8-methyl-9-oxo-15-hydroxy-prosta-5(Z),11-dienoic acid, methyl ester;
[(±)-9-oxo-15-hydroxy-15-methyl-15-cyclohexyl-16,17,18,19,20-pentanorprosta-5(Z),11-dienoic acid, methyl ester;
[(±)-9-oxo-15-hydroxy-15-methylprosta-5(Z),11-dienoic acid, methyl ester;
[(8R,15RS)-8-n-butyl-9-oxo-15-hydroxy-16-phenoxy-17,18,19,20-tetranorprosta-5(Z),11-dienoic acid, methyl ester;
[(8R,15RS)-9-oxo-15-hydroxy-16-phenoxybut-1′-yl)-17,18,19,20-tetranorprosta-5(Z),11-dienoic acid, methyl ester;
[(8R,15S)-9-oxo-15-hydroxy-15-cyclohexyl-16,17,18,19,20-pentanorprosta-5(Z),11-dienoic acid, methyl ester;
[(8R,15R)-9-oxo-15-hydroxy-15-cyclohexyl-16,17,18,19,20-pentanorprosta-5(Z),11-dienoic acid, methyl ester;
[(8R,15RS)-9-oxo-15-hydroxy-15-cyclohexyl-16,17,18,19,20-pentanorprosta-5(Z),11-dienoic acid, methyl ester;
[(8R,15S)-9-oxo-15-hydroxy-prosta-5(Z),II-dienoic acid, methyl ester;
[(8R,15R)-9-oxo-15-hydroxy-prosta-5(Z),11-dienoic acid, methyl ester;
[(8R,15RS)-9-oxo-15-hydroxy-prosta-5(Z),11-dienoic acid, methyl ester;
[((8R,15S)-9-oxo-15-hydroxy-16,20-dimethylprosta-5(Z),11-dienoic acid, methyl ester;
[((8R,15RS)-9-oxo-15-hydroxy-16,20-dimethylprosta-5(Z),11-dienoic acid, methyl ester;
[(8R,15S)-9-oxo-15-hydroxy-16-phenyl-17,18,19,20-tetranorprosta-5(Z),11-dienoic acid, methyl ester;
[(8R,15RS)-9-oxo-15-hydroxy-16-phenyl-17,18,19,20-tetranorprosta-5(Z),11-dienoic acid, methyl ester;
[(8R,15S)-9-oxo-15-hydroxy-15-cyclopentyl-16,17,18,19,20-pentanorprosta-5(Z),11-dienoic acid, methyl ester;
[(8R,15RS)-9-oxo-15-hydroxy-15-cyclopentyl-16,17,18,19,20-pentanorprosta-5(Z),11-dienoic acid, methyl ester;
[(8R,15S)-9-oxo-15-hydroxy-16-methyl-16-phenoxy-17,18,19,20-tetranorprosta-5(Z),11-dienoic acid, methyl ester;
[(8R,15RS)-9-oxo-15-hydroxy-16-methyl-16-phenoxy-17,18,19,20-tetranorprosta-5(Z),11-dienoic acid, methyl ester;
[(8R,15R)-9-oxo-15-hydroxy-16-methylprosta-5(Z),11-dienoic acid, methyl ester;
[(8R,15RS)-9-oxo-15-hydroxy-16-methylprosta-5(Z),11-dienoic acid, methyl ester;
[(8R,15R)-9-oxo-15-hydroxy-15-methyl-15-cyclohexyl-16,17,18,19,20-pentanorprosta-5(Z),11-dienoic acid, methyl ester;
[(8R,15RS)-9-oxo-15-hydroxy-15-methyl-15-cyclohexyl-16,17,18,19,20-pentanorprosta-5(Z),11-dienoic acid, methyl ester;
[(8R,15S)-9-oxo-15-hydroxy-15-methyl-16-methylprosta-5(Z),11-dienoic acid, methyl ester;
[(8R,15RS)-9-oxo-15-hydroxy-15-methyl-16-methylprosta-5(Z),11-dienoic acid, methyl ester;
(8R,15R)-9-oxo-15-hydroxy-16-phenoxy-17,18,19,20-tetranorprosta-11-enoic acid, methyl ester;
(8R,15RS)-9-oxo-15-hydroxy-16-phenoxy-17,18,19,20-tetranorprosta-11-enoic acid, methyl ester;
(8R,15S)-8-methyl-9-oxo)-15-hydroxy-16-phenoxy-17,18,19,20-tetranorprosta-11-enoic acid, methyl ester;
(8R,15S)-9-oxo-15-hydroxy-15-cyclohexyl-16,17,18,19,20-pentanorprosta-11enoic acid, methyl ester;
(8R,15R)-9-oxo-15-hydroxy-15-cyclohexyl-16,17,18,19,20-pentanorprosta-11-enoic acid, methyl ester;
(8R,15RS)-9-oxo-15-hydroxy-15-cyclohexyl-16,17,18,19,20-pentanorprosta-11-enoic acid, methyl ester;
(8R,15S)-9-oxo-15-hydroxyprosta-11-enoic acid, methyl ester;
(8R,15R)-9-oxo-15-hydroxyprosta-11-enoic acid, methyl ester;
(8R,15RS)-9-oxo-15-hydroxy-prosta-11-enoic acid, methyl ester;
(8R,15S)-9-oxo-15-hydroxy-16,20-dimethylprosta-11-enoic acid, methyl ester;
(8R,15RS)-9-oxo-15hydroxy-16,20-dimethylprosta-11-enoic acid, methyl ester;
(8R,15S)-9-oxo-15-hydroxy-16-phenyl-17,18,19,20-tetranorprosta-11-enoic acid, methyl ester;
(8R,15RS)-9-oxo-15-hydroxy-16-phenyl-17,18,19,20-tetranorprosta-11-enoic acid, methyl ester;
(8R,15S)-9-oxo-15-hydroxy-15-cyclopentyl-16,17,18,19,20-pentanorprosta-11-enoic acid, methyl ester;

(8R,15RS)-9-oxo-15-hydroxy-15-cyclopentyl-16,17,18,19,20-pentanorprosta-11-enoic acid, methyl ester;

(8R,15S)-9-oxo-15-hydroxy-16-methyl-16-phenoxy-17,18,19,20-tetranorprosta-11-enoic acid, methyl ester;

(8R,15RS)-9-oxo-15-hydroxy-16-methyl-16-phenoxy-17,18,19,20-tetranorprosta-11-enoic acid, methyl ester;

(8R,15S)-9-oxo-15-hydroxy-16-methylprosta-11-enoic acid, methyl ester;

(8R,15RS)-9-oxo-15-hydroxy-16-methylprosta-11-enoic acid, methyl ester;

(8R,15S)-8-methyl-9-oxo-15-hydroxy-15-cyclohexyl-16,17,18,19,20-pentanorprosta-11-enoic acid, methyl ester;

(8R,15RS)-8-methyl-9-oxo-15-hydroxy-15-cyclohexyl-16,17,18,19,20-pentanorprosta-11-enoic acid, methyl ester;

(8R,15S)-8-methyl-9-oxo-15-hydroxyprosta-11-enoic acid, methyl ester;

(8R,15RS)-8-methyl-9-oxo-15-hydroxyprosta-11-enoic acid, methyl ester;

(8R,15S)-9-oxo-15-hydroxy-15-methyl-15-cyclohexyl-16,17,18,19,20-pentanorprosta-11-enoic acid, methyl ester;

(8R,15RS)-9oxo-15-hydroxy-15-methyl-15-cyclohexyl-16,17,18,19,20-pentanorprosta-11-enoic acid, methyl ester;

(8R,15S)-9-oxo-15-hydroxy-15-methylprosta-11-enoic acid, methyl ester;

(8R,15RS)-9-oxo-15-hydroxy-15-methylprosta-11-enoic acid, methyl ester;

(8R,15S)-8-n-butyl-9-oxo-15-hydroxy-16-phenoxy-17,18,19,20-tetranorprosta-11-enoic acid, methyl ester;

(8R,15RS)-8-n-butyl-9-oxo-15-hydroxy-16-phenoxy-17,18,19,20-tetranorprosta-11-enoic acid, methyl ester;

(8R,15R)-9-oxo-15-hydroxy-16-phenoxy-17,18,19,20-tetranorprosta-3,4,11-trienoic acid, methyl ester;

(8R,15RS)-9-oxo-15-hydroxy-16-phenoxy-17,18,19,20-tetranorprosta-3,4,11-trienoic acid, methyl ester;

(8R,15S)-8-methyl-9-oxo-15-hydroxy-16-phenoxy-17,18,19,20-tetranorprosta-3,4,11-trienoic acid, methyl ester;

(8R,15S)-9-oxo-15-hydroxy-15-cyclohexyl-16,17,18,19,20-pentanorprosta-3,4,11-trienoic acid, methyl ester;

(8R,15R)-9-oxo-15-hydroxy-15-cyclohexyl-16,17,18,19,20-pentanorprosta-3,4,11-trienoic acid, methyl ester;

(8R,15RS)-9-oxo-15-hydroxy-15-cyclohexyl-16,17,18,19,20-pentanorprosta-3,4,11-trienoic acid, methyl ester;

(8R,15S)-9-oxo-15-hydroxyprosta-3,4,11-trienoic acid, methyl ester;

(8R,15R)-9-oxo-15-hydroxyprosta-3,4,11-trienoic acid, methyl ester;

(8R,15RS)-9-oxo-15-hydroxyprosta-3,4,11-trienoic acid, methyl ester;

(8R,15S)-9-oxo-15-hydroxy-16,20-dimethylprosta-3,4,11-trienoic acid, methyl ester;

(8R,15RS)-9-oxo-15-hydroxy-16,20-dimethylprosta-3,4,11-trienoic acid, methyl ester;

(8R,15S)-9-oxo-15-hydroxy-16-phenyl-17,18,19,20-tetranorprosta-3,4,11-trienoic acid, methyl ester;

(8R,15RS)-9-oxo-15-hydroxy-16-phenyl-17,18,19,20-tetranorprosta-3,4,11-trienoic acid, methyl ester;

(8R,15S)-9-oxo-15-hydroxy-15-cyclopentyl-16,17,18,19,20-pentanorprosta-3,4,11-trienoic acid, methyl ester;

(8R,15RS)-9-oxo-15-hydroxy-15-cyclopentyl-16,17,18,19,20-pentanorprosta-3,4,11-trienoic acid, methyl ester;

(8R,15S)-9-oxo-15-hydroxy-16-methyl-16-phenoxy-17,18,19,20-tetranorprosta-3,4,11-trienoic acid, methyl ester;

(8R,15RS)-9-oxo-15-hydroxy-16-methyl-16-phenoxy-17,18,19,20-tetranorprosta-3,4,11-trienoic acid, methyl ester;

(8R,15S)-9-oxo-15-hydroxy-16-methylprosta-3,4,11-trienoic acid, methyl ester;

(8R,15RS)-9-oxo-15-hydroxy-16-methylprosta-3,4,11-trienoic acid, methyl ester;

(8R,15S)-9-oxo-15-hydroxy-15-methyl-15-cyclohexyl-16,17,18,19,20-pentanorprosta-3,4,11-trienoic acid, methyl ester;

(8R,15RS)-9-oxo-15-hydroxy-15-methyl-15-cyclohexyl-16,17,18,19,20-pentanorprosta-3,4,11-trienoic acid, methyl ester;

(8R,15S)-9-oxo-15-methyl-15-hydroxyprosta-3,4,11-trienoic acid, methyl ester;

(8R,15RS)-9-oxo-15-methyl-15-hydroxyprosta-3,4,11-trienoic acid, methyl ester;

(±)-9-oxo-15-hydroxy-16-phenoxy-17,18,19,20-tetranorprosta-3,4,11-trienoic acid, methyl ester;

(±)-9-oxo-15-hydroxy-15-cyclohexyl-16,17,18,19,20-pentanorprosta-3,4,11-trienoic acid, methyl ester;

(±)-9-oxo-15-hydroxyprosta-3,4,11-trienoic acid, methyl ester;

(±)-9-oxo-15-hydroxy-16,20-dimethylprosta-3,4,11-trienoic acid, methyl ester;

(±)-9-oxo-15-hydroxy-16-phenyl-17,18,19,20-tetranorprosta-3,4,11-trienoic acid, methyl ester;

(±)-9-oxo-15-hydroxy-20-butylprosta-3,4,11-trienoic acid, methyl ester;

(±)-9-oxo-15-hydroxy-20,20,20-trifluoroprosta-3,4,11-trienoic acid, methyl ester;

(±)-9-oxo-15-hydroxy-15-cyclopentyl-16,17,18,19,20-pentanorprosta-3,4,11-trienoic acid, methyl ester;

(±)-9-oxo-15-hydroxy-16-methyl-16-phenoxy-17,18,19,20-tetranorprosta-3,4,11-trienoic acid, methyl ester;

(±)-9-oxo-15-hydroxy-16-methyl-prosta-3,4,11-trienoic acid, methyl ester;

(±)-9-oxo-15-hydroxy-15-methyl-15-cyclohexyl-16,17,18,19,20-pentanorprosta-3,4,11-trienoic acid, methyl ester;

(±)-9-oxo-15-methyl-15-hydroxy-prosta-3,4,11-trienoic acid, methyl ester; and (±)-8-n-butyl-9-oxo-15-hydroxy-16-phenoxy-17,18,19,20-tetranorprosta-3,4,11-trienoic acid, methyl ester.

EXAMPLE 2

Preparation of (8R,15S)-9-oxo-15-hydroxy-16-phenoxy-17,18,19,20-tetranorprosta-5(Z),11-dienoic acid and Related Compounds of Formula (I) where $R_1$ is hydrogen A. Powdered type II crude (Steapsin) porcine pancrease lipase (E.C. 3.1.1.3) (Sigma, 100 mg) is added to 100 ml of Tris-HCl pH 7.5 buffer, and the solution allowed to equilibrate at 37° C. for 10 minutes. To this mixture is added 30 mg of (8R,15S)-9-oxo-15-hydroxy-16-phenoxy-17,18,19,20-tetranorprosta-5(Z),11-dienoic acid, methyl ester in 2.5 ml of acetone, and the solution is stirred for 3 hours at 37° C. The mixture is cooled to 0° C. and carefully acidified to pH 4 with 10% hydrochloric acid and immediately extracted four times with ether. The ether extracts are washed with saturated sodium chloride solution and dried over anhydrous magnesium sulfate. Removal of the solvent under reduced pressure gives (8R,15S)-9-oxo-15-hydroxy-16-phenoxy-17,18,19,20-tetranorprosta-5(Z),11-dienoic acid.

B. Similarly, following the procedure of A above and replacing (8R,15S)-9-oxo-15-hydroxy-16-phenoxy-17,18,19,20-tetranorprosta-5(Z),11-dienoic acid, methyl ester with the appropriate compound of formula (I) where where $R_1$ is lower alkyl, the following compounds of formula (I) where $R_1$ is hydrogen are prepared:

(±)-9-oxo-15-hydroxy-16-phenoxy-17,18,19,20-tetranorprosta- 5(Z),11-dienoic acid;
(8R,15R)-9-oxo-15-hydroxy-16-phenoxy-17,18,19,20-tetranorprosta-5(Z),11-dienoic acid;
(8R,15RS)-8-methyl-9-oxo-15-hydroxy-16-phenoxy-17,18,19,20-tetranorprosta-5(Z),11-dienoic acid;
(±)-9-oxo-15-hydroxy-15-cyclohexyl-16,17,18,19,20-pentanorprosta-5(Z),11-dienoic acid;
(±)-9-oxo-15-hydroxyprosta-5(Z),11-dienoic acid, methyl ester;
(8R,15S)-9-oxo-15-hydroxy-16-phenoxy-17,18,19,20-tetranorprosta-11-enoic acid; and
(8R,15S)-9-oxo-15-hydroxy-16-phenoxy-17,18,19,20-tetranorprosta-3,4,11-trienoic acid.

EXAMPLE 3

Preparation of (8R,15S)-8-methyl-9-oxo-15-hydroxy-16-phenoxy-17,18,19,20-tetranorprosta-5(Z),11-dienoic acid and Related Compounds of Formula (I) where $R_1$ is hydrogen and $R_2$ is lower alkyl To a solution of 200 mg of (8R,15S)-8-methyl-9-oxo-15-hydroxy-16-phenoxy-17,18,19,20-tetranorprosta-5(Z),11-dienoic acid, methyl ester, in 10 ml of methanol is added 1.5 ml of water and 200 mg of potassium carbonate. The mixture is stirred for 40 hours at room temperature, and solvent removed under reduced pressure. The residue is diluted with water and extracted with methylene chloride to eliminate non-acidic products. The aqueous solution is saturated with sodium potassium tartrate, 20 ml of ethyl acetate added and the mixture cooled to 0° C. A solution of oxalic acid (250 mg in 2 ml of water) is then added while stirring, the aqueous phase separated and washed with cold ethyl acetate. The combined organic extracts are then washed with sodium potassium tartrate and evaporated to dryness under reduced pressure, to give (8R,15S)-8-methyl-9-oxo-15-hydroxy-16-phenoxy-17,18,19,20-tetranorprosta-5(Z),11-dienoic acid.

Similarly, any compound of formula (I) where $R_1$ is hydrogen and $R_2$ is lower alkyl is prepared from the compound of formula (I) where $R_1$ and $R_2$ are lower alkyl.

EXAMPLE 4

Preparation of (8R,15S)-9-oxo-15-hydroxy-16-phenoxy-17,18,19,20-tetranorprosta-5(Z),11-dienoic acid, methyl ester and Related Compounds of Formula (I)

A. To a solution of (8R,15S)-9-oxo-15-hydroxy-16-phenoxy-17,18,19,20-tetranorprosta-5(Z),11-dienoic acid in 10 ml of diethylether is added excess ethereal diazomethane, i.e. until the yellow color persists. Evaporation of the solvent gives (8R,15S)-9-oxo-15-hydroxy-16-phenoxy-17,18,19,20-tetranorprosta-5(Z),11-dienoic acid, methyl ester.

B. In like manner, but starting with the appropriate compounds of formula (I) where $R_1$ is hydrogen and optionally substituting an appropriate diazoalkane, the following exemplary compounds of formula (I) where $R_1$ is lower alkyl are obtained.

(±)-9-oxo-15-hydroxy-16-phenoxy-17,18,19,20-tetranorprosta-5(Z),11-dienoic acid, methyl ester;
(8R,15R)-9-oxo-15-hydroxy-16-phenoxy-17,18,19,20-tetranorprosta-5(Z),11-dienoic acid, methyl ester;
(8R,15RS)-8-methyl-9-oxo-15-hydroxy-16-phenoxy-17,18,19,20-tetranorprosta-5(Z),11-dienoic acid, methyl ester;
(±)-9-oxo-15-hydroxy-15-cyclohexyl-16,17,18,19,20-pentanorprosta-5(Z),11-dienoic acid, methyl ester;
(±)-9-oxo-15-hydroxyprosta-5(Z),11-dienoic acid, methyl ester, methyl ester;
(8R,15S)-9-oxo-15-hydroxy-16-phenoxy-17,18,19,20-tetranorprosta-11-enoic acid, methyl ester;
(8R,15S)-9-oxo-15-hydroxy-16-phenoxy-17,18,19,20-tetranorprosta-3,4,11-trienoic acid, methyl ester;
(8R,15S)-9-oxo-15-hydroxy-16-phenoxy-17,18,19,20-tetranorprosta-5(Z),11-dienoic acid, ethyl ester;
(8R,15S)-9-oxo-15-hydroxy-16-phenoxy-17,18,19,20-tetranorprosta-11-enoic acid, ethyl ester;
(8R,15S)-9-oxo-15-hydroxy-16-phenoxy-17,18,19,20-tetranorprosta-3,4,11-trienoic acid, ethyl ester; and
(8R,15S)-9-oxo-15-hydroxy-16-phenoxy-17,18,19,20-tetranorprosta-5(Z),11-dienoic acid, hexyl ester.

EXAMPLE 5

Preparation of (8R,15S)-9-oxo-15-hydroxy-16-phenoxy-17,18,19,20-tetranorprosta-5(Z),11-dienoic acid, sodium salt and Related Compounds of Formula (I)

A. To a solution of (8R,15S)-9-oxo-15-hydroxy-16-phenoxy-17,18,19,20-tetranorprosta-5(Z),11-dienoic acid in methanol at −20° C. one molar equivalent of sodium bicarbonate dissolved in water is added. The mixture is allowed to warm to room temperature, solvent removed under reduced pressure and the residue dried under high vacuum, to give (8R,15S)-9-oxo-15-hydroxy-16-phenoxy-17,18,19,20-tetranorprosta-5(Z),11-dienoic acid, sodium salt.

B. In like manner, but starting with the appropriate compounds of formula (I) where $R_1$ is hydrogen and optionally substituting an appropriate base for sodium bicarbonate, other exemplary compounds of formula (I) where $R_1$ is a pharmaceutically acceptable base are prepared.

EXAMPLE 6

In vitro gastric acid secretion assay (Inhibition of histamine-stimulated $^{14}$C-aminopyrine uptake).

A. Isolation of rabbit gastric glands. Female albino rabbits weighing 2–3 Kg were sacrificed with an intravenous injection of 100 mg/Kg of sodium pentobarbital. The abdomen was immediately opened and the stomach excised. The stomach was cut open along the lesser curvature and emptied. The cardiac and antral regions of the stomach were discarded and the corpus was rinsed several times with phosphate-buffered saline (PBS: NaCl, 149.6 mM; K$_2$HPO$_4$, 3.0 mM; NaH$_2$PO$_4$, 0.64 mM; pH=7.3) and blotted with tissue paper. The mucosa were then removed from the corpus by blunt dissection and minced with scissors. The minced pieces were then added to 50 mL of collagenase-enzyme solution (NaCl, 130.0 mM; NaHCO$_3$, 12.0 mM; NaH$_2$PO$_4$, 3.0 mM; Na$_2$HPO$_4$, 3.0 mM; K$_2$HPO$_4$, 3.0 mM; MgSO$_4$, 2.0 mM; CaCl$_2$, 1.0 mM; collagenase (Type 1, Sigma), 1 mg/mL; rabbit albumin, 1 mg/mL; glucose, 2 mg/mL; pH=7.4) and incubated at 37° C. for 45–60 minutes in an orbital shaking incubator at 180 rpm. After incubation, the mucosal suspension was filtered through a nylon screen into a conical tube and the filtrate was allowed to stand for 15 minutes. In the tube, the gastric glands rapidly settled to the bottom while the isolated cells remained in suspension. The cell suspension was then decanted, and the glands washed twice with Hank's balanced salt solution (HBSS: pH=7.4) and finally diluted 1:20 (v/v) with HBSS.

B. $^{14}$C-aminopyrine (AP: dimethylaminoantipyrine) uptake.

Triplicate aliquots of 400 µL each of the gastric gland suspension from part A of this Example were incubated with 50 mM HEPES (pH=7.4) and 0.03 µCi of $^{14}$C-AP in a 1.5 mL microcentrifuge tube. Histamine and the prostaglandin to be evaluated were added to the samples. Sodium thiocyanate (20 mM) was added to a set of tubes to estimate nonspecifically trapped tissue counts. Each sample was incubated at 37° C. for 20 minutes in a horizontal position submerged in bath water and shaken at 150 rpm. After incubation, the sample was spun in a Beckman microcentrifuge for 1 minute. The supernatant of the centrifuged sample was removed by vacuum suction, and the pellet was resuspended in 1 mL of HBSS and spun again. After removal of the supernatant, the bottom 2 cm of the tube containing the pellet was cut from the rest of the tube and placed in a scintillation vial. Beckman BTS-450 tissue solubilizer (200 µL) was added to each pellet for overnight digestion. Econofluor was added to each vial on the next day, and the samples were counted in a Packard Tri-Carb scintillation counter.

EXAMPLE 7

Determination of Antihypertensive Activity

The antihypertensive effects of the prostaglandin-like compounds are evaluated in spontaneously hypertensive rats (SHR/NCrlBR). Under ether anesthesia, femoral arterial and venous cannulae are implanted and the rats are restrained in a supine position. After recovery from the anesthesia, lidocaine is administered. Blood pressures are obtained via the femoral arterial cannula and recorded on a Beckman R611 polygraph. Groups of four rats are studied for each compound. Vehicle is administered at the beginning of the study and compound is intravenously administered at 30 min intervals thereafter, at increasing doses of 1, 3, 10, 30 and 100 µg/Kg. Baseline mean arterial blood pressure is the blood pressure immediately prior to the first dose of the compound. ED$_{20}$s are calculated from a linear regression of the percent decrease of mean blood pressures following each dose of the compound. The duration of activity is determined based on the recovery to 90% of the control blood pressure following the 100 µg/Kg, i.v., dose.

What is claimed is:

1. A compound of the formula:

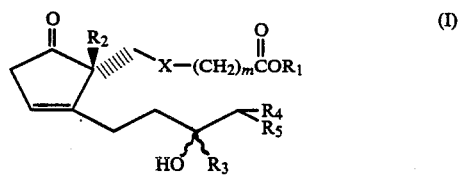

wherein:

m is 1 or 3;

R$_1$ is hydrogen or alkyl of 1–6 carbon atoms;

R$_2$ is hydrogen or lower alkyl of 1–4 carbon atoms;

R$_3$ and R$_4$ are independently hydrogen or methyl;

R$_5$ is alkyl of 4–10 carbon atoms, CF$_3$(CH$_2$)$_n$— in which n is an integer of 3–5, cycloalkyl of 4–8 carbon atoms, or phenyl, benzyl or phenoxy in which any phenyl group may be optionally substituted with one or two substitutents chosen from lower alkyl of 1–4 carbon atoms, lower alkoxy of 1–4 carbon atoms, lower thioalkyl of 1–4 carbon atoms, halogen, trifluoromethyl and trifluoromethoxy; or R$_4$ and R$_5$ taken together with the carbon to which they are attached represent cycloalkyl of 4–8 carbon atoms;

X is cis —CH=CH— or —CH$_2$CH$_2$— when m is 3, or

X is —CH$_2$CH=C=CH— when m is 1;

and the wavy lines represent the α or β configuration with the proviso that when one wavy line is α the other is β;

or a pharmaceutically acceptable, non-toxic salt thereof.

2. A compound of claim 1, wherein X is —CH=CH— and m is 3.

3. A compound of claim 2, wherein R$_2$ is hydrogen or methyl and R$_3$ is hydrogen.

4. A compound of claim 3, wherein R$_1$ is methyl.

5. A compound of claim 4, wherein R$_4$ is hydrogen and R$_5$ is alkyl of 4–6 carbon atoms or optionally substituted phenoxy.

6. A racemic compound of claim 5, wherein R$_2$ is hydrogen and R$_5$ is phenoxy, namely (±)-9-oxo-15-hydroxy-16-phenoxy-17,18,19,20-tetranorprosta-5(Z),11-dienoic acid, methyl ester.

7. An optical isomer of the compound of claim 6, namely (8R,15S)-9-oxo-15-hydroxy-16-phenoxy-17,18,19,20-tetranorprosta-5(Z),11-dienoic acid, methyl ester.

8. A compound of claim 5, wherein R$_2$ is methyl and R$_5$ is phenoxy, namely (8R,15RS)-8-methyl-9-oxo-15-hydroxy-16-phenoxy-17,18,19,20-tetranorprosta-5(Z),11-dienoic acid, methyl ester.

9. A racemic compound of claim 5, wherein $R_2$ is hydrogen and $R_5$ is n-butyl, namely ($\pm$)-9-oxo-15-hydroxyprosta-5(Z),11-dienoic acid, methyl ester.

10. An optical isomer of the compound of claim 9, namely (8R,15S)-9-oxo-15-hydroxyprosta-5(Z),11-dienoic acid, methyl ester.

11. A racemic compound of claim 4, wherein $R_2$ is hydrogen, and $R_4$ and $R_5$ taken together with the carbon to which they are attached represent cyclohexyl, namely ($\pm$)-9-oxo-15-hydroxy-15-cyclohexyl-16,17,18,19,20-pentanorprosta-5(Z),11-dienoic acid, methyl ester.

12. An optical isomer of the compound of claim 11, namely (8R,15S)-9-oxo-15-hydroxy-15-cyclohexyl-16,17,18,19,20-pentanorprosta-5(Z),11-dienoic acid, methyl ester.

13. A compound of claim 1, wherein X is —CH$_2$CH$_2$— and m is 3.

14. A compound of claim 13, wherein $R_2$ is hydrogen or methyl and $R_3$ is hydrogen.

15. A compound of claim 14, wherein $R_1$ is methyl.

16. A compound of claim 15, wherein $R_4$ is hydrogen and $R_5$ is alkyl of 4-6 carbon atoms or optionally substituted phenoxy.

17. A compound of claim 16, wherein $R_2$ is hydrogen and $R_5$ is phenoxy, namely (8R,15S)-15-hydroxy-9-oxo-16-phenoxy,-17,18,19,20-tetranorprosta-11-enoic acid, methyl ester.

18. A compound of claim 16, wherein $R_2$ is hydrogen and $R_5$ is n-butyl, namely (8R,15S)-9-oxo-15-hydroxyprosta-11-enoic acid, methyl ester.

19. A compound of claim 15, wherein $R_2$ is hydrogen, and $R_4$ and $R_5$ taken together with the carbon to which they are attached represent cyclohexyl, namely (8R,15S)-9-oxo-15-hydroxy-15-cyclohexyl-16,17,18,19,20-pentanorprosta-11-enoic acid, methyl ester.

20. A compound of claim 1, wherein X is —CH$_2$CH=C=CH— and m is 1.

21. A compound of claim 20, wherein $R_2$ is hydrogen or methyl and $R_3$ is hydrogen.

22. A compound of claim 21, wherein $R_1$ is methyl.

23. A compound of claim 22, wherein $R_4$ is hydrogen and $R_5$ is alkyl of 4-6 carbon atoms or optionally substituted phenoxy.

24. A compound of claim 23, wherein $R_2$ is hydrogen and $R_5$ is phenoxy, namely (8R,15S)-9-oxo-15-hydroxy-16-phenoxy-17,18,19,20-tetranorprosta-3,4,11-trienoic acid, methyl ester.

25. A compound of claim 23, wherein $R_2$ is hydrogen and $R_5$ is n-butyl, namely (8R,15S)-9-oxo-15-hydroxy-prosta-3,4,11-trienoic acid, methyl ester.

26. A compound of claim 22, wherein $R_2$ is hydrogen, and $R_4$ and $R_5$ taken together with the carbon to which they are attached represent cyclohexyl, namely (8R,15S)-9-oxo-15-hydroxy-15-cyclohexyl-16,17,18,19,20-pentanorprosta-3,4,11-trienoic acid, methyl ester.

27. A composition suitable for administration to a mammal having a disease-state chosen from hypertension and excessive gastric acid secretion, which composition comprises a therapeutically effective amount of a compound of the formula

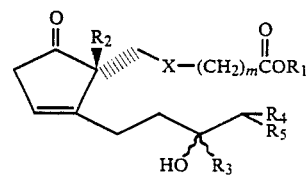

wherein:
m is 1 or 3;
$R_1$ is hydrogen or alkyl of 1-6 carbon atoms;
$R_2$ is hydrogen or lower alkyl of 1-4 carbon atoms;
$R_3$ and $R_4$ are independently hydrogen or methyl;
$R_5$ is alkyl of 4-10 carbon atoms, $CF_3(CH_2)_n$— in which n is an integer of 3-5, cycloalkyl of 4-8 carbon atoms, or phenyl, benzyl or phenoxy in which any phenyl group may be optionally substituted with one or two substituents chosen from lower alkyl of 1-4 carbon atoms, lower alkoxy of 1-4 carbon atoms, lower thioalkyl of 1-4 carbon atoms, halogen, trifluoromethyl and trifluoromethoxy; or
$R_4$ and $R_5$ taken together with the carbon to which they are attached is cycloaklyl of 4-8 carbon atoms;
X is cis —CH=CH— or —CH$_2$CH$_2$— when m is 3, or
X is —CH$_2$CH=C=CH— when m is 1;
and the wavy lines represent the $\alpha$ or $\beta$ configuration with the proviso that when one wavy line is $\alpha$ the other is $\beta$;
or a pharmaceutically acceptable, non-toxic salt thereof, in admixture with one or more pharmaceutically acceptable non-toxic carriers.

28. A method for treating a mammal having a disease-state chosen from hypertension and excessive gastric acid secretion, which comprises administering a therapeutically effective amount of a compound of the formula

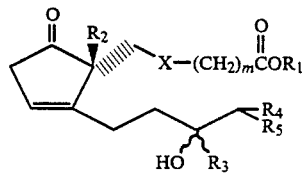

wherein:
m is 1 or 3;
$R_1$ is hydrogen or alkyl of 1-6 carbon atoms;
$R_2$ is hydrogen or lower alkyl of 1-4 carbon atoms;
$R_3$ and $R_4$ are independently hydrogen or methyl;
$R_5$ is alkyl of 4-10 carbon atoms, $CF_3(CH_2)_n$— in which n is an integer of 3-5, cycloalkyl of 4-8 carbon atoms, or phenyl, benzyl or phenoxy in which any phenyl group may be optionally substituted with one or two substituents chosen from lower alkyl of 1-4 carbon atoms, lower alkoxy of 1-4 carbon atoms, lower thioalkyl of 1-4 carbon atoms, halogen, trifluoromethyl and trifluoromethoxy; or
$R_4$ and $R_5$ taken together with the carbon to which they are attached is cycloalkyl of 4-8 carbon atoms;
X is cis —CH=CH— or —CH$_2$CH$_2$— when m is 3, or
X is —CH$_2$CH=C=CH— when m is 1;
and the wavy lines represent the $\alpha$ or $\beta$ configuration with the proviso that when one wavy line is $\alpha$ the other is $\beta$;
or a pharmaceutically acceptable, non-toxic salt thereof.